(12) United States Patent
Takeuchi et al.

(10) Patent No.: US 6,306,509 B2
(45) Date of Patent: *Oct. 23, 2001

(54) ION CONDUCTIVE LAMINATE AND PRODUCTION METHOD AND USE THEREOF

(75) Inventors: Masataka Takeuchi; Shuichi Naijo; Takashi Ohkubo, all of Chiba (JP); Junji Yotsuyanagi; Motoyuki Hirata, both of Kawasaki (JP)

(73) Assignee: Showa Denko K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/946,850

(22) Filed: Oct. 8, 1997

Related U.S. Application Data

(63) Continuation-in-part of application No. 08/822,465, filed on Mar. 21, 1997, and a continuation-in-part of application No. PCT/JP97/00944, filed on Mar. 21, 1997.
(60) Provisional application No. 60/014,567, filed on Apr. 1, 1996.

(30) Foreign Application Priority Data

Mar. 21, 1996 (JP) .................................................. 8-093682

(51) Int. Cl.[7] ............................................. B32B 27/00
(52) U.S. Cl. ...................... 428/425.8; 428/408; 428/412; 428/458; 428/477.7; 428/482
(58) Field of Search ........................... 428/458, 474.4, 428/477.7, 482, 412, 408, 423.1, 423.7, 425.5, 425.8; 429/191, 192, 193, 207, 209; 156/160, 272.2, 273.3

(56) References Cited

U.S. PATENT DOCUMENTS

| | | | |
|---|---|---|---|
| 4,830,939 | 5/1989 | Lee et al. | 429/192 |
| 4,911,995 | * 3/1990 | Belanger et al. | 429/192 |
| 5,206,756 | 4/1993 | Cheshire | 359/270 |
| 5,217,827 | 6/1993 | Fauteux et al. | 429/192 |
| 5,376,210 | 12/1994 | Brochu et al. | 156/344 |
| 5,520,851 | * 5/1996 | Yu et al. | 252/518 |
| 5,536,278 | 7/1996 | St-Amant et al. | 29/623.3 |
| 5,567,287 | * 10/1996 | Joshi et al. | 204/265 |
| 5,597,661 | 1/1997 | Takeuchi et al. | 429/42 |
| 5,665,490 | 9/1997 | Takeuchi et al. | 429/192 |

FOREIGN PATENT DOCUMENTS 3-89457   4/1991   (JP) .

* cited by examiner

Primary Examiner—Deborah Jones
Assistant Examiner—Stephen Stein
(74) Attorney, Agent, or Firm—Sughrue, Mion, Zinn, Macpeak & Seas, PLLC

(57) ABSTRACT

A laminate comprising an ion conductive material having excellent ion conductivity at room temperature or at lower temperatures, a small water content, sufficiently high mechanical strength and storage stability to allow for handling the ion conductive material in practice, and a form which is easily integrated into an electrochemical element or electrochemical devices. Also disclosed is a production method thereof, and a method of producing a battery, a capacitor or an electrochemical element or apparatus using the laminate. The laminate comprises an intermediate layer of an ion conductive material having on the upper and lower portions thereof outer layers having an ion conductivity lower than that of the intermediate layer. Furthermore, at least one of the outer layers is a layer comprising a non electron-conductive material.

25 Claims, 8 Drawing Sheets

ION CONDUCTIVE LAMINATE AND PRODUCTION METHOD AND USE THEREOF

CROSS REFERENCE TO RELATED APPLICATIONS

This is a continuation-in-part of (1) U.S. application Ser. No. 08/822,465, filed Mar. 21, 1997, which in turn claims benefit of U.S. Provisional Application No. 60/014,567, filed Apr. 1, 1996 and of Japanese Patent Application 8/93682, filed March 21, 1996; and is a continuation in part (2) International Application PCT/JP97/00944, filed Mar. 21, 1997, which claims benefit from Japanese Patent Application 8/93682, filed Mar. 21, 1996.

FIELD OF THE INVENTION

The present invention relates to a laminate comprising an ion conductive material such as a solid polymer electrolyte or polymer gel electrolyte, and a method for producing an ion conductive laminate. The present invention also relates to a method for producing an electrochemical element and apparatus utilizing the ion conductive laminate.

BACKGROUND OF THE INVENTION

To cope with the trend towards downsizing or solidification in the field of ionics, a solid electrolyte material has been proposed as a new ion conductive material in place of conventional electrolytic solutions. Investigators have aggressively attempted to apply the electrolyte material to solid primary or secondary batteries, electrolytic capacitors, electrical double layer capacitors, photoelectric cells, solar cells, fuel cells, electrochromic elements, various sensors and antistatic film.

Conventional batteries using an electrolytic solution employ a porous thin film separator impregnated with an electrolytic solution. In this case, the production and processing cost of the porous film is high which in turn increases the cost of conventional batteries. Furthermore, the film is not capable of holding the electrolytic solution. This causes the solution to leak from the battery or causes the electrode substance to elute, thereby giving rise to problems with respect to long-term reliability and safety of the battery.

On the other hand, products using a solid electrolyte material are generally free from the above-described problems and are furthermore capable of providing a product having a reduced thickness. Additionally, the solid electrolyte has excellent heat resistance and is advantageously employed in the production of products such as batteries. In particular, batteries employing a solid electrolyte material containing a polymer as a constituent component have better flexibility as compared with those using an inorganic material, and are advantageous in that they can be formed into various shapes.

As an example of a solid electrolyte material containing a polymer as a constituent component (hereinafter also referred to as a "solid polymer electrolyte" or "polymer gel electrolyte"), *Br. Polym. J.*, Vol. 319, page 137 (1975) describes a composite of a polyethylene oxide with an inorganic alkali metal salt. However, the ion conductivity thereof at room temperature is as low as $10^{-7}$ S/cm.

In recent years, a comb structure polymer has been reported having introduced into the side chain thereof an oligooxyethylene which elevates the thermal motility of the oxyethylene chain bearing ion conductivity, to thereby improve the ion conductivity of the polymer. For example, *J. Phys. Chem.*, Vol. 89, page 987 (1984) describes a polymethacrylic acid having added to the side chain thereof an oligooxyethylene compounded with an alkali metal salt. Furthermore, *J. Am. Chem. Soc.*, Vol. 106, page 6,854(1984) describes a polyphosphazene having an oligooxyethylene side chain compounded with an alkali metal salt.

U.S. Pat. No. 4,357,401 describes a solid polymer electrolyte having an ion conductivity at 50° C. of approximately from $10^{-4}$ to $10^{-5}$ S/cm which can be obtained by compounding a metal salt with a cross-linked polymer having reduced crystallinity. U.S. Pat. No. 4,792,504 proposes to improve the ion conductivity by using a cross-linked solid polymer electrolyte impregnated with an electrolytic solution comprising a metal salt and an aprotic solvent in polyethylene oxide having a continuous network.

Furthermore, in recent years, an electrical double layer capacitor has been used, for example, as a memory backup power source, where a carbon material having a large specific surface area, such as activated carbon and carbon black, is used as a polarizable electrode, and an ion conductive solution is deposited between such electrodes. For example, *Kino Zairyo* (*Functional Materials*), page 33 (February, 1989) describes a capacitor employing a carbon-base polarizable electrode and an organic electrolytic solution, and 173th *Electrochemical Society Meeting, Atlanta, Georgia,* No. 18 (May, 1988) describes an electrical double layer capacitor using an aqueous sulfuric acid solution. Furthermore, Japanese Unexamined Patent Publication (kokai) No. 63-244570 discloses a capacitor employing $Rb_2Cu_3I_3Cl_7$ which has a high electrical conductivity as an inorganic solid electrolyte.

However, electrical double layer capacitors using a known electrolytic solution are bound to create problems with respect to long-term use or reliability. This is because the solution readily leaks from the capacitor under severe conditions such as when the capacitor is used for a long period of time or when a high voltage is applied thereto. On the other hand, electrical double layer capacitors using a conventional inorganic ion conductive substance are disadvantageous in that the decomposition voltage of the ion conductive substance is low and the output voltage is low.

Japanese Unexamined Patent Publication (kokai) No.4-253771 proposes to use a polyphosphazene-base polymer as an ion conductive substance for batteries or electrical double layer capacitors. When a solid ion conductive substance mainly comprising the above-described polymer is used, the resulting advantages are that the output voltage is relatively high as compared with that obtained when an inorganic ion conductive substance is used, the device can be formed into various shapes, and sealing is easy.

The solid polymer electrolyte under general investigation has an improved ion conductivity of approximately from $10^{-4}$ to $10^{-5}$ S/cm. However, this is still in a low level that is two order of magnitude or more lower than the ion conductivity of a liquid ion conductive material. Furthermore, the ion conductivity considerably decreases at a temperature of 0° C. and below.

In order to improve ion conductivity, the polymers for use in the solid polymer electrolyte have a low glass transition temperature. If the glass transition temperature is lowered, a problem arises in that the polymer has reduced mechanical strength which causes difficulties in industrial handling. Furthermore, when a solvent is added to further improve the ion conductivity, the mechanical strength disadvantageously is further reduced.

The polymers for use in the solid polymer electrolyte usually absorb water, and water absorptivity is a problem when used in non-aqueous electrochemical elements such as lithium (ion) batteries or electrical double layer capacitors.

In addition to the above described batteries and capacitors, the ion conductive material is an important constituent material of electrochemical devices such as electrochromic displays and power generating apparatuses such as photoelectric cells and solar cells, and as an electrochemical element for use in assembling these devices such as electrochemical power generating elements, electrochemical coloring elements and electrochemical light-emitting elements. The ion conductive material is an important constituent of antistatic materials which are capable of eliminating undesirable electrostatic effects and can also be used as a sensor material. However, the above described problems of conventional ion conductive materials with respect to batteries or capacitors are also encountered in the production of products for these additional uses. Accordingly, there is a need to overcome the above problems of the prior art, to develop solid polymer electrolyte materials having excellent ion conductivity, and to develop ion conductive materials which can be easily integrated into an electrochemical element or electrochemical apparatus as a solid polymer electrolyte.

SUMMARY OF THE INVENTION

An object of the present invention is to provide an ion conductive material and a laminate thereof having excellent ion conductivity at room temperature or at lower temperatures, a low water content, sufficiently high mechanical strength and storage stability to allow for practical handling, and a form which is easily integrated into electrochemical elements or electrochemical apparatuses.

Another object of the present invention is to provide a method for producing the above described ion conductive laminate.

Yet another object of the present invention is to provide a method of producing an electrochemical apparatus having high capability and excellent reliability including an electrochemical element, an electrochemical power generating element, a coloring element or a light-emitting element, such as a battery, an electrical double layer capacitor, an electrochromic element, a photoelectric cell and a solar cell, and an electrically conductive material using the ion conductive laminate of the present invention.

As a result of extensive investigations on the above-described problems, the present inventors have discovered that a laminate of a layer comprising an ion conductive material and having provided on the upper part and the lower part thereof a liquid-impermeable, particularly, water-impermeable layer comprising a non electron-conductive material having an ion conductivity lower than that of the ion conductive material, and a liquid-impermeable, particularly, water-impermeable layer comprising a material having an ion conductivity lower than the ion conductive material, respectively, can overcome problems with respect to atmosphere control or strength in industrial handling of the ion conductive material. The present invention has been accomplished based on this finding.

More specifically, the present invention provides a laminate comprising an intermediate layer of an ion conductive material and outer layers each comprising a non ion-conductive material, at least one outer layer comprising a non electron-conductive material; a laminate comprising an intermediate layer of an ion conductive material, one outer layer comprising a non ion-conductive material and another outer layer comprising a material having an ion conductivity lower than that of the ion conductive material in the intermediate layer, at least one outer layer being a layer comprising a non electron-conductive material; or a laminate comprising an intermediate layer of an ion conductive material and outer layers each comprising a material having an ion conductivity lower than that of the ion conductive material in the intermediate layer, at least one outer layer being a layer comprising a non electron-conductive material; and a production method thereof. Furthermore, the present invention provides a method of using the above-described laminates, where the ion conductive material held in the laminate can be industrially handled more easily than conventional materials, to produce various electrochemical apparatuses while keeping its excellent quality; a method, according to the above-described method of use, for producing an electrochemical apparatus including an electrochemical element, an electrochemical power generating element, a coloring element and a light-emitting element, such as a battery, a capacitor, an electrochromic display, a photoelectric cell and a solar cell; and a method for producing an electrically conductive material using the above-described laminate.

The present invention relates to the following structures and methods:

(1) A laminate comprising Layer A, Layer B and Layer C, wherein Layer A is disposed between Layer B and Layer C, Layer A comprises an ion conductive material, Layer B and Layer C each comprises a material having an ion conductivity lower than that of Layer A, and at least one of Layer B and Layer C comprises a non electron-conductive material.

(2) The laminate as described in (1) above, wherein at least one of Layer B and Layer C has a contact angle of 80° or less with polyethylene glycol having an average molecular weight of about 400.

(3) The laminate as described in (1) above, wherein at least one of Layer B and Layer C has a contact angle of 60° or less with polyethylene glycol having an average molecular weight of about 400.

(4) The laminate as described in any one of (1) to (3) above, wherein Layer B and Layer C each is a liquid impermeable layer.

(5) The laminate as described in any one of (1) to (4) above, wherein Layer B and Layer C each is a water impermeable layer.

(6) The laminate as described in any one of (1) to (5) above, wherein at least one of Layer B and Layer C comprises a material having a dielectric constant of 8 or less.

(7) The laminate as described in any one of (1) to (6) above, wherein at least one of Layer B and Layer C has an ion conductivity that is one tenth the ion conductivity of Layer A or less.

(8) The laminate as described in any one of (1) to (7) above, wherein at least one of Layer B and Layer C comprises a thermoplastic resin or a composition containing a thermoplastic resin.

(9) The laminate as described in any one of (1) to (7) above, wherein at least one of Layer B and Layer C comprises an engineering plastic, a thermosetting resin or a composition containing one of an engineering plastic or a thermosetting resin.

(10) The laminate as described in any one of (1) to (9) above, wherein the ion conductive material of Layer A has a specific resistivity of $10^6$ Ω·cm or less.

(11) The laminate as described in any one of (1) to (9) above, wherein the ion conductive material of Layer A has a specific resistivity of $10^5$ Ω·cm or less.

(12) The laminate as described in any one of (1) to (11) above, wherein Layer A has a thickness of from 0.1 to 1,000 μm.

(13) The laminate as described in any one of (1) to (12) above, wherein Layer A has a water content of 200 ppm or less.

(14) The laminate as described in any one of (1) to (13) above, wherein Layer A has a peel strength such that Layer B or Layer C can be peeled off without substantially deforming the shape of Layer A.

(15) The laminate as described in any one of (1) to (14) above, wherein at least one of Layer B and Layer C is a light transmissible layer.

(16) The laminate as described in any one of (1) to (14) above, wherein none of Layer B and Layer C are light-transmissible layers.

(17) The laminate as described in any one of (1) to (16) above, wherein both Layer B and Layer C are gas impermeable layers.

(18) The laminate as described in any one of (1) to (17) above, wherein Layer B or Layer C comprises an electron conductive material, and the electron conductive material-containing layer is connected to an electron conductive electric conductor.

(19) The laminate as described in any one of (1) to (17) above, wherein electron conductive electric conductors are connected to two different sites of Layer A.

(20) The laminate as described in any one of (1) to (19) above, wherein Layer A comprises a material containing a cross-linked polymer as a constituent component.

(21) The laminate as described in any one of (1) to (19) above, wherein Layer A comprises a material containing a cross-linked polymer having at least one alkyleneoxy-containing chain in the main chain and/or in the side chain thereof as a constituent component.

(22) The laminate as described in any one of (1) to (19) above, wherein Layer A comprises a material containing a cross-linked polymer having at least one alkyleneoxy-containing chain and at least one —NH—C(=O)—O— bond in the main chain and/or in the side chain thereof as a constituent component.

(23) The laminate as described in any one of (1) to (19) above, wherein Layer A comprises a material containing, as a constituent component, a polymer of a (meth)acryloyl-base compound having a structure substituted by at least one unit represented by formula (1) and/or a copolymer containing said compound as a copolymer component:

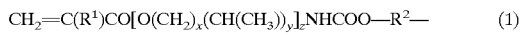

$$CH_2=C(R^1)CO[O(CH_2)_x(CH(CH_3))_y]_zNHCOO-R^2- \quad (1)$$

wherein $R^1$ represents hydrogen or an alkyl group, $R^2$ represents a divalent organic group containing an oxyalkylene group, the organic group may have any of linear, branched and cyclic structures and may contain one or more elements other than carbon, hydrogen and oxygen, x and y each represents 0 or an integer of from 1 to 5, z represents 0 or a numerical value of from 1 to 10, provided that when both of x and y are zero, z is zero, the moiety ($CH_2$) and the moiety ($CH(CH_3)$) may be randomly configured, provided that when two or more units represented by formula (1) are present in the same molecule, $R^1$ and $R^2$ of one unit may be different from $R^1$ and $R^2$ of the other units, and the values x, y and z of one unit may be different from the values x, y and z of the other units.

(24) The laminate as described in any one of (1) to (23) above, wherein the ion conductive material of Layer A contains an electrolyte salt and/or a solvent.

(25) The laminate as described in (24) above, wherein the electrolyte salt is at least one selected from the group consisting of an alkali metal salt, a quaternary ammonium salt and a quaternary phosphonium salt.

(26) The laminate as described in (24) or (25) above, wherein the solvent is at least one selected from the group consisting of a carbonate-base compound, a lactone-base compound and an ether-base compound, each having a dielectric constant of 1 or more.

(27) The laminate as described in any one of (1) to (26) above, further comprising a thin layer comprising a metal, a metal oxide or carbon which is present between Layer A and Layer B and/or between Layer A and Layer C.

(28) The laminate as described in any one of (1) to (27) above, further comprising an electron conductive thin layer which is present between Layer A and either one of Layer B and Layer C, and the other of Layer B and Layer C comprises a non electron-conductive material.

(29) The laminate as described in (27) or (28) above, wherein the thin layer is connected to an electron conductive electric conductor.

(30) A method for producing the laminate described in any one of (1) to (26) above, comprising the steps of (i) laminating Layer A on Layer B in such manner that the material of Layer A substantially does not flow or move on Layer B, to provide a laminate structure consisting of Layer B/Layer A, wherein Layer A comprises an ion conductive material and Layer B comprises a material having an ion conductivity lower than that of Layer A, (ii) laminating Layer C on Layer A to provide a laminate structure consisting of Layer B/Layer A/Layer C, wherein Layer C comprises a material having an ion conductivity lower than that of Layer A, and (iii) then applying pressure to the laminate structure with a force applied on the Layer B side surface and a force in opposition thereto applied on the Layer C side surface.

(31) A method for producing the laminate described in any one of (1) to (26) above, comprising the steps of (i) laminating Layer A on Layer B in such manner that the material of Layer A substantially does not flow or move on Layer B, to provide a laminate structure consisting of Layer B/Layer A, wherein Layer A comprises an ion conductive material containing a curable substance and Layer B comprises a material having an ion conductivity lower than that of Layer A, (ii) laminating Layer C on Layer A to provide a laminate structure consisting of Layer B/Layer A/Layer C, wherein Layer C comprises a material having an ion conductivity lower than that of Layer A, and (iii) then applying pressure to the laminate structure with a force applied on the Layer B side surface and a force in opposition thereto applied on the Layer C side surface.

(32) A method for producing the laminate described in any one of (1) to (26) above, comprising the steps of (i) laminating Layer A on Layer B in such manner that the material of Layer A substantially does not flow or move on Layer B, to provide a laminate structure consisting of Layer B/Layer A, wherein Layer A comprises an ion conductive material containing a curable substance and Layer B comprises a material having an ion conductivity lower than that of Layer A, (ii) heating and/or irradiating the laminate structure with active light to cure Layer A, (iii) laminating Layer C on Layer A to provide a laminate structure consisting of Layer B/Layer A/Layer C, wherein Layer C comprises a material having an ion conductivity lower than that of Layer A, and (iv) then applying pressure to the laminate structure with a force applied on the Layer B side surface and a force in opposition thereto applied on the Layer C side surface.

(33) The method for producing a laminate according to any one of (30) to (32) above, wherein the laminate is heated and/or irradiated with active light before or during the pressure applying step.

(34) The method for producing a laminate according to any one of (30) to (33) above, wherein the laminate structure consisting of Layer B/Layer A comprises Layer A substantially in a non-flowable state as a constituent layer which is obtained by laminating Layer A comprising an ion conductive material containing a solvent on Layer B comprising a material having an ion conductivity lower than that of Layer A in such manner that the material of Layer A substantially does not flow or move on Layer B and then removing the solvent.

(35) A method for producing the laminate described in any one of (1) to (26) above, comprising the steps of (i) forming a thin layer $D_1$ comprising a metal, a metal oxide or carbon on one surface of Layer B, (ii) laminating Layer A on the thin layer $D_1$ in such manner that the material of Layer A substantially does not flow or move on the thin layer $D_1$, to provide a laminate structure consisting of Layer B/thin layer $D_1$/Layer A, (iii) laminating Layer C on Layer A to provide a laminate structure consisting of Layer B/thin layer $D_1$/Layer A/Layer C, and (iv) then applying pressure to the laminate structure with a force applied on the Layer B side surface and a force in opposition thereto applied on the Layer C side surface, wherein Layer A comprises an ion conductive material and Layer B and Layer C each comprises a material having an ion conductivity lower than that of Layer A.

(36) A method for producing the laminate described in any one of (1) to (26) above, comprising the steps of (i) forming a thin layer $D_2$ comprising a metal, a metal oxide or carbon on one surface of Layer C, (ii) laminating on the thin layer $D_2$ the Layer A surface of a laminate structure consisting of Layer B/Layer A obtained by laminating Layer A on Layer B in such manner that the material of Layer A substantially does not flow or move on Layer B, to provide a laminate structure consisting of Layer C/thin layer $D_2$/Layer A/Layer B, and (iii) then applying pressure to the laminate structure with a force applied on the Layer B side surface and a force in opposition thereto applied on the Layer C side surface, wherein Layer A comprises an ion conductive material and Layer B and Layer C each comprises a material having an ion conductivity lower than that of Layer A.

(37) A method for producing the laminate described in any one of (1) to (26) above, comprising the steps of (i) forming a thin layer $D_1$ comprising a metal, a metal oxide or carbon on one surface of Layer B, (ii) laminating Layer A on the thin layer $D_1$ in such manner that the material of Layer A substantially does not flow or move on the thin layer, to provide a laminate structure consisting of Layer B/thin layer $D_1$/Layer A, (iii) laminating Layer C on Layer A to provide a laminate structure consisting of Layer B/thin layer $D_1$/Layer A/Layer C, and (iv) then applying pressure to the laminate structure with a force applied on the Layer B side surface and a force in opposition thereto applied on the Layer C side surface, wherein Layer A comprises an ion conductive material containing a curable substance and Layer B and Layer C each comprises a material having an ion conductivity lower than that of Layer A.

(38) A method for producing the laminate described in any one of (1) to (26) above, comprising the steps of (i) forming a thin layer $D_2$ comprising a metal, a metal oxide or carbon on one surface of Layer C, (ii) laminating on the thin layer $D_2$ the Layer A surface of a laminate structure consisting of Layer B/Layer A obtained by laminating Layer A on Layer B in such manner that the material of Layer A substantially does not flow or move on Layer B, to provide a laminate structure consisting of Layer C/thin layer $D_2$/Layer A/Layer B, and (iii) then applying pressure to the laminate structure with a force applied on the Layer B side surface and a force in opposition thereto applied on the Layer C side surface, wherein Layer A comprises an ion conductive material containing a curable substance and Layer B and Layer C each comprises a material having an ion conductivity lower than that of Layer A.

(39) A method for producing the laminate described in any one of (1) to (26) above, comprising the steps of (i) forming a thin layer $D_1$ comprising a metal, a metal oxide or carbon on one surface of Layer B, (ii) laminating Layer A on the thin layer $D_1$ in such manner that the material of Layer A substantially does not flow or move on the thin layer $D_1$, to provide a laminate structure consisting of Layer B/thin layer $D_1$/Layer A, wherein Layer A comprises an ion conductive material containing a curable substance and Layer B comprises a material having an ion conductivity lower than that of Layer A, (iii) heating and/or irradiating the laminate structure with active light to cure Layer A, (iv) laminating Layer C on Layer A to provide a laminate structure consisting of Layer B/thin layer $D_1$/Layer A/Layer C, wherein Layer C comprises a material having an ion conductivity lower than that of Layer A, and (v) then applying pressure to the laminate structure with a force applied on the Layer B side surface and a force in opposition thereto applied on the Layer C side surface.

(40) A method for producing the laminate described in any one of (1) to (26) above, comprising the steps of (i) laminating Layer A on Layer B in such manner that the material of Layer A substantially does not flow or move on Layer B, to provide a laminate structure consisting of Layer B/Layer A, wherein Layer A comprises an ion conductive material containing a curable substance and Layer B comprises a material having an ion conductivity lower than that of Layer A, (ii) heating and/or irradiating the laminate structure with active light to cure Layer A, (iii) laminating the thin layer $D_2$ surface of Layer C having on one surface thereof a thin layer $D_2$ comprising a metal, a metal oxide or carbon, to provide a laminate structure consisting of Layer C/thin layer $D_2$/Layer A/Layer B, wherein Layer C comprises a material having an ion conductivity lower than that of Layer A, and (iv) then applying pressure to the laminate structure with a force applied on the Layer B side surface and a force in opposition thereto applied on the Layer C side surface.

(41) A method for producing an electrochemical element which comprises (i) removing at least one of Layer B and Layer C from Layer A of the laminate described in any one of (1) to (29) above, or removing Layer B or Layer C having on the surface thereof facing Layer A a thin-layer comprising a metal, a metal oxide or carbon, together with the thin layer from Layer A of the laminate and (ii) forming a layer comprising a material containing an electrochemically-active substance on at least one removal surface of Layer A.

(42) A method for producing an electrochemical power generating element which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(43) A method for producing an electrochemical coloring element which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(44) A method for producing an electrochemical light-emitting element which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(45) A method for producing a battery which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(46) A method for producing a capacitor which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(47) A method for producing an electrochromic element which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(48) A method for producing a photoelectric cell which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(49) A method for producing a solar cell which comprises (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, and (ii) forming a layer comprising a material containing an electrochemically-active substance on at least one removal surface of Layer A.

(50) A method for producing an electrochemical element having a Layer B/Layer A/Layer C, Layer B/Layer A/Layer B or Layer C/Layer A/Layer C laminate structure comprising (i) removing at least one of Layer B and Layer C from Layer A of the laminate described in any one of (1) to (29) above, or removing Layer B or Layer C having on the surface thereof facing Layer A a thin layer comprising a metal, a metal oxide or carbon, together with the thin layer from Layer A of the laminate, to produce a Layer A/Layer C or Layer B/Layer A laminate, and (ii) laminating the thus obtained laminate on a Layer A/Layer C or Layer B/Layer A laminate produced in the same manner such that Layers A of the respective laminates are bonded together.

Figure 1:
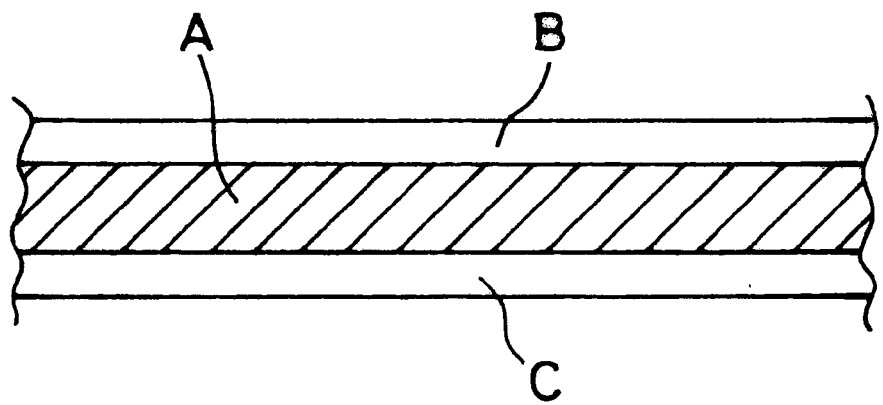
FIG. 1 is a schematic cross section of the laminate in one example of the present invention.
Figure 2:
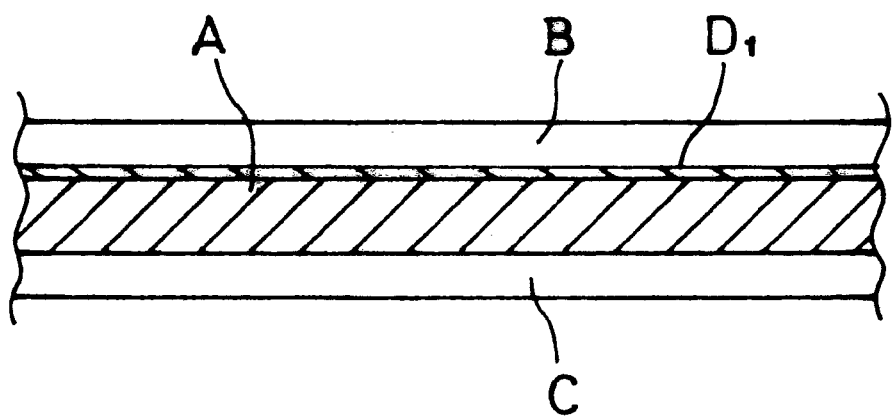
FIG. 2 is a schematic cross section of the laminate in one example of the present invention.
Figure 3:
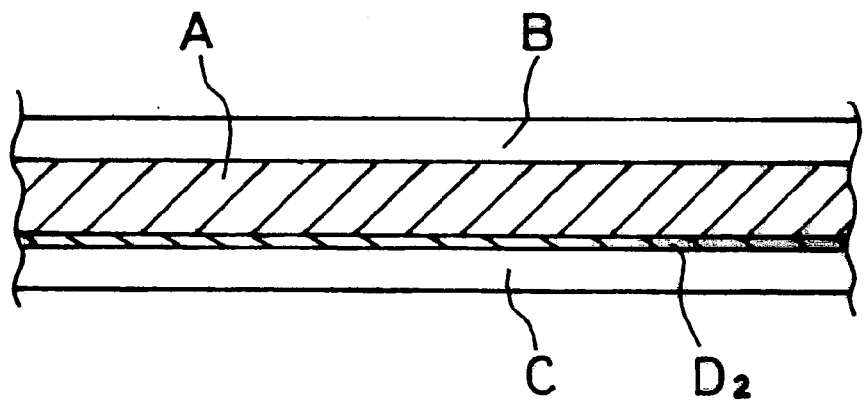
FIG. 3 is a schematic cross section of the laminate in one example of the present invention.
Figure 4:
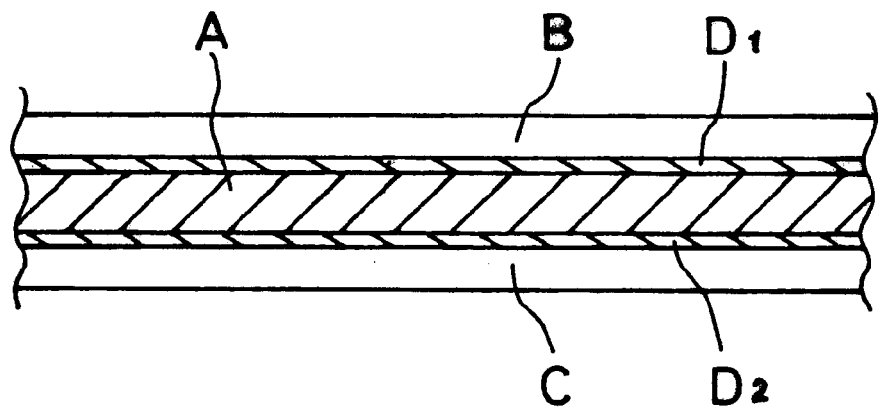
FIG. 4 is a schematic cross section of the laminate in one example of the present invention.
Figure 5:
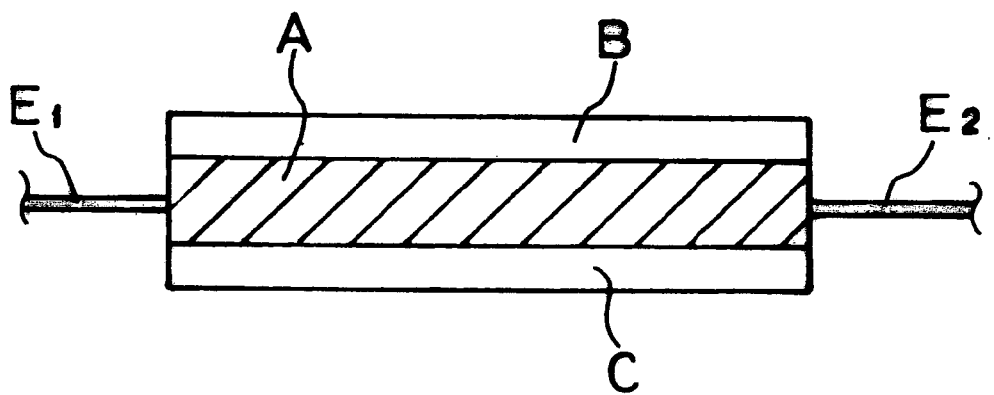
FIG. 5 is a schematic cross section of the laminate in one example of the present invention.
Figure 6:
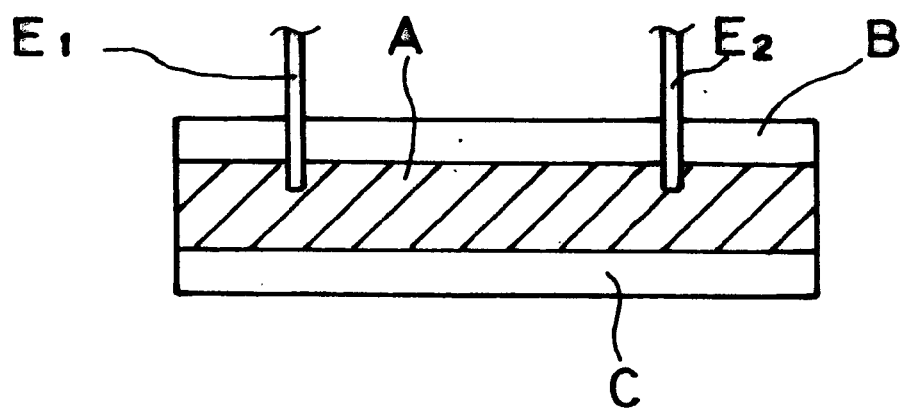
FIG. 6 is a schematic cross section of the laminate in one example of the present invention.
Figure 7:
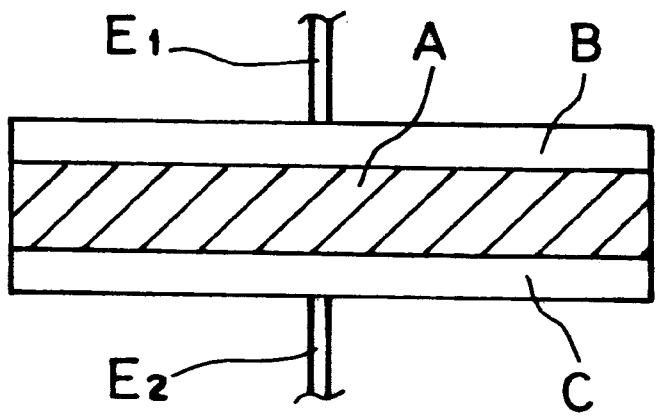
FIG. 7 is a schematic cross section of the laminate in one example of the present invention.
Figure 8:
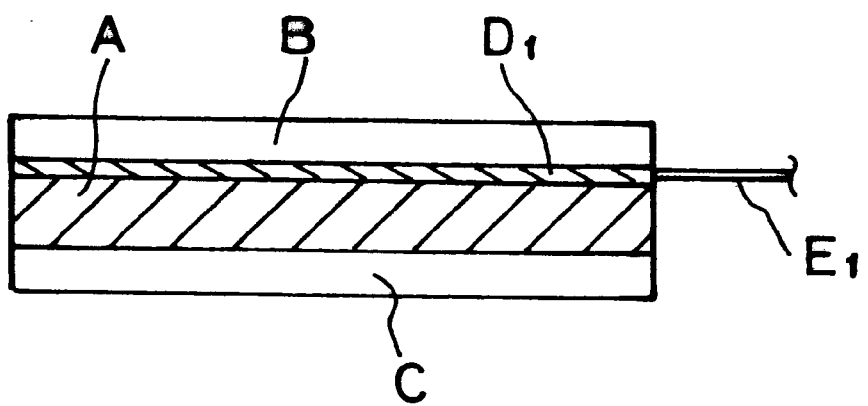
FIG. 8 is a schematic cross section of the laminate in one example of the present invention.

The symbols used in FIGS. 1 to 15 (letters or numerals) each has the following meaning:

A Layer A: ion conductive material layer
B Layer B: layer comprising a material having an ion conductivity lower than that of Layer A
C Layer C: layer comprising a material having an ion conductivity lower than that of Layer A
$D_1$ thin layer $D_1$ comprising a metal, a metal oxide or carbon
$D_2$ thin layer $D_2$ comprising a metal, a metal oxide or carbon
$E_1$ electron conductive electric conductor
$E_2$ electron conductive electric conductor
1 positive electrode
2 solid polymer electrolyte or polymer gel electrolyte
3 negative electrode
4 current collecting body
5 insulating spacer
6 insulating resin sealant
7 polarizable electrode 8 lead wire
9 glass
10 transparent electrically conductive layer
11 electrochromic layer
12 counter electrode
13 electrode
14 electrode
15 substrate A
16 substrate B

DETAILED DESCRIPTION OF THE INVENTION

The present invention is described in detail below.

The ion conductive material for use in the ion conductive laminate of the present invention includes a substance having an ion conductivity (ion conductive substance), a mixture or composite containing an ion conductive substance, a mixture or composite containing an ionic substance and an ion conductive substance, and a material containing the above-described mixture or composite and in addition, a curable substance, a solvent, an additive, a filler or other additives, which material is capable of exhibiting ion conductivity. The ion conductive material may be in the form of any of a liquid, sol, solid and gel. The ion conductive material for use in the laminate of the present invention includes, depending upon its intended application, a material comprising a so-called precursor which is converted to acquire more preferred ion conductive properties or has physical or chemical properties which have been changed, for example, by heating, irradiating with active light or removing solvent.

The term "ionic substance" as used herein means a substance which provides an ion as a carrier for conducting electricity, and in which an applied electric field causes a current to flow by moving an electric charge. Examples thereof include substances containing various ionic species as a component, such as alkali metal salts, quaternary ammonium salts, quaternary phosphonium salts, transition metal salts, protonic acids and polyelectrolyte salts. As the ionic substance, any ionic substance such as electrolyte salts generally used in batteries, capacitors and electrochromic elements may be suitably used. Specific examples thereof include polyelectrolyte salts such as alkali metal salts, quaternary ammonium salts, quaternary phosphonium salts and transition metal salts, and protonic acids, which are described below with respect to electrochemical elements or apparatuses such as batteries and capacitors.

Examples of the alkali metal salts for use as an electrolyte salt include $LiCF_3SO_3$, $LiPF_6$, $LiClO_4$, $LiI$, $LiBF_4$, $LiSCN$, $LiAsF_6$, $LiN(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$. Examples of the electrolyte salt such as quaternary ammonium salts, quaternary phosphonium salts and transition metal salts, and the protonic acid include quaternary ammonium salts such as $(CH_3)_4NBF_4$ and $(CH_3CH_2)_4NClO_4$, transition metal salts such as $AgClO_4$, quaternary phosphonium salts such as $(CH_3)_4PBF_4$, organic acids and salts thereof such as p-toluenesulfonic acid, and inorganic acids such as hydrochloric acid and sulfuric acid.

When the ion conductive material as Layer A of the laminate of the present invention is used as a solid polymer electrolyte (the term "solid polymer electrolyte" may hereinafter be referred to as "SPE" in short) or polymer gel electrolyte (the term "polymer gel electrolyte" may hereinafter be referred to as "PGE" in short) in an electrochemical apparatus, for example, in a secondary battery, the alkali metal is preferably lithium or a lithium alloy in view of high voltage and high capacity and the capability to reduce thickness. Accordingly, the alkali metal salt is preferably a lithium salt. When the negative electrode of the battery is a carbon material negative electrode, not only alkali metal ions but also quaternary ammonium salts, quaternary phosphonium salts, transition metal salts and various protonic acids may be used. When the ion conductive material as Layer A of the laminate of the present invention is used as a SPE or PGE in a solid electrical double layer capacitor, the kind of electrolyte salt used in the compounding is not particularly limited, and compounds containing an ion intended to be a charge carrier may be used. However, the compound preferably contains an ion having a large dissociation constant in a SPE or PGE and is capable of readily forming an electrical double layer with a polarizable electrode. Examples of the compound include quaternary ammonium salts such as $(CH_3)_4NBF_4$ and $(CH_3CH_2)_4NClO_4$, transition metal salts such as $AgClO_4$, quaternary phosphonium salts such as $(CH_3)_4PBF_4$, alkali metal salts such as $LiCF_3SO_3$, $LiPF_6$, $LiClO_4$, $LiI$, $LiBF_4$, $LiSCN$, $LiAsF_6$, $LiN(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$, organic acids and salts thereof such as p-toluenesulfonic acid, and inorganic acids such as hydrochloric acid and sulfuric acid. Among these, preferred in view of high output voltage and their large dissociation constant are quaternary ammonium salts, quaternary phosphonium salts and alkali metal salts. Among quaternary ammonium salts, those having different substituents on the nitrogen of the ammonium ion are preferred, such as $(CH_3CH_2)(CH_3CH_2CH_2CH_2)_3NBF_4$, because of their high solubility or dissociation constant in the SPE or PGE.

In the ion conductive material constituting Layer A, the mixing amount of the ionic substance such as the above-described electrolyte salt varies depending upon the polymer or other components to be mixed, and also depends upon the intended purpose of the laminate. However, if the mixing amount is too small, the number of ion carriers is deficient, whereas if it is too large, the mobility is lowered to thereby reduce the ion conductivity. Accordingly, the mixing amount in the ion conductive material is preferably from 0.1 to 70 wt %, more preferably from 1 to 50 wt %, of the total amount of the polymer and the ionic substance.

The ion conductive substance is a substance which exhibits electrical conduction in the presence of ions as a carrier for carrying electricity. The ions move within a solution or solid constituting the ion conductive substance under an applied electric field. As a result, current flows through the ion conductive substance. For example, the above-described ionic substance itself is one type of ion conductive substance. Other examples of the ion conductive substance include an ion conductive inorganic compound such as LiSiCON and NaSiCON, a derivative thereof, a mixture or composite of the inorganic compound with a polymer, an ionic polymer substance (a so-called polyelectrolyte) such as nafion, polystyrenesulfonic acid and a derivative thereof, and other polymers capable of exhibiting the above-described ion conductive electrical conduction. In the ion conductive laminates of the present invention, the production methods thereof and various usages using the laminate, polymers among the above-described substances which are capable of exhibiting electrical conduction by ion conduction are particularly preferred. Any polymer may be suitably used in the ion conductive laminate of the present invention if it is capable of exhibiting ion conductive electrical conduction.

The ion conductive material constituting Layer A of the ion conductive laminate of the present invention is particularly preferably a material comprising a SPE, a PGE or a precursor material thereof containing, as a constituent component, a polymer capable of exhibiting the above-described ion conductive electrical conduction. Additionally, in the SPE or PGE, ion conductive polymers which can dissolve or dissociate the ionic substance such as an electrolyte salt or which can absorb an electrolytic solution are more preferably used in view of the ion conductivity of Layer A or in view of electrochemical stability when used in an electrochemical element or apparatus. Those polymers having a dielectric constant higher than that of a saturated linear hydrocarbon type polymer and having one or more kinds of hetero atoms other than carbon and hydrogen in the main chain repeating unit and/or in the side chain are preferred, and those having a low glass transition temperature are more preferred. Examples thereof include polyethylene oxide, polypropylene oxide, an ethylene oxide/propylene oxide copolymer, a derivative, a graft form and a cross-linked form thereof; polymers having the above-mentioned polyalkylene oxide chain in the main chain and/or in side chain thereof; polysiloxane, polyphosphazene, poly(meth)acrylic ester, polyacrylonitrile, latex and a derivative thereof; and polymers having an ion conductivity and having at least one of O, N and S atoms in the repeating unit and/or in the side chain thereof.

In the specification of the present invention, the term "(meth)acryl . . . " is a generic term including "methacryl . . . " and "acryl . . . ", and the term "alkyleneoxy" and "oxyalkylene" have the same meaning.

Other preferred examples of the ion conductive polymer include polymers and copolymers of the following functional monomer or oligomer which is a precursor of the ion conductive polymer, and cross-linked form thereof.

A (meth)acryloyl-base compound having at least one unit represented by the following formula (1) in one molecule such as N-(meth)acryloylcarbamic acid ω-methyl oligooxyethyl ester and (meth)acryloyloxyethylcarbamic acid ω-methyl oligooxyethyl ester, (hereinafter, the compound is referred to as urethane (meth)acrylate having an oxyalkylene chain):

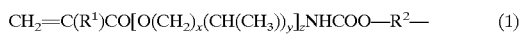

$$CH_2=C(R^1)CO[O(CH_2)_x(CH(CH_3))_y]_zNHCOO-R^2- \quad (1)$$

wherein $R^1$ represents hydrogen or a methyl group, $R^2$ represents a divalent organic group containing an oxyalkylene group, the organic group may have any of linear, branched and cyclic structures or may contain one or more elements other than carbon, hydrogen and oxygen, x and y each represents 0 or an integer of from 1 to 5, z represents 0 or a numerical value of from 1 to 10, provided that when both of x and y are zero, z is zero, the moiety ($CH_2$) and the moiety ($CH(CH_3)$) may be randomly configured, provided that when two or more units represented by formula (1) are present in the same molecule, $R^1$ and $R^2$ of one unit may be different from $R^1$ and $R^2$ of the other units, and the values x, y and z of one unit may be different from the values x, y and z of the other units.

Further included are the various urethane acrylates described in *Radiation Curing*: August, 1986, page 4 et seq., such as phenylglycidylether acrylate hexamethylene diisocyanate urethane prepolymer and phenylglicydylether acrylate isophorone diisocyanate urethane prepolymer produced by Kyoei Sha Yushi Kagaku Kogyo and others; (meth)acrylic ester and di(meth)acrylic ester each having an oxyalkylene chain (e.g., methacrylic acid ω-methyl oligooxyethyl ester), alkyl (meth)acrylates such as methyl methacrylate and n-butyl acrylate; (meth)acrylamide-base compounds such as acrylamide, methacrylamide, N,N-dimethylacrylamide, N,N-dimethylmethacrylamide, acryloylmorpholine, methacryloylmorpholine and N,N-dimethylaminopropyl(meth)acrylamide; N-vinylamide-base compounds such as N-vinylacetamide and N-vinylformamide; alkyl vinyl ethers such as ethyl vinyl ether; and polyfunctional (meth)acrylates such as hexamethylene di(meth)acrylate, timethylolpropane tri(meth)acrylate, pentaerythritol penta(meth)acrylate and dipentaerythritol hexa(meth)acrylate.

Preferred among these are urethane (meth)acrylates having an oxyalkylene chain, other various urethane acrylates, (meth)acrylate having an oxyalkylene chain and (meth)acrylamide-base compounds. Among these, considering that a larger number of urethane groups or oxyalkylene groups can be introduced into the polymer, urethane (meth)acrylates having an oxyalkylene chain are more preferred.

The polymer or copolymer of various functional monomers or oligomers described above, or a polymeric cross-linked form thereof is used as the ion conductive substance constituting Layer A of the laminate of the present invention. However, a layer containing a curable substance such as the above-described functional monomer or oligomer which is a precursor of the ion conductive substance constituting Layer A may be formed, and then the monomer or oligomer may be cured by polymerization or the like to convert the same into a polymer, a copolymer or a polymeric cross-linked form. When the polymer thus obtained contains an ionic substance or an electrolytic solution, in order to maintain the mechanical strength of the ion conductive material, the polymer is particularly preferably a polymeric cross-linked form. In producing the above-described ion conductive substance constituting Layer A or in curing the precursor material of Layer A by polymerization or the like to form Layer A, the polymerization of various functional monomers or oligomers described above is preferably performed by mixing therein at least one polyfunctional monomer or oligomer so as to obtain an ion conductive substance in a polymeric cross-linked form. The polyfunctional monomer or oligomer is particularly preferably selected from bi- or greater functional monomers or oligomers among the above-described functional monomers or oligomers. In addition, for example, a mixture of divinyl benzene, diol or polyol with diisocyanate or a polyfunctional isocyanate, or a cross-linking monomer or oligomer having a plurality of functional groups such as a vinyl group, an amino group, an isocyanate group and an epoxy group, may be appropriately used according to the objective capability.

The polymer, which is an important constituent component of the ion conductive material constituting Layer A of the ion conductive laminate of the present invention, is particularly preferably a polymer, more preferably a copolymer or a polymeric cross-linked form, containing as a monomer component, of the above-described urethane (meth)acrylates having an oxyalkylene chain, a urethane (meth)acrylate having an oxyalkylene chain and having a structure where the hydrogen atoms of at least two hydroxyl groups of a trihydric or greater polyhydric alcohol each is substituted by any unit represented by formula (1). In particular, the use of a polymer, preferably a copolymer or a polymeric cross-linked form, containing, as a monomer component, a urethane (meth)acrylate having an oxyalkylene chain substituted by three or more of the above-described units is very preferred in view of mechanical properties such as film strength, ion conductive properties and stability of the ion conductive material formed.

In Layer A of the ion conductive laminate of the present invention, a mixture of two or more of the above-described polymers may be used as a constituent material.

In the urethane (meth)acrylate having an oxyalkylene chain which is a particularly preferable functional monomer or oligomer which is used to obtain an ion conductive material constituting layer A of the ion conductive laminate of the present invention, the number of oxyalkylene units (namely, the total number of oxyalkylene units contained in $R^2$ in formula (1)) in one structural unit derived from the compound having a structure substituted by the unit represented by formula (1) is preferably from 1 to 1,000, more preferably from 5 to 200.

In the unit represented by formula (1):

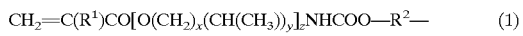

$$CH_2=C(R^1)CO[O(CH_2)_x(CH(CH_3))_y]_zNHCOO—R^2— \quad (1)$$

(a) when x is 0 or 1, y is 0 or 1 and z is 0 or 1 (provided that when both of x and y are zero, z is zero), the compound is liquid and advantageous in that the viscosity is low and reaction in a solvent system is easy.

On the other hand, in the above-described urethane (meth) acrylate having an oxyalkylene chain, which is one of the constituent materials of a SPE constituting Layer A of the ion conductive laminate of the present invention, when (b) x=2 to 5, y=0 and z=1 to 10, (c) x=1 to 5, y=1 to 5 (may be random configuration) and z=1 to 10, or (d) x=0, y=1 to 5 and z=1 to 10, the compound has reduced polymerizability and as a result, can have good storage stability and good handling as a prepolymer.

In particular, in the case of (c) and (d), when an oxypropylene group is introduced, the dielectric constant may be lowered, however, due to the properties such that the melting point and the viscosity do not increase even when the molecular weight is high, the compound can be a very useful polymer depending upon the intended application. Accordingly, by using properties of these prepolymers and combining proper prepolymers or combining the prepolymer with other polymers, a SPE suitable for a particular application can be obtained.

When the ion conductive material for use in the ion conductive laminate of the present invention contains a curable substance, the curable substance is a substance capable of curing a precursor substance (material) constituting Layer A, or converting it into a more preferred ion conductive substance, by causing a polymerization reaction or insolubilization reaction upon heating and/or irradiating with active light. The curable substance is added when the ion conductive material for use in the laminate of the present invention is a so-called precursor substance (material), namely, a material capable of being cured or converted into a more preferred ion conductive substance resulting from physical or chemical change caused by heating or irradiating with active light. Examples of the curable substance include compounds having an unsaturated double bond, compounds having a ring-opening heterocyclic ring such as an epoxy structure or a glycidyl structure, and compounds having a hydroxyl group, a thiol group, an amino group, an isocyanate group or a condensing or polycondensing group. Specific examples of these compounds include the above-described functional monomers and oligomers. Layer A containing a curable substance or a layer comprising a precursor material of Layer A is heated and/or irradiated with active light to polymerize, condense or polycondense the curable substance itself, or to react the curable substance with other substances or polymers present in the precursor substance to form a cross-linked structure, thereby curing the precursor substance (material). As a result, the material constituting Layer A has improved mechanical strength or ion conductivity as compared with that of the precursor substance.

In the ion conductive material constituting Layer A, the content of the ion conductive substance such as the above-described polymer varies depending upon the ionic substance such as an electrolyte salt mixed therein or other components, or depending upon the use of the laminate. However, if the content of the ion conductive substance is too small, the strength of Layer A, namely, the ion conductive material is too low and the shape stability of Layer A in the laminate is poor. As a result, when the laminate is used in an electrochemical element or electrochemical apparatus, the element or the apparatus (device) is disadvantageously deteriorated in performance or quality. On the other hand, if the content of the ion conductive material is too large, the amount of an ionic substance which can be contained therein or the content of a solvent or other substances used in the mixing and/or compounding is reduced to too great an extent. As a result, disadvantageously, the number of ion carries may be deficient or the ion mobility may be lowered to cause a decrease in the ion conductivity. Therefore, the amount of the ion conductive substance in the ion conductive material is preferably from 30 to 99.9 wt %, more preferably from 50 to 99 wt %, of the total amount of the ionic substance and the ion conductive substance.

The addition amount of ion conductive material constituting Layer A varies depending upon the ion conductive substance such as a polymer, the ionic substance such as an electrolyte salt, or other components used, or depending upon the use of the laminate. Also, a solvent may be appropriately present therein. When the ion conductive material for use in the ion conductive laminate of the present invention contains a solvent, the solvent is a substance contained in the ion conductive material which has a certain melting point within the range of from 15 to 80° C., or a substance which is flowable within the above-described temperature range and under a pressure of 1 kgf/cm². The solvent may be used to achieve good mixing or compounding of the ion conductive material constituting Layer A of the laminate with other substances. More specifically, the solvent may be used to achieve uniform mixing or compounding with other substances constituting a mixture or composite containing the ionic substance and the ion conductive material, such as a curable substance, an additive or a filler, or to improve the ion conductivity of the ion conductive material constituting Layer A, or to control the curing reaction by heating or irradiating the ion conductive material constituting Layer A with active light, or to improve processability in producing a laminate using the ion conductive material constituting Layer A or properties of the laminate. The solvent may be incorporated into the ion conductive material constituting Layer A in an amount as needed. However, when Layer A of the laminate of the present invention is a SPE or PGE containing a solvent, the amount of the solvent is preferably small to the extent that the solvent does not ooze out from Layer A. The solvent may be added to Layer A so as to improve proccessability or usability in producing or using the laminate of the present invention, or the solvent may be added to improve processability of a precursor material containing a precursor of the constituent material of Layer A, and then Layer A may be laminated with Layer B, Layer C or the above-described thin layer. Depending upon the kind of laminate, this technique is particularly preferred. However, when Layer A of the laminate is used substantially in the solid state, such as a SPE or PGE, the amount of the solvent is preferably reduced before use to the extent that the solvent does not ooze out from Layer A.

The solvent for use in the present invention preferably has good compatibility with an ion conductive substance such as an ion conductive polymer constituting Layer A of the laminate, a large dielectric constant of 1 or more, a boiling point of 70° C. or higher and a wide electrochemical stability, more preferably an organic solvent. However, depending upon the kind or use of the laminate, the ion conductivity may be improved when water is present, and in this case, water may be used as a solvent. Examples of the organic solvent include oligoethers such as triethylene glycol dimethyl ether and tetraethylene glycol dimethyl ether, carbonates such as ethylene carbonate, propylene carbonate, dimethyl carbonate, diethyl carbonate, vinylene carbonate and (meth)acryloyl carbonate, lactones such as γ-butyrolactone, aromatic nitrites such as benzonitrile and tolunitrile, sulfur- or nitrogen-containing compounds such as dimethylformamide, dimethyl sulfoxide, N-methylpyrrolidone, N-vinylpyrrolidone and sulfolane, phosphate esters, and alcohols such as ethanol, propanol and butanol. Among these, preferred are oligoethers, carbonates and lactones. The above-described solvent includes substances having a function also as a non-polymerizable plasticizer for an ion conductive material.

In general, as the content of the solvent is increased, the ion conductivity of the SPE or PGE in Layer A increases. However, when the solvent content is too large, the mechanical strength of SPE or PGE may be reduced. Also, in general, as the content of the solvent is increased, the viscosity of the ion conductive material or a precursor material thereof in Layer A is reduced (or increased in flowability). Accordingly, several advantages may be realized such that Layer A is formed having a uniform thickness in the production of a laminate or when the laminate is used, the outer layer (Layer B, Layer C or the above-described thin layer) is easily peeled off and removed. However, if the content of the solvent is too large, depending upon the intended laminate, the flowability of the ion conductive material or a precursor material thereof constituting Layer A is increased to the extent that problems may arise such that the uniform thickness of Layer A cannot be maintained or the dimension of the laminate cannot be kept constant. The presence or absence of the solvent or the content of the solvent varies depending upon the kind or use of the laminate of the present invention. However, in general, the content of the solvent in the ion conductive material constituting Layer A is suitably from 0.1 to 10,000 parts by weight, preferably from 1 to 1,000 parts by weight, more preferably from 5 to 500 parts by weight, per 100 parts by weight of the total amount of the ionic substance and the ion conductive substance. Furthermore, when the above-described curable substance, for example, a polymerizable compound such as vinylene carbonate, (meth)acryloyl carbonate or N-vinylpyrrolidone is used as a solvent appropriately in combination with a non-polymerizable solvent and copolymerized with the above-described functional monomer or oligomer, the content of the solvent can be increased and the ion conductivity can be improved without lowering the mechanical strength. Thus, this technique is preferred.

When the ion conductive material for use in the ion conductive laminate of the present invention contains an additive, the additive may include a curing aid such as an initiator, a polymerization catalyst, a chain transfer agent, a curing rate controller, an oxidizing agent, an antioxidant, a stabilizer or others. Additives are freely added to achieve the desired properties of Layer A or the ion conductive substance in Layer A of the laminate of the present invention.

When the ion conductive material for use in the ion conductive laminate of the present invention contains an additive, the amount of the additive varies depending upon the ion conductive substance such as a polymer, the ionic substance such as an electrolyte salt or other components that are mixed therein, and also varies depending upon the use of the laminate. However, for example, the amount of additives in the ion conductive material if present is suitably from 0.0001 to 30 parts by weight, preferably from 0.001 to 10 parts by weight, per 100 parts by weight of the total amount of the ionic substance and the ion conductive substance.

When the ion conductive material for use in the ion conductive laminate of the present invention contains a filler, the filler is a substance that is filled in Layer A so as to achieve full use of desired properties of Layer A or the ion conductive substance in Layer A, to increase mechanical strength of Layer A, to elevate the shape stability of Layer A, or to improve proccessability of Layer A. Examples thereof include thermoplastic resins, thermosetting resins, polymers having rubber elasticity and other organic and inorganic substances, which are added to control strength or flexibility of Layer A, to keep the thickness of Layer A constant, or to improve shape stability. More specifically, for example, in order to obtain a laminate comprising an ultrathin Layer A having a constant thickness of from 1 to 10 $\mu$m or smaller, alumina particles, silica particles, latex particles or non electron-conductive fine particles which do not inhibit ion conduction and are stable in the ion conductive substance, having a particle size corresponding to the thickness of Layer A, may be used by incorporating these particles into Layer A in an amount necessary for controlling the film thickness. Furthermore, in order to obtain a laminate comprising Layer A having a constant homogeneous film thickness of from 1 to 1,000 $\mu$m and having good flexibility, excellent mechanical strength and proccessability, polyethylene nonwoven fabric, polypropylene nonwoven fabric or other porous non electron-conductive polymer matrix materials may be used by incorporating the same into Layer A in an amount as needed.

When the ion conductive material for use in the ion conductive laminate of the present invention contains the above-described filler, the amount of the filler may vary depending upon the ion conductive substance such as an ion conductive polymer, the ionic substance such as an electrolyte salt or other components that are mixed therein, or may vary depending upon the use of the laminate. However, the amount of filler in the ion conductive material if present is suitably from 0.01 to 900 parts by weight, preferably from 0.1 to 300 parts by weight, per 100 parts by weight of the total amount of the ionic substance and the ion conductive substance.

The ion conductive material in the ion conductive laminate of the present invention has a specific resistivity at room temperature (20° C.) of $10^6$ Ω·cm or less in order to provide various elements or electrically conductive materials having excellent capability using the above-described ion conductive substance. The specific resistivity at room temperature is more preferably $10^5$ Ω·cm or less when it is used in electrochemical elements or apparatuses, and more preferably $10^4$ Ω·cm or less in order to produce electrochemical elements or apparatuses having further higher capability. The term "a non ion-conductive material" means a material having an ion conductivity of $10^{-10}$ S/cm or less when measured at 25° C.) by a known AC impedance method (P.

R. Soerensen et al.; *Electrochimica Acta*, Vol. 27, No. 12, pages 1671–1675 (1982)).

In the ion conductive laminate of the present invention, Layer B and Layer C each must have an ion conductivity lower than that of Layer A so as to prevent or reduce as much as possible aging change in conductivity, stability or mechanical properties of the ion conductive material of Layer A. This may result from penetration or diffusion of ionic species undertaking ion conduction in Layer A into Layer B or Layer C in the laminate. In the laminate of the present invention, the ion conductivity of each of Layer B and Layer C is desirably one tenth ($1/10$) or less, preferably one hundredth ($1/100$) or less, and more preferably one thousandth ($1/1,000$) or less, than the ion conductivity of Layer A.

When the ion conductive laminate of the present invention has a thin layer($D_1$ or $D_2$) comprising a metal, a metal oxide or carbon between Layer B and layer A (or between Layer C and Layer A), a Layer B/thin layer $D_1$ (or Layer C/thin layer $D_2$) laminate in the state such that the ion conductivity is lower than that of Layer A, may be provided on Layer A. More specifically, when the thin layer ($D_1$ or $D_2$) has an ion conductivity lower than that of Layer A, the ion conductivity of Layer B located opposite Layer A through the thin layer $D_1$ (or Layer C located opposite Layer A through the thin layer $D_2$) itself may not necessarily be lower than that of Layer A. On the contrary, when the thin layer ($D_1$ or $D_2$) has an ion conductivity higher than that of Layer A, Layer B located opposite Layer A through the thin layer $D_1$ (or Layer C located opposite Layer A through the thin layer or $D_2$) itself may be sufficient if it comprises a material having an ion conductivity lower than that of Layer A. In this context, Layer B and Layer C may include Layer B/thin layer $D_1$ and Layer C/thin layer $D_2$, respectively, as far as the thin layer $D_1$ and $D_2$ has a function in terms of ion conductivity to the extent that Layer B and Layer C in the laminate of the present invention should have been required to have, respectively, if the thin layer $D_1$ and $D_2$ are not present.

A thin layer ($D_1$ or $D_2$) comprising a metal, a metal oxide or carbon provided between Layer B and Layer A (or between Layer C and Layer A) in the ion conductive laminate of the present invention can solve handling or use problems, which may result from the production, storage or use of the laminate depending upon the kind of Layer A, Layer B or Layer C constituting the laminate. Accordingly, the ion conductive material having a thin layer ($D_1$ or $D_2$) comprising a metal, a metal oxide or carbon provided between Layer B and Layer A (or between Layer C and Layer A) is one preferred embodiment of the present invention. The presence of the above-described thin layer is accompanied by various advantageous effects. Namely, the thickness of Layer A can be made homogeneous in constructing the laminate, or the quality, strength, storage stability or handling properties of Layer A may be improved in various electrochemical elements or apparatuses after peeling and without deforming the shape of Layer A upon use, or in handling properties upon use in electrically conductive materials, for example, for preventing electrification.

The constituent material of the thin layer is selected depending on the kind of the laminate and its intended purpose. Examples thereof include metals and alloys such as aluminum, copper, gold, platinum, silver and stainless steel, metal oxides such as indium tin oxide (ITO), alumina and silica, and carbon-base substances such as graphite, diamond and impermeable carbon materials.

In the laminate, when both of Layer B and Layer C are electron conductive materials and when Layer B and Layer C are placed into direct contact with each other or each is connected to another electrically conductive material, for example, when the laminate is bent, a plurality of laminates are piled, or the laminate is connected to an electric conductor (either intentionally or not), an electrical closed circuit is formed between Layer B/Layer A/Layer C in the laminate or between laminates. This causes an unexpected application of voltage to the material constituting Layer A. As a result, a problem of aging deterioration of the laminate tends to arise such that ions of Layer A migrate or the ion conductive material is denatured. Accordingly, at least one of Layer B and Layer C must be a non electron-conductive material. The term "a non electron-conductive material" as used herein means a material which is not electron-conductive. Thus, a non electron-conductive material is either an insulating material, or an ion conductive material having no electron-conductive property. Examples of a material which is electron-conductive is those such as metals, metal alloys, metal-coated materials, electroconductive polymers and electroconductive ceramics as described in U.S. Pat. No. 5,004,657.

In the ion conductive laminate of the present invention, when Layer B, Layer C or a thin layer comprising a metal, a metal oxide or carbon has good wettability to Layer A, the laminate can be advantageous in that Layer B, Layer C or the above-described thin layer is in good contact with Layer A. In particular, in electrochemical apparatuses such as a battery or a capacitor, there is a demand for thinner solid polymer electrolytes having improved thickness accuracy. In this case, Layer B, Layer C or the above-described thin layer having good wettability to Layer A is preferably used. In general, the wettability is higher as the contact angle of the objective liquid to the substrate surface is smaller. Because Layer A of the laminate of the present invention comprises a material which provides good mobility of ionic species within the layer, polyethylene glycol having an average molecular weight of 400 (Mw=380 to 420) was used as a model substance having a polyalkylene oxide chain which is one of the representative substance of materials constituting Layer A to determine the contact angle thereof at 23° C. to various materials used as Layer B, Layer C or the thin layer by a liquid drop method (automatic contact angle meter Model CA-Z, manufactured by Kyowa Kaimen Kagaku KK). Thus, the contact angle, for example, is about 53° to polypropylene (stretched film), about 46° to polyethylene, about 37° to polyethylene terephthalate, about 28° to nylon 6 (stretched film), about 20° to aluminum foil, about 15° to alumina-evaporated polyethylene terephthalate film (alumina surface) and about 8° to silica-evaporated polyethylene terephthalate film (silica surface). When not wetted, the contact angle is obtuse (the contact angle of mercury on glass is about 140°, for example). In the laminate of the present invention, when Layer A is, for example, a thin layer having a homogeneous thickness of from 0.1 to 1,000 $\mu$m (for example, a thickness accuracy within ±30%), any of Layer B, Layer C and the thin layer is preferably a layer comprising a material having a contact angle (measured by the above-described method) to polyethylene glycol of 80° or less. When Layer A, for example, is a thinner layer having a homogeneous thickness (for example, a thickness accuracy within ±20%), any of Layer B, Layer C and the thin layer is more preferably a layer comprising a material having a contact angle of 60° or less. In particular, when Layer A is a very thin layer having a homogeneous thickness of from 0.1 to 50 $\mu$m, any of Layer B, Layer C and the thin layer is particularly preferably a layer comprising a material having a contact angle of 40° or less.

When the laminate of the present invention is used for integrating the ion conductive material constituting Layer A of the ion conductive laminate of the present invention into electrochemical apparatuses such as batteries, capacitors and electrochromic displays, it is preferably used in the production of apparatuses in such manner that at least one of Layer B and Layer C of a laminate consisting of Layer B/Layer A/Layer C is removed by peeling it off from Layer A. Or, in the case where the laminate has a metal, metal oxide or carbon thin layer $D_1$ (or $D_2$) between Layer B (or Layer C) and Layer A, the Layer B (or Layer C)/the thin layer $D_1$ (or $D_2$) is removed by peeling it off from Layer A. Layer A is then placed on an electrode, a separator, an electric conductor or other substrate which is a constituent material of the electrochemical apparatus such as a battery, capacitor and electrochromic material. In this case, the adhesion strength between Layer B and layer A, between Layer A and Layer C or between the thin layer and Layer A is preferably low to the extent that the structure or shape of Layer A is not deformed due to the physical stress caused upon removal of Layer B, Layer C or the thin layer laminated on Layer A by peeling or the like method. Accordingly, when the laminate of the present invention is used according to the above-described method, Layer A preferably has a peel strength such that Layer B, Layer C or the thin layer can be peeled off without substantially deforming the shape of Layer A. In other words, Layer B, Layer C or the thin layer has good releasability (peelability) to the extent that these layers can be peeled off from Layer A without substantially deforming the shape of Layer A.

In general, the releasability is considered to be better as the wettability between the substrate and the layer to be peeled off is lower, and accordingly, as the above-described contact angle is larger. Also, in the present invention, electrochemical apparatuses such as batteries and capacitors are very preferably produced using, as Layer B or Layer C, polypropylene (stretched film) or polyethylene having a large contact angle among the above-described various materials. Polypropylene and polyethylene also exhibit very good releasability from Layer A, by peel-removing Layer B or Layer C from Layer A and then placing Layer A on an electrode, a separator, an electric conductor or other substrate which is a constituent material of the electrochemical apparatus.

On the other hand, it has been found that a thin layer comprising a metal such as aluminum, a metal oxide such as alumina and silica, or carbon, which are considered to have poor releasability due to a smaller contact angle based on the above reasoning, can be unexpectedly peeled off and removed from Layer A without causing any damage of the structure or shape of Layer A. This depends upon the strength of electrolyte Layer A. For example, in the case of Layer A having a tensile strength of 1 kg/cm² or more, then Layer A can be used in the production of electrochemical apparatuses.

The releasability has a reverse interrelationship with the adhesive property which appears to be based on various factors at the interface between a solid and a solid, and cannot be predicted from the wettability alone based on the inter-molecular interaction at the interface between a solid and a liquid as described above. In first laminating Layer A, good wettability is important to achieve homogenization of the surface at the lamination interface. However, when Layer A contains a curable substance or a solvent, Layer A is converted from a flowable material into a substantially solid material after a curing reaction or removal of the solvent to increase the strength of Layer A, or when layer A has from the beginning a strength sufficiently high to endure the peeling, an outer layer even having a small contact angle can be smoothly peeled off. In practice, metals and metal oxides such as aluminum, alumina and silica, having a contact angle smaller than that of nylon 6 and polyethylene terephthalate exhibit not only good wettability to Layer A but also good releasability from Layer A. Hence, these materials are very preferably used in various laminates of the present invention.

When the ion conductive laminate is used in the production of various electrochemical elements or apparatuses or as an electrically conductive material and the outer layers (Layer B or Layer B/thin layer $D_1$ and/or Layer C or thin layer $D_2$/Layer C) provided on the upper and lower parts of Layer A are peeled off and removed before use, the releasability between one outer layer to be peeled off and Layer A must be equal to or greater than, preferably greater than, the releasability between other outer layer and Layer A. Furthermore, when two outer layers are peeled off in sequence before use at a desired step during the production of the above-described elements or apparatuses, the releasability between the outer layer to be peeled off first (hereinafter referred to as the first release outer layer) and Layer A must be equal to or greater than, preferably greater than, the releasability between the outer layer to be peeled off afterward (hereinafter referred to as the second release outer layer) and Layer A.

For example, when a suitable combination of first release outer layer and a second release outer layer is indicated as [xx —YY], examples of the combination include [polypropylene— alumina], [polypropylene—silica], [polypropylene—aluminum], [polypropylene—PET], [polyethylene—alumina], [polyethylene—silica], [polyethylene—aluminum, [polyethylene—PET], [alumina—PET], [silica—PET], [aluminum—PET], [polypropylene—corona discharge-treated polyethylene], [alumina—nylon], [silica—nylon] and [aluminum—nylon]. When the outer layer has the above-described thin layer thereon, the releasability between Layer B/thin layer $D_1$ or thin layer $D_2$/Layer C and Layer A is determined by the releasability between the thin layer and Layer A. Accordingly, although only the thin layer is indicated in the above-described combination examples, the thin layer may be Layer B/thin layer $D_1$ or thin layer $D_2$/Layer C.

As described in the foregoing, when at least one outer layer (Layer B, layer C or the thin layer) is peeled off before use from Layer A of a laminate of the present invention comprising layer A having a homogeneous thickness of from 0.1 to 1,000 μm, the contact angle range capable of achieving both the contact property and the releasability which are generally considered to conflict with each other, is preferably from 5 to 80°, more preferably from 7 to 60°. However, when the strength of Layer A is higher than the peel strength of Layer B, Layer C or the thin layer from Layer A, they can be peeled off without causing any substantial damage to the shape of Layer A. Therefore, the contact angle is not necessarily restricted to the above-described preferred range.

The properties of the ion conductive material such as a SPE and PGE for use in the laminate of the present invention are readily changed, such as the ion conductivity due to water or a polar molecule such as a polar solvent. Accordingly, in the ion conductive laminate of the present invention, in order to prevent aging change in conductivity, stability or mechanical properties of the ion conductive material in Layer A resulting from invasion or elution of liquid (a generic term inclusive of water and a solvent component) such as water or a solvent component passed through Layer B or Layer C to or from the ion conductive material such as a SPE or PGE constituting Layer A, Layer B and Layer C or Layer B and Layer C each having the above-described thin layer thereon are preferably a liquid impermeable layer, more preferably a water impermeable layer. The liquid impermeable layer or water impermeable layer may be sufficient if it comprises a generally well-known liquid impermeable or water impermeable material. When the laminate of the present invention contains a solvent, the liquid impermeable material is not particularly limited as long as it is a liquid impermeable material having resistance against the solvent. Examples thereof include polyolefins such as polyethylene and polypropylene, polyethylene terephthalate, polybutylene terephthalate, saturated polyesters produced from diol and dicarboxylic acid, polycarbonate, polyacetal, polystyrene, polyvinyl chloride, acrylic resin, polyacrylonitrile, ABS resin, AS resin polyamide such as nylon 6 and nylon 6-6, polyphenylene oxide, polyphenylene sulfide, polysulfone, polyethersulfone, polyallylsulfone, polyarylate, polyimide, polyamideimide, fluorocarbon resin, other thermoplastic resins, natural and synthetic rubbers, aluminum, copper, stainless steel, other metals, alloys, metal oxides, glass, phenolic resin, urea resin, melamine resin, epoxy resin, unsaturated polyester resin, silicon resin, thermosetting acrylic resin, diallylphthalate resin, other thermosetting substances having two or more functional groups such as a polymerizable unsaturated bond or a cyclic ring, and thermosetting resin such as a cured product obtained by curing a polymerizable mixture containing the above-described substance. From these, a material suitable for the respective laminates may be selected and used.

Among these substances for constituting Layer B or Layer C, thermoplastic resin can be hot-melted and formed, for example, into a plate, sheet or film having a desired thickness. Therefore, this is practically advantageous in forming Layer B or layer C and is very preferred. When Layer B or Layer C is previously processed into an optional shape (structure) having a predetermined dimension, for example, a plate, a disc, a sheet, or a box or cylinder with a projection or a recession, having a predetermined size and used as Layer B or Layer C constituting the laminate of the present invention or used for a laminate having excellent dimensional stability or strength, when the laminate is used at a relatively high temperature or in an environment where the temperature greatly changes, when the laminate is used in an environment where a considerably strong mechanical stress is applied from the outside, or when Layer B or Layer C is a structure or a constituent part constituting an electrochemical element or apparatus such as a battery, a capacitor or an electrochromic element, which is produced using the laminate of the present invention, so-called engineering plastics having excellent heat resistance or mechanical properties are preferred among the above-described thermoplastic resins. More specifically, engineering plastics such as polyester, polycarbonate, polyacetal, polyamide, polyphenylene oxide, polyphenylene sulfide, polysulfone, polyethersulfone, polyallylsulfone, polyarylate, polyimide, polyamideimide and fluorocarbon resins including polytetrafluoroethylene (PTFE), tetrafluoroethylene/hexafluoropropylene copolymer (FEP), tetrafluoroethylene/perfluoroalkoxyethylene copolymer (PFA) and polyvinylidene fluoride (PVdF) are appropriately used according to the intended use. These thermoplastic resins may be either stretched or unstretched. In addition, inorganic materials such as glass and metal oxide, metals and thermosetting resins are very preferably used. In particular, in order to produce a laminate comprising Layer B or Layer C which comprises a non electron-conductive material and is previously formed into a shape having a predetermined dimension, or to produce a laminate comprising Layer B or Layer C as a non electron-conductive layer having excellent strength, engineering plastics and thermosetting resins are particularly preferred. The engineering plastic which can be suitably used as a material for forming Layer B or Layer C in the laminate of the present invention is a plastic satisfying at least three conditions out of four conditions, namely, (1) a tensile strength of 5.5 kg/mm$^2$ or more, (2) a tensile modulus of elasticity of 200 kg/mm$^2$ or more, (3) a heat distortion temperature of 140° C. or higher at 4.6 kg/cm$^2$ and (4) an Izod notched impact strength of 4 kg·cm/cm or more. Examples of such an engineering plastic include engineering plastics described above and those described in Ken Ihouchi, *Fine Polymer & Engineering Plastics, Kaisetsu to Bussei Hyo* (*Description and Physical Properties Thereof*). "*Engineering Plastic Gaisetsu* (*Introduction*)", pages 175–184, Kagaku Kogyo Nippo Sha (Sep. 30, 1978). However, the present invention is by no means limited thereto.

In producing, using or storing the ion conductive laminate of the present invention, when Layer B and Layer C both comprise a material having a high dielectric constant, dielectric polarization is readily generated in Layer B and Layer C due to an external electric field. Accordingly, when an unexpected electric field is applied from the outside of the laminate, an electrical double layer or dielectric polarization may be generated at the interface between Layer A, which comprises a SPE (or PGE) and is present between Layer B and Layer C, and these outer layers and/or in Layer A. As a result, depending upon the kind or use of the laminate, the quality stability of Layer A may be adversely affected. Accordingly, although this is not restricted only to the laminate of the present invention, at least one of Layer B and Layer C preferably has a low dielectric constant and the dielectric constant (determined according to ASTM D-150; 10$^6$ Hz) of the layer having a lower dielectric constant is preferably 8 or less, more preferably 6 or less. For example, the dielectric constants of the various thermoplastic resins and thermosetting resins described above are: from 2 to 3 for polyolefins such as polyethylene and polypropylene, from 3 to 5 for polyethylene terephthalate, from 3 to 4 for polybutylene terephthalate, from 2.8 to 3.5 for polycarbonate, from 3 to 4 for polyacetal, from 2 to 4 for polystyrene, from 2 to 5 for polyvinyl chloride, from 2 to 3 for acrylic resin, from 2 to 5 for polyacrylonitrile and ABS resin, about 3 for AS resin, from 2 to 8 for nylon 6, approximately from 3 to 6 for nylon 6-6, from 2.5 to 3.5 for polyphenylene oxide, from 3 to 5 for polyphenylene sulfide, from 3 to 4 for polysulfone, from 3 to 4 for polyethersulfone, from 3 to 4 for polyarylate, from 3 to 4 for polyimide, from 3 to 4 for polyamideimide, from 2 to 3 for PTFE, from 6 to 8 for PVdF, from 2 to 3 for silicone rubber and silicone resin, from 4 to 6 for phenol resin, from 3 to 6 for epoxy resin, from 3 to 6 for diallylphthalate resin and from 3 to 8 for unsaturated polyester resin.

In the ion conductive laminate of the present invention, when Layer A comprises a material containing a curable substance, the laminate may be heated as is, or Layer A may be cured by heating and/or irradiating with active light after removing by peeling or the like at least one of Layer B and Layer C. Or, if the above-described thin layer is formed thereon, at least one of Layer B/thin layer $D_1$ and Layer C/thin layer $D_2$ are removed to obtain Layer A comprising an ion conductive SPE or PGE. However, in order to cure Layer A by heating and/or irradiating with active light without removing by peeling or the like Layer B or Layer C from the laminate to obtain Layer A comprising an ion conductive SPE or PGE, at least one of Layer B and Layer C is preferably a layer comprising a light transmissible material.

When the laminate of the present invention is a constituent part of an electrochemical element or apparatus such as a photoelectric cell, a solar cell or an electrochromic display, at least one of Layer B and Layer C is also preferably a layer comprising a light transmissible material. "Light transmissible" means that the light transmissible layer of a laminate has a transmissibility to active light having a specific wavelength (far infrared light, near infrared light, visible light, ultraviolet light, electron beam, γ beam or X ray). The above-described light passes through the light transmissible layer of the laminate and reaches Layer A or the lower part thereof, or when the laminate is used for a light-emitting element or coloring element, the emission or coloration passes through the light transmissible layer to reach the outside and the emission or coloration can be confirmed from outside the laminate. The material constituting the light transmissible layer may be selected from substances having the above-described transmissibility to the objective active light, among the various materials described above.

With respect to transmissibility to active light, the transmission wavelength required varies depending upon the kind of active light that is used. For example, in the case of a laminate having, as a constituent element, Layer A containing the above-described curable substance, when ultraviolet ray is used for the curing, the transmittance at a wavelength of from 250 to 400 nm is suitably 1% or more, more preferably 10% or more. When visible light is used, the transmittance at a wavelength of from 400 to 740 nm is suitably 1% or more, more preferably 10% or more, and when near infrared light is used, the transmittance at a wavelength of from 740 to 1,500 nm is suitably 1% or more, more preferably 10% or more. When electron beams are used, the wavelength of the electron beams depends upon the electric field energy that is generated. The wavelength can usually be expressed by: $\lambda(nm)=(1.2)/(E\ (eV)\ )^{1/2}$, and the wavelength at 10 KeV is usually about 0.01 nm. Accordingly, although the kind of the material used is not particularly limited, the transmission is facilitated if the material is as thin as possible. The thickness is suitably 10 $\mu m$ or less, preferably 1 $\mu m$ or less. The polymer is generally sensitive to electron beams, and hydrocarbon-base polymers containing no hetero atom are preferred. Polyolefins such as polyethylene and polypropylene are more preferred as a cover film (Layer B or Layer C).

On the other hand, consider the case where layer A of the laminate of the present invention comprises a material that is not stable to a specific active light, for example, where Layer A contains a curable substance sensitive to active light. When Layer A is cured after removing (by peeling or the like) Layer B or layer C and then used, or if the above-described thin layer is formed thereon, when Layer A is cured after removing at least one of Layer B/thin layer $D_1$ and Layer C/thin layer $D_2$ and then used, none of two outer layers selected from Layer B, Layer C, Layer B/thin layer $D_1$ and layer C/thin layer $D_2$ are preferably light transmissible. In this manner, the storage stability of the laminate prior to use and the quality of the material constituting layer A in the laminate can be maintained. The term "not light-transmissible" to active light as used herein means that the transmittance to an objective specific active light is suitably less than 1%, more preferably 0.1% or less, still more preferably 0.01% or less.

In general, the transmittance is in inverse proportion to the film thickness. Accordingly, even if the outer layer comprises the same substance, the transmittance can be reduced to the above-mentioned preferred range by increasing the film thickness. Or, the outer layer may be rendered non light-transmissible by appropriately blending therein known substances capable of absorbing or reflecting the objective active light.

Furthermore, in order to maintain the quality of Layer A, both of two outer layers of the laminate selected from Layer B, Layer C, Layer B/thin layer $D_1$ and Layer C/thin layer $D_2$ are preferably gas impermeable. Thus, penetration of moisture, an active gas such as oxygen, carbon dioxide, sulfur dioxide or nitrogen oxide, or other gas molecules effecting the quality of Layer A, which is present in the atmosphere where the laminate is placed, can be prevented from passing through Layer B, Layer C or the thin layer into Layer A.

For example, when Layer A of the laminate is an ion conductive material containing the above-described curable substance or a precursor material thereof, a curing reaction may result upon heating and/or irradiating the laminate with active light. Thus, it is important to prevent gases such as oxygen, which inhibit initiation or progress of the curing reaction, from penetrating into Layer A of the laminate.

With respect to the material constituting the gas impermeable layer, known gas barrier resins, various thermoplastic resins and thermosetting resins described above with respect to the water impermeable or liquid impermeable material, known water unabsorbable or water low absorptive resin may be used as the gas impermeable outer layer of the laminate of the present invention. Furthermore, the material may be selected from metals, alloys, metal oxides, glass and carbon, which do not react with the gas and are gas impermeable.

The water absorption and gas permeability of various resins are described in many known publications. For example, *Plastic Dokuhon* (*Handbook*), 18th rev., Plastic Age KK (1992) describes various useful resins. For example, the water absorption (24 hr; ⅛") of various plastics are: from 0.3 to 0.5 for melamin resin, from 0.1 to 0.2 for phenol resin (without filler), from 0.01 to 1.0 for unsaturated polyester (with glass fiber), from 0.4 to 0.8 for urea resin, from 0.08 to 0.15 for epoxy resin, from 0.07 to 0.4 for vinyl chloride resin (hard), from 0.5 to 1.0 for vinyl chloride resin (soft), from 0.12 to 0.25 for polyacetal, from 0.3 to 0.4 for methacrylic resin, from 2.0 to 4.5 for acetyl cellulose, 1.6 for nylon 6 (polyamide), less than 0.01 for polyethylene, less than 0.01 for polypropylene, 0.00 for polytetrafluoroethylene, from 0.03 to 0.05 for polystyrene and 0.15 for polycarbonate. Furthermore, the gas permeability (thickness: 25 $\mu m$, 20° C., 65% RH) of various films to carbon dioxide, oxygen or nitrogen are: [described in the order of $CO_2/O_2/N_2$, unit: $cc/m^2 \cdot atm \cdot 24\ hr$] [18,500/4,000/1,400] for polyethylene (low density), [3,000/600/220] for polyethylene (high density), [3,800/860/200] for polypropylene (unstretched), [1,680/550/100] for polypropylene (biaxially stretched) (OPP), [420/60/25] for polyester (polyethylene terephthalate), [253/60/16] for nylon 6 (unstretched), [79/20/6] for nylon 6 [biaxially stretched], [2,400/5,000/800] for polystyrene, [1,225/200/35] for polycarbonate, [442/150/56] for polyvinyl chloride (hard), [70/<115/2.2] for polyvinylidene chloride, [–/70/–] for MST cellophane (vinyl chloride-base), [–/20/–] for K cellophane (vinylidene chloride-base), [10/7/–] for polyvinyl alcohol, [–/2/–] for ethylene-vinyl alcohol copolymer (EVOH) and [15/5 to 10/1.5] for polyvinylidene chloride-coated OPP.

Among these resins, when the ion conductive material constituting Layer A of the laminate of the present invention is used for applications requiring extreme performance, polybutylene terephthalate, polyethylene terephthalate, ethylene-vinyl alcohol copolymer (EVOH), polycarbonate, polyamide (e.g., nylon 6), polyacrylonitrile resin, which have a very low oxygen permeability, stretched polypropylene, high-density polyethylene, polypropylene, which have low permeability, and various other resins such as polyethylene are preferred. In this regard, the front or back surface is laminated with a gas barrier thin film against the objective gas by a known method, or is subjected to surface treatment to improve the gas barrier property. However, as long as the performance requirements are satisfied, low-density polyethylene or polystyrene inferior to the above-described resins in gas barrier property, for example, against oxygen, may be used depending upon the intended use of the laminate.

Of the various materials described above, materials having a low moisture permeability are preferably used as a material constituting Layer B or Layer C. This is because it is important to prevent an increase in the water content of Layer A in view of quality and use of the laminate of the present invention.

TABLE 1

Moisture Permeability of Various Resins

| Resin (film) | Moisture permeability $(g/m^2 \cdot 24\ hr)$ 40° C., 90% RH |
|---|---|
| Polyethylene (low-density) | 20 |
| Polyethylene (high-density) | 10 |
| Polypropylene (unstretched) | 11 |
| Polypropylene (biaxially stretched) (OPP) | 6 |
| Polyethylene terephthalate | 27 |
| Nylon 6 (unstretched) | 300 |
| Nylon 6 (biaxially stretched) | 145 |
| Polystyrene | 160 |
| Polycarbonate | 80 |
| Polyvinyl chloride (hard) | 40 |
| Polyvinylidene chloride | 1.5 to 5 |
| MST Cellophane (vinyl chloride-base) | 50 |
| K Cellophane (vinylidene chloride-base) | 10 |
| Ethylene-vinyl alcohol copolymer (EVOH) | 50 |
| Polyvinylidene chloride-coated OPP | 4 to 5 |

Among the above-described thermoplastic resins, for example the moisture permeability of various resin are known as shown in Table 1 (see, Kogyo Zairyo (Industrial Materials), 39, [8], 38 (1990)). Layer B or Layer C of the laminate of the present invention is more preferably a material selected from thermoplastic resins, thermosetting resins, metals, alloys, metal oxides, glass and carbon, and having a moisture permeability of 200 $g/m^2 \cdot 24$ hr (40° C., 90% RH) or less, still more preferably a material having a moisture permeability of 100 $g/m^2 \cdot 24$ hr or less.

When Layer B, Layer C or the thin layer as an outer layer of the laminate of the present invention is a layer comprising an electron conductive material and when the laminate is used in producing an electrochemical element or apparatus or a constituent part thereof, it is advantageous in view of the production process of the element, apparatus or a constituent part thereof to use a laminate where a lead wire or current collecting body comprising an electron conductive electric conductor such as gold, platinum, copper or stainless steel is connected to at least one of these outer layers. A laminate where at least one of electron conductive Layer B, Layer C and thin layer is connected to an electron conductive electric conductor is a very preferred embodiment of the laminate of the present invention.

It is also advantageous in view of the production process of the above-described element or apparatus or a constituent part thereof that the above-described laminate comprising at least one outer layer connected to an electron conductive electric conductor, which is one embodiment of the laminate comprising an outer layer connected to an electron conductive electric conductor, is a laminate where a lead wire or current collecting body comprising an electron conductive electric conductor such as gold, platinum, copper or stainless steel is connected to Layer A but is not in contact with the above-described outer layer connected to an electron conductive electric conductor. Thus, a laminate comprising an outer layer and Layer A each connected to an electron conductive electric conductor is a very preferred embodiment of the laminate of the present invention.

Furthermore, when the laminate is used in the production of an electrochemical element or apparatus or a constituent part thereof comprising Layer A of the laminate of the present invention as an electrolyte layer and any one of Layer B, Layer C or the above-described thin layer as a constituent part, the use of a laminate where a lead wire or current collecting body comprising an electron conductive electric conductor such as gold, platinum copper or stainless steel is previously connected to two different sites of Layer A is advantageous in the production process of the above-described element, apparatus or constituent part thereof. Thus, a laminate where electron conductive electric conductors are connected to two different sites of Layer A is a very preferred embodiment of the laminate of the present invention. In this case, two electron conductive electric conductors may be connected to both sides of Layer A from a direction which is parallel to the layer direction of the laminate, one electric conductor may be connected from a direction which is parallel to the layer direction and the other electric conductor may be connected by passing through an outer layer of the laminate, two electric conductors both may pass through either one of the upper and lower outer layers of the laminate, or one electric conductor may pass through from the upper portion and the other from the lower portion.

The thickness of Layer A comprising an ion conductive material in the ion conductive laminate of the present invention varies depending upon the intended application and is not particularly limited. However, when Layer A is used in various elements, apparatuses or electric conductor materials described above, it is suitably from 0.1 to 1,000 μm. In particular, when Layer A is used in a thin electrochemical element or electrochemical apparatus such as batteries, capacitors and electrochromic elements, the thickness is preferably as small as possible. For example, the thickness is more preferably from 0.1 to 300 μm, still more preferably from 0.1 to 50 μm. However, depending upon the use, the thickness of Layer A may largely exceed 1,000 μm.

The thicknesses of Layer B and Layer C of the laminate of the present invention vary depending upon the intended application and are not particularly limited. These thicknesses may be appropriately determined according to the kind or intended use of the laminate or depending upon the combination with Layer A. Even in the case of a laminate where the thickness of Layer A is from 0.1 to 1,000 μm, the thicknesses of Layer B and Layer C are not particularly limited. However, the thicknesses of Layer B and Layer C each is independently preferably, for example, from 1 to 5,000 μm. When the laminate of the present invention is used in an electrochemical apparatus or electric conductor material or in the production thereof and when Layer B or Layer C is used to maintain the mechanical strength, the thickness of Layer B or Layer C may be, for example, several mm greatly exceeding 5,000 μm. Of course, Layer B, Layer C or the thin layer present between Layer B or Layer C and Layer A may serve as an electrode of an electrochemical element or an apparatus produced using the laminate of the present invention.

When the laminate of the present invention comprises the above-described thin layer between Layer A and Layer B and/or Layer C, the thickness of the thin layer is not particularly limited and can be appropriately selected according to the kind or intended use of the laminate, or depending upon the combination with Layer A, Layer B or Layer C before providing the thin layer in the laminate. Even when the thin layer is present in the laminate where the thickness of Layer A is from 0.1 to 1,000 μm, the thickness of the thin film layer is not particularly limited. However, it is suitably from 50 to 5,000 μm, preferably from 50 to 200 μm.

The thickness of the laminate of the present invention is a total of thicknesses of the respective layers depending upon the intended use and may be determined according to the optional selection of layers. It may range from several μm to several mm, or may exceed this range. Further, the size and the length of the laminate can also be freely determined. The size may range from several mm$^2$ to several hundred mm$^2$, or may exceed or fall below this range. The length also may range from several mm to several hundred mm, or may exceed or fall below this range.

FIGS. 1 to 8 each shows a schematical cross section of the laminate of the present invention. Respective edge parts in the direction parallel to the layer of the laminate of the present invention may have any form according to the intended use of the laminate. For example, Layer B (or Layer C) itself may be laminated to cover the other outer layer, namely, layer C (or Layer B). Furthermore, Layer B and Layer C may be the same layer, for example, in a bag form; one edge, both edge parts or the peripheral part of the laminate may be sealed with an optionally selected sealant or adhesive which does not adversely affect the quality of the laminate constructed, and comprises a material such as a thermoplastic resin, rubber or thermosetting resin (e.g., epoxy resin); or when the outer layers (Layer B and Layer C) each comprises a thermoplastic resin, two outer layers may be bonded, for example, by heat sealing, so as to lay one edge, both edge parts or the peripheral part of the laminate in an unopen state, which is preferred for achieving easy handling during the production, use or storage of the laminate, particularly for preventing direct contact of Layer A of the laminate with the outer atmosphere. The laminate of the present invention includes, as a laminate where a plurality of Layers A are laminated, for example, a laminate where Layer B serves also as Layer C, a laminate comprising a plurality of Layer B/Layer A laminates with Layer B being laminated on Layer A (e.g., Layer B/Layer A/Layer B/Layer A laminate) and a laminate comprising a plurality of laminates consisting of Layer B/thin layer $D_1$/Layer A wherein the above-mentioned thin layer $D_1$ is laminated on Layer A and Layer B is laminated thereon (e.g., layer B/thin layer $D_1$/Layer A/Layer B/thin layer $D_1$/Layer A laminate). Furthermore, a rolled laminate obtained by rolling the above-described laminate is also a laminate structure where Layers A are laminated on two outer layers and included in the laminate of the present invention. In this case, one edge or both edges (coiled surface) of the roll is(are) preferably treated according to a suitable method so as to provide a laminate where Layer A contained in the laminate is placed in a state which is out of direct contact with the outer atmosphere. Furthermore, even when the laminate has a thin layer between Layer A and outer Layer B or outer Layer C, one edge, both edge parts or the peripheral part of the laminate is(are) preferably treated to be in an unopen state.

However, even when the laminate of the present invention is in a form where the edge part is unclosed, if the laminate is placed and handled in a closed container so as to keep the laminate out of contact with an outer atmosphere or in an atmosphere which does not adversely affect the laminate, particularly the quality of Layer A, the edge part of the laminate need not be treated to be in a closed state.

The water content of the ion conductive material constituting Layer A of the ion conductive laminate of the present invention varies depending upon the intended use and is not particularly limited, however, in some uses, the water content is preferably low. For example, when used in an electrochemical element or apparatus such as a lithium battery, lithium ion battery, non-aqueous electrical double layer capacitor or non-aqueous electrochromic element, it is preferably 1,000 ppm or less, more preferably 200 ppm or less.

The ion conductive laminate of the present invention can be produced by various methods. A suitable method may be freely selected according to the kind of the laminate to be produced. In general, for example, the laminate of the present invention described in any one of embodiments (1) to (26) above is produced by (i) forming Layer A comprising an ion conductive material on Layer B having an ion conductivity lower than that of Layer A in such manner that the material of Layer A substantially does not flow or move on Layer B to provide a laminate structure consisting of Layer B/Layer A, (ii) laminating on Layer A Layer C comprising a material having an ion conductivity lower than that of Layer A to provide a laminate structure consisting of Layer B/Layer A/Layer C, and then (iii) applying pressure to the laminate structure with a force applied on the Layer B side surface of the laminate structure and a force in opposition thereto applied on the Layer C side surface of the laminate structure.

In the above step (i), the laminate structure consisting of Layer B/Layer A may be formed by a method where Layer A is previously shaped into a layer form such as a film or sheet and then placed on Layer B, a method where Layer A is formed by applying the ion conductive material constituting Layer A as it is or after appropriately diluting the same with a solvent on Layer B according to, for example, a spray method, a coating method, a dipping method, a spin coating method or another optional method, or a method where a layer comprising precursor materials of Layer A is first formed by applying precursor materials of Layer A (for example, a curable substance, additives, a solvent, or a material containing a monomer or an oligomer or the like as a precursor of the ion conductive polymer which is a precursor of the ion conductive material) on Layer B according to a spray method, a coating method, a dip method, a spin coating method or another optional method and then the layer comprising the precursor materials of Layer A is converted into the objective Layer A by polymerization, curing or removal of solvent. In step (i), the material of Layer A includes precursor materials of Layer A and "in such manner that the material of Layer A substantially does not flow or move on Layer B" includes not only the case where the material of Layer A is substantially a solid material but also the case where the material of Layer A is, even if it is a flowable liquid, placed or being placed on Layer B in such manner that the material substantially does not flow or move on Layer B. For example, the liquid material of Layer A placed on Layer B constituting a horizontal surface is in a state such that it does not move or flow under gravity at least until it is processed in the next step. More specifically, the case where the thickness of Layer A comprising the material of Layer A is small to the extent that it does not flow or move on Layer B constituting a horizontal surface, comes under the above defined state. Also, the case where the material of Layer A is, even if it is a flowable liquid (low viscosity liquid) unable to maintain a desired thickness by itself, poured, for example, into a frame spacer having a desired thickness placed on Layer B to give Layer A the desired thickness, comes under the above defined state.

In the above step (ii), Layer C is laminated on Layer A to provide a laminate structure consisting of Layer B/Layer A/Layer C. In this step, Layer C is laminated on Layer A of the laminate structure consisting of Layer B/Layer A produced in step (i) as it is or when the material of Layer A is a precursor material of the ion conductive material for Layer A, after converting the layer comprising the precursor material of Layer A by polymerization, curing or removal of solvent into the objective Layer A. In laminating Layer C, a method of previously shaping Layer C into a layer form such as a film or sheet and then placing it on Layer A, a method of applying the material constituting Layer C as it is or after appropriately diluting it with a solvent on Layer A, for example, by a spray method, a coating method, a dip method, a spin coating method or another optional method to form Layer C on layer A, or a method of applying a precursor material of Layer C (e.g., monomer, oligomer), for example, by a spray method, a coating method, a dip method, a spin coating method or another optional method to form a layer comprising the precursor material of Layer C on Layer A and then converting the layer comprising the precursor material of Layer C into the objective layer C by polymerization, curing or removal of solvent to form a laminate structure consisting of Layer B/Layer A/Layer C.

In the production of a laminate consisting of Layer B/Layer A/Layer C of the present invention, in step (iii), the laminate structure consisting of Layer B/Layer A/Layer C is pressed by applying a force on the Layer B side surface of the laminate structure and a force in opposition thereto on the Layer C side surface so as to adjust the thickness of layers constituting the laminate to a desired thickness or to achieve homogenization. The pressure is applied after step (i) and step (ii) to press the laminate structure consisting of layer B/Layer A/Layer C by imposing a force on the Layer B side surface of the laminate structure and a force in opposition thereto on the Layer C side surface. In this case, any pressing method may be used. For example, the laminate may be pressed according to a roller pressing method by passing the laminate through nip rolls or other optional pressure rolls, or according to a compression molding method where presses having provided thereon, if desired, a spacer or die having a desired thickness are pressed with a prescribed pressure on the laminate from upside and downside such that the laminate is interposed between spacers or within the mold. The pressing pressure varies depending upon the kind of the laminate. However, a pressure capable of performing laminate molding may usually be used. A high pressure of from 50 to 300 kgf/cm$^2$ that is used, for example, in high-pressure laminating may be used depending on the intended application. However, in the case of the laminate of the present invention, a pressure lower than the above-described range, specifically a pressure of 50 kgf/cm$^2$ or less as used in so-called low-pressure laminating is preferred. In particular, in producing a laminate which is placed into use after removing outer layers from the laminate, as long as the pressure is of a degree such that the thickness of Layer A of the laminate structure consisting of Layer B/Layer A/Layer C can be homogenized, the pressing pressure is preferably as low as possible in practice.

When the pressing as described above with respect to step (iii) is performed simultaneously with step (i) or (ii), step (iii) may be included in step (i) or (ii), and this technique is also included in the above-described production method of the present invention. More specifically, in step (i) and/or (ii), a layer to be laminated or a layer comprising a precursor material thereof is placed on another layer to provide a laminate structure or formed, for example, by a spray method, a coating method, a dip method, a spin coating method or another optional method to form a laminate structure. Then, the laminate structure is pressed according to a roller pressing method of passing the laminate through nip rolls or other optional pressure rolls or according to a compression molding method of pressing with a prescribed pressure from upside and downside of the laminate structure with presses having provided thereon, if desired, a spacer or a die having a desired thickness such that the laminate is interposed between spacers or within the die, thereby laminating respective layers of each laminate structure formed. The pressure in pressing may be freely selected as described in the above step (iii) depending upon the kind of the laminate. However, when pressing is performed in step (i), it may be performed under a pressure used in low-pressure laminating such that the thickness of layer A of the laminate structure can be homogenized and the pressure is preferably as low as possible in practice. When pressing is performed in step (ii), the pressure may vary depending upon the laminate. However, a pressure capable of performing laminate molding is usually used. A high pressure of from 50 to 300 kgf/cm$^2$ that is used, for example, in the case of high-pressure laminating may be used according to the intended application. However, in the case of the laminate of the present invention, a pressure lower than the above-described range, specifically a pressure of 50 kgf/cm$^2$ or less as used in low-pressure laminating is preferred. In particular, in producing a laminate which is used after removing outer layers from the laminate, as long as the pressure is of a degree such that the thickness of Layer A of the laminate structure consisting of Layer B/Layer A/Layer C is homogenized, it is preferably as low as possible in practice.

In the method of the present invention for producing a laminate having a thin layer ($D_1$ or $D_2$) comprising a metal, a metal oxide or carbon on at least one surface of Layer B or Layer C, the thin layer ($D_1$ or $D_2$) is previously formed on Layer B or Layer C by an optional method, and then Layer B or Layer C having the thin layer ($D_1$ or $D_2$) may be subjected to the above-mentioned steps (i), (ii) and (iii) to produce the objective laminate.

In the method for previously laminating the thin layer ($D_1$ or $D_2$) on Layer B or Layer C, lamination can be performed by placing the thin layer which is previously formed on Layer B or Layer C and, if desired, by roller pressing or compression pressing the layers. Or, on Layer B or Layer C, a layer comprising a material constituting the thin layer or a precursor material of the thin layer is formed, for example, by a spray method, a coating method, a dip method, a spin coating method, an evaporation (vapor deposition) method or another optional method to provide layer B or Layer C having laminated thereon the thin layer, or a layer comprising a precursor material of the thin layer is converted into the objective thin layer by polymerization, curing or removal of solvent to thereby form Layer B or Layer C having laminated thereon the thin layer ($D_1$ or $D_2$).

Furthermore, before laminating Layer C on Layer A in the above-mentioned step (ii), the thin layer which is previously formed may be laminated on Layer A, and Layer C is laminated thereon to produce a laminate of the present invention having the thin layer ($D_1$ or $D_2$) between Layer C and Layer A.

In the above-described methods, when a layer comprising a precursor material containing a curable substance for forming Layer A is converted into Layer A, the layer comprising a precursor material of Layer A may be cured by heating and/or irradiating with active light after step (i) to convert the layer into Layer A, and then Layer C is laminated on Layer A to provide a laminate structure consisting of Layer B/Layer A/Layer C. Or, a laminate structure consisting of Layer B/Layer A precursor material layer/Layer C may be formed through steps (i) and (ii), and then the layer comprising the precursor material of Layer A may be cured by heating and/or irradiating with active light to convert the layer into Layer A to thereby provide a laminate structure consisting of Layer B/Layer A/Layer C. Alternatively, the layer comprising a precursor material of Layer A may be cured in the same manner as described above at the pressurization step (iii) after steps (i) and (ii) to convert the layer into Layer A.

In the above-described methods, when Layer B, Layer C or a layer for forming the thin layer, comprising a precursor material for forming Layer B, Layer C or the thin layer, is converted into the objective Layer B, Layer C or the thin layer, the layer comprising the precursor material may be cured by heating and/or irradiating with active light after step (i), and/or steps (i) and (ii) to convert the layer into the objective layer.

In this case, the curing may be performed by polymerizing the curable substance by heating and/or irradiating with active light. The polymerization may be performed by a general method using polymerizability of the polymerizable functional group of the polymerizable compound in the curable material. For example, a general method using polymerizability of an acryloyl group or the methacryloyl group in a polymerizable compound having an acryloyl group or a methacryloyl group may be used. More specifically, the polymerizable compound or a mixture of the polymerizable compound with other polymerizable compounds capable of copolymerization described above may be subjected to radical polymerization by heating or irradiating with active light, cationic polymerization or anionic polymerization, using a radical thermal polymerization initiator such as azobisisobutyronitrile and benzoyl peroxide, a radial photopolymerization initiator such as benzyl methyl ketal and benzophenone, a cationic polymerization catalyst such as a protonic acid (e.g., $CF_3COOH$) and a Lewis acid (e.g., $BF_3$, $AlCl_3$), or an anionic polymerization catalyst such as butyl lithium, sodium naphthalene and lithium alkoxide.

In the above-described production method, when Layer A is Layer A comprising an ion conductive material containing a solvent or a layer comprising a precursor material of Layer A containing a solvent, the laminate may also be produced through the above-mentioned steps (i), (ii) and (iii). A laminate structure consisting of Layer B/Layer A having a solid or substantially solid Layer A as a constituent layer may be produced by removing, if necessary, a desired amount of solvent from Layer A or the layer comprising a precursor material of Layer A, or a laminate containing a considerable amount of solvent capable of various uses may also be produced.

The laminate described in any one of embodiments (1) to (29) above of the present invention may also be produced by the following method which is a practical embodiment of the above-described method. A Layer A/Layer C laminate or Layer B/Layer A laminate is produced through a step of removing at least one of Layer B and Layer C from Layer A of the laminate described in any one of embodiments (1) to (29) or a step of removing Layer B or Layer C having on the surface thereof facing Layer A a thin layer comprising a metal, a metal oxide or carbon, together with the thin layer from Layer A, to produce a Layer A/Layer C or Layer B/Layer A laminate, and a step of laminating the laminate produced above on a Layer A/Layer C or Layer B/Layer A laminate produced in the same manner such that Layers A of respective laminates are bonded together, to provide a Layer B/Layer A/Layer C, Layer B/Layer A/Layer B or Layer C/Layer A/Layer C laminate structure as a new laminate. Or, in the same manner, various electrochemical elements or apparatuses having a Layer B/Layer A/Layer C, Layer B/Layer A/Layer B or Layer C/Layer A/Layer C laminate structure can be produced.

The ion conductive laminate of the present invention is suitably used in various batteries, capacitors, electrochromic elements, apparatuses thereof and other electrochemical elements and apparatuses. In this case, it is advantageous to use Layer A, which becomes a surface layer after removing at least one of Layer B and Layer C from Layer A of the laminate of the present invention described in any one of embodiments (1) to (29) above or after removing Layer B or Layer C having on the surface thereof facing Layer A a thin layer ($D_1$ or $D_2$) comprising a metal, a metal oxide or carbon, together with the thin layer ($D_1$ or $D_2$) from Layer A, in the production of the above-described electrochemical elements and apparatuses. An electrochemical element or apparatus can be produced through a step of forming a layer comprising a material containing, for example, when a battery is constructed, an electrochemically active substance (positive and/or negative electroactive substance), on at least one removal surface of Layer A as the surface layer.

According to the above-described method, batteries, capacitors, electrochemical power generating elements and apparatuses such as a photoelectric cell and a solar cell, electrochemical coloring elements and apparatuses such as an electrochromic element and apparatus, and electrochemical light-emitting elements and apparatuses using an electroluminescence material can be produced.

One example of the method for producing a secondary battery using the laminate of the present invention is described in detail below.

When a battery is produced using the ion conductive laminate of the present invention, the battery preferably has a construction such that the negative electrode comprises an electroactive substance (negative electroactive substance) using as a carrier an alkali metal ion such as an alkali metal, an alkali metal alloy or a carbon material. Also, the negative electroactive substance has a low oxidation-reduction potential such that a battery of high voltage and high capacity can be obtained. Among these electroactive substances, especially preferred are lithium metal and lithium alloys such as a lithium/aluminum alloy, a lithium/lead alloy and a lithium/antimony alloy because of their low oxidation-reduction potential. The carbon material is also especially preferred in that when it occludes Li ions, a low oxidation-reduction potential is provided and moreover, the material is stable and safe. Examples of the carbon material capable of occluding and releasing Li ions include natural graphite, artificial graphite, vapor phase process graphite, petroleum coke, coal coke, pitch-base carbon, polyacene and furalenes such as $C_{60}$ and $C_{70}$.

The positive electrode preferably comprises an electroactive substance (positive electroactive substance) having a high oxidation-reduction potential such as a metal oxide, a metal sulfide, an electroconductive polymer or a carbon material, so that a battery of high voltage and high capacity can be obtained. Among these electroactive substances, preferred in view of high filling density and high volume capacity density are metal oxides such as cobalt oxide, manganese oxide, vanadium oxide, nickel oxide and molybdenum oxide, and metal sulfides such as molybdenum sulfide, titanium sulfide and vanadium sulfide, and particularly preferred in view of high capacity and high voltage are manganese oxide, nickel oxide and cobalt oxide.

The production method of these metal oxides and metal sulfides is not particularly limited. They may be produced, for example, by a general electrolytic or heating process as described in *Denkikagaku* (*Electrochemistry*), Vol. 22, page 574 (1954). When they are used in a lithium battery as an electroactive substance, in the production of the battery, the substance is preferably used in a state such that a Li element is inserted (compounded) into a metal oxide or a metal sulfide, for example, in the form of $Li_xCoO_2$ or $Li_xMnO_2$. The insertion method of the Li element is not particularly limited and for example, a method of electrochemically inserting Li ions or a method of mixing a salt such as $Li_2CO_3$ with a metal oxide and subjecting the mixture to heat treatment as described in U.S. Pat. No. 4,357,215 may be used.

In view of flexibility and easy formability into a thin film, electroconductive polymers are preferred as the positive electrode material. Examples of the electroconductive polymer include polyaniline, polyacetylene and a derivative thereof, polyparaphenylene and a derivative thereof, polypyrrolylene and a derivative thereof, polythienylene and a derivative thereof, polypyridinediyl and a derivative thereof, polyisothianaphthenylene and a derivative thereof, polyfurylene and a derivative thereof, polyselenophene and a derivative thereof, and polyarylene vinylene and a derivative thereof such as polyparaphenylene vinylene, polythienylene vinylene, polyfurylene vinylene, polynaphthenylene vinylene, polyselenophene vinylene and polypyridinediyl vinylene. Among these, especially preferred are polymers of an aniline derivative soluble in an organic solvent. The above-described electroconductive polymers for use as an electroactive substance in a battery or in an electrode can be produced according to a chemical, electrochemical or other known method.

With respect to other organic materials, disulfide compounds such as 2,5-dimercapto-1,3,4-thiadiazole and mixtures of the compound with an electroconductive polymer are preferred because of their high capacity.

Examples of the carbon material include natural graphite, artificial graphite, vapor phase process graphite, petroleum coke, coal coke, fluorinated graphite, pitch-base carbon and polyacene.

Also, the carbon material for use as an electroactive substance in the battery or electrode of the present invention may be a commercially available product or may be produced according to a known method.

When the laminate of the present invention is used in the production of a battery, the kind of electrolyte salt as an ionic substance contained in the ion conductive material (SPE or PGE) constituting Layer A and used for compounding the material is not particularly limited and any electrolyte salts containing an ion intended to be a charge carrier may be used. However, those having a large dissociation constant in a SPE or PGE are preferred. Specifically, alkali metal salts, quaternary ammonium salts such as $(CH_3)_4NBF_4$, quaternary phosphonium salts such as $(CH_3)_4PBF_4$, transition metal salts such as $AgClO_4$, and protonic acids such as hydrochloric acid, perchloric acid and borofluoric acid are preferred.

The negative electroactive substance for use in the battery of the present invention, as described above, preferably uses as a carrier an alkali metal ion such as an alkali metal, an alkali metal alloy or a carbon material and has a low oxidation-reduction potential, so that a battery of high voltage and high capacity can be obtained. Accordingly, the electrolyte in the SPE or PGE for use in a battery using the above-described negative electrode with an alkali metal ion as a carrier is preferably an alkali metal salt. Examples of the alkali metal salt include $LiCF_3SO_3$, $LiPF_6$, $LiClO_4$, $LiI$, $LiBF_4$, $LiSCN$, $LiAsF_6$, $LiN(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$. Among these, lithium or a lithium alloy is most preferably used as the alkali metal because of high voltage, high capacity and potential reduction of the film thickness. In the case of a carbon material negative electrode, not only alkali metal ions but also quaternary ammonium salts, quaternary phosphonium salts, transition metal salts and various protonic acids can be used.

The mixing amount of the electrolyte salt varies depending upon the polymer or other components of the ion conductive material that are mixed. However, if the mixing amount is too small, the number of ion carriers is deficient, whereas if it is too large, the mobility is lowered to reduce the ion conductivity. Accordingly, the mixing amount of the electrolyte salt in the ion conductive material is preferably from 0.1 to 70 wt %, more preferably from 1 to 50 wt %.

In the SPE of PGE as one preferred embodiment of the ion conductive material of the laminate of the present invention, an ion conductive material having added thereto an organic compound or a slight amount of water is preferably used as a solvent for the electrolyte, so that the ion conductivity can be further improved. Preferred examples of the solvent which can be used include, among the above-described solvents for use in the ion conductive material, compounds having good compatibility with the polymer used in the SPE or PGE constituting the ion conductive material, and having a large dielectric constant of 1 or more, a boiling point of 70° C. or higher and a wide electrochemical stability range. Accordingly, specific organic solvents are more suitable than water. Examples of the organic solvent include oligoethers such as triethylene glycol dimethyl ether and tetraethylene glycol dimethyl ether, carbonates such as ethylene carbonate, propylene carbonate, dimethyl carbonate, diethyl carbonate, vinylene carbonate and (meth)acryloyl carbonate, lactones such as γ-butyroactone, aromatic nitriles such as benzonitrile and tolunitrile, sulfur- or nitrogen-containing compounds such as dimethylformamide, dimethyl sulfoxide, N-methylpyrrolidone, N-vinylpyrrolidone and sulfolane, phosphate esters, and alcohols such as ethanol, propanol and butanol. Among these, preferred are oligoethers, carbonates and lactones. The solvent includes substances which function also as a non-polymerizable plasticizer of the ion conductive material.

As the addition amount of the solution is increased, the ion conductivity of the SPE or PGE increases. However, if the addition amount is too large, the mechanical strength of the SPE or PGE is reduced. The addition amount is preferably 10 times or less the weight of the polymer used in the SPE or PGE. The solvent which is a polymerizable compound such as vinylene carbonate, (meth)acryloyl carbonate and N-vinyl pyrrolidone is preferably used in combination with an appropriate amount of a non-polymerizable plasticizer to copolymerize with the above-described functional monomer or oligomer, thereby increasing the addition amount of the plasticizer and improving the ion conductivity without causing any reduction in mechanical strength.

In the production method of a battery using the laminate of the present invention, at least one electrode is an electrode containing the above-described electroactive substance and another electrode is an electrode containing the above-described other electroactive substance produced in the same manner or a commonly used electrode. First, at least one of Layer B and Layer C of the laminate of the present invention is peeled off from Layer A. Or, Layer B or Layer C having on the surface thereof facing Layer A a thin layer ($D_1$ or $D_2$) comprising a metal, a metal oxide or carbon, is peeled off together with the thin layer from Layer A. In the following, for the sake of convenience of description, a production method of a battery where Layer B/thin layer $D_1$/Layer A/Layer C is used as a laminate and Layer B/thin layer $D_1$/Layer A obtained by removing Layer C is used in laminating an electrode, is described. However, the laminate is by no means limited to this structure and the outer layer that is removed by peeling is not limited to Layer C. On the Layer A surface of Layer B/thin layer $D_1$/Layer A obtained in the above-described step, namely, on the Layer A surface from which Layer C laminated thereto is removed, one electrode processed into a predetermined shape such as a film, sheet or disc is placed and if desired, bonded under pressure to produce a laminate structure consisting of Layer B/thin layer $D_1$/Layer A/electrode (the term "is placed on the Layer A surface" as used herein is not limited to that a spacial position relationship that is vertical but the relationship may also be inverse or horizontal). In forming a laminate structure consisting of Layer B/thin layer $D_1$/Layer A/electrode, a pressure is preferably applied, if desired, to ensure good contact between the electrode and Layer A. In this case, Layer A most preferably contains a curable substance, or a curable substance capable of being an ion conductive substance after curing or a solution thereof is previously applied, for example, by coating onto the surface of the electrode to be placed on the Layer A surface, to form a thin coating. Then, Layer A containing and/or not containing a curable substance is placed thereon. In this case, after the electrode is placed on the Layer A surface, during and/or after the application of pressure, heating and/or irradiating with the above-mentioned active light is carried out to obtain a laminate structure having very good adhesion between the electrode and Layer A.

In laminating an electrode on Layer A, a spacer frame having a predetermined thickness and formed of an insulating material may be placed on the electrode. A laminate structure consisting of Layer B/thin layer $D_1$/Layer A produced from the laminate (Layer B/thin layer $D_1$/Layer A/Layer C) of the present invention previously processed, for example, by cutting, into a size matching the frame shape and size or a laminate structure consisting of Layer B/thin layer $D_1$/Layer A previously processed, for example, by cutting, into a size matching the frame size, may be placed within the spacer frame on the electrode, to form a laminate structure with a spacer consisting of Layer B/thin layer $D_1$/Layer A/electrode.

Then, Layer B/thin layer $D_1$ of the laminate structure consisting of Layer B/thin layer $D_1$/Layer A/electrode is removed, for example, by peeling. On the Layer A surface of the laminate structure consisting of Layer A/electrode thus obtained, the other electrode which is processed in the same manner into a predetermined shape and size such as a film, sheet or disc, as the electrode already laminated, is placed and then, if desired, bonded under pressure to produce a laminate structure consisting of electrode/Layer A/electrode (also in this case, the term "is placed on the Layer A surface" is not limited to a spacial position relationship that is vertical but the relationship may also be inverse or horizontal). In forming a laminate structure consisting of electrode/Layer A/electrode, a pressure is preferably applied, if desired, to ensure good contact between the electrode and Layer A. In this case, Layer A most preferably contains a curable substance, or a curable substance capable of being an ion conductive substance after curing or a solution thereof is previously applied, for example, by coating to the surface of the electrode to be placed on the Layer A surface, to form a thin coating. Then, Layer A containing and/or not containing a curable substance is placed thereon. In this case, after the electrode is placed on the Layer A surface, heating and/or irradiating with active light is performed during and/or after the application of pressure to obtain a laminate structure having very good adhesion between the electrode and Layer A.

Examples of the active light include ultraviolet light, visible light, near infrared light, far infrared light, an electron beam, a γ beam and X rays. An appropriate light may be used in combination with a curable substance or an initiator.

Each electrode of the laminate consisting of electrode/Layer A/electrode produced as described above is connected, if desired, to a current collecting body. After placing the laminate in a structure constituting a battery or when the current collecting body also serves as a structure constituting the battery as such, the structure is subjected to known processing, for example, sealing of an open edge part with an insulating sealant such as an epoxy resin or polyolefin resin, to obtain a battery.

In the production method of a battery of the present invention, the above-described current collecting body may be previously connected to the electrode at any step before production of a laminate consisting of electrode/Layer A/electrode.

According to the production method of a battery using the ion conductive laminate of the present invention, a high-quality secondary battery using a whole solid type SPE or PGE having a homogeneous thickness, such as a lithium secondary battery and a lithium ion secondary battery, can be produced. In particular, by using the ion conductive laminate of the present invention in the production of a battery, a thin secondary battery can be produced which has a very thin layer comprising a SPE or PGE having a homogeneous thickness in good contact with the electrode. Accordingly, the resulting battery has excellent electrical properties, namely, a rapid charge/discharge property, high coulombic efficiency and cyclability.

Figure 9:
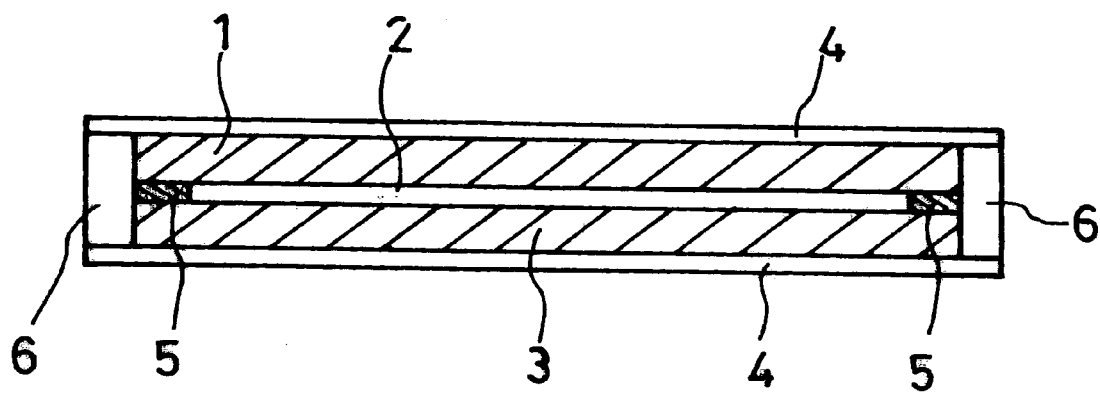
FIG. 9 is a schematic cross section of one example of a thin film solid secondary battery produced according to the present invention.

FIG. 9 shows a schematic cross section of one example of a thin film solid secondary battery as one example of the battery of the present invention produced as described above. In FIG. 9, the numeral 1 is a positive electrode, 2 is a SPE or PGE, 3 is a negative electrode, 4 is a current collecting body, 5 is an insulating spacer and 6 is an insulating resin sealant.

Using the ion conductive laminate of the present invention, a roll-type battery can also be produced. A laminate consisting of positive electrode/Layer A/thin layer $D_1$/Layer B and a laminate consisting of negative electrode/Layer A/thin layer $D_1$/Layer B is produced by the same method as described above, thin layer $D_1$/Layer B is peeled from the respective laminates and, for example, a film-type laminate consisting of positive electrode/Layer A/negative electrode/Layer A or negative electrode/Layer A/positive electrode/Layer A is produced in the same manner as described above. A lead wire is connected to each electrode, the resulting film laminate is rolled into a desired roll, and the roll is inserted into a structure constituting a battery and sealed according to a known sealing method to obtain a roll-type battery. After inserting the roll into the structure constituting a battery, for example, a curable substance used in constructing an ion conductive substance constituting Layer A, a SPE or PGE, or a mixture thereof, maybe injected and polymerized. The structure may then be sealed according to a known method to obtain a roll-type battery.

An example of the production method of a solid electrical double layer capacitor using the ion conductive laminate of the present invention is described in detail below.

The kind of ionic substance used in Layer A comprising an ionic conductive material of the present invention and present in the SPE or PGE of a solid electrical double layer capacitor thus produced is not particularly limited and compounds containing an ion intended to be a charge carrier may be used. However, the compound preferably has a large dissociation constant in a SPE or PGE and contains ions which readily form a polarizable electrode and an electrical double layer. Examples of such a compound include quaternary ammonium salts such as $(CH_3)_4NBF_4$ and $(CH_3CH_2)_4NClO_4$, transition metal salts such as $AgClO_4$, quaternary phosphonium salts such as $(CH_3)_4PBF_4$, alkali metal salts such as $LiCF_3SO_3$, $LiPF_6$, $LiClO_4$, $LiI$, $LiBF_4$, $LiSCN$, $LiAsF_6$, $LiN(CF_3SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$, organic acids such as p-toluenesulfonic acid and salts thereof, and inorganic acids such as hydrochloric acid and sulfuric acid. Among these, quaternary ammonium salts, quaternary phosphonium salts and alkali metal salts are preferred because they are capable of providing high output voltage and a large dissociation constant. Among quaternary ammonium salts, preferred are those having different substituents on the nitrogen of the ammonium ion such as $(CH_3CH_2)(CH_3CH_2CH_2CH_2)_3NBF_4$ because of their high solubility and large dissociation constant in the SPE or PGE.

With respect to the solid electrical double layer capacitor produced using the ion conductive laminate of the present invention, by using SPE or PGE comprising the ion conductive material and having a homogenized thickness, a whole solid electrical double layer capacitor having a high output voltage, a large takeout current and excellent proccessability and reliability can be provided.

Figure 10:
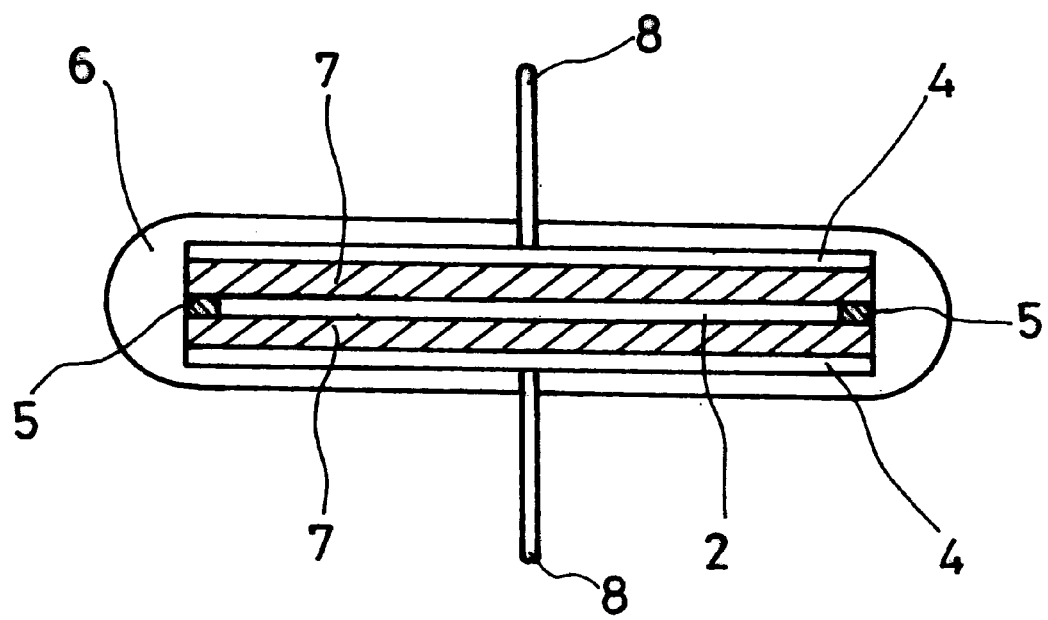
FIG. 10 is a schematic cross section of one example of a solid electrical double layer capacitor produced according to the present invention.

FIG. 10 shows a schematic cross section of one example of the solid electrical double layer capacitor of the present invention. The numeral 4 is a current collecting body, a pair of polarizable electrodes 7 are disposed inside the current collecting body and SPE or PGE 2 is disposed therebetween. The numeral 5 is an insulating spacer, and in this example, an insulating film is used. The numeral 6 is an insulating resin sealant and 8 is a lead wire.

The current collecting body 4 preferably uses a material which is electron conductive and electrochemically anticorrosive and has a specific surface area that is as large as possible. Examples thereof include various metals, a sintered body thereof, electron conductive polymers and carbon sheet.

The polarizable electrode 7 may be an electrode comprising a polarizable material such as a carbon material usually used in an electrical double layer capacitor. However, a carbon material compounded with the ion conductive material constituting Layer A of the ion conductive laminate of the present invention or a precursor material thereof is preferred. The carbon material as a polarizable material is not particularly limited as long as it has a large specific area, however, carbon materials having a larger specific area are preferred because the electrical double layer can have a larger capacity. Examples thereof include carbon blacks such as furnace black, thermal black (including acetylene black) and channel black, activated carbons such as coconut husk carbon, natural graphite, artificial graphite, so-called pyrolytic graphite produced by a vapor phase process, polyacene, $C_{60}$ and $C_{70}$.

In producing a polarizable electrode comprising a polarizable material such as a carbon material and a polymer obtainable from at least one curable substance (polymerizable monomer) and/or a copolymer containing the compound as a copolymer component, which is preferably used in the solid electrical double layer capacitor, first, for example, at least one compound having a structure substituted by the unit represented by formula (1) and if desired, other polymerizable compounds and/or a solvent are added to and mixed with a polarizable material. In this case, the mixing ratio of each component is appropriately determined according to the objective capacitor. The resulting polymerizable monomer/polarizable material mixture is formed into a film on a substrate, for example, on a current collecting body and then polymerized by the same heating and/or irradiating with active light as described above to produce a polarizable electrode. According to this method, a composite thin film electrode in good contact with the current collecting body can be produced.

Using two sheets of polarizable electrodes produced as described above and according to the same method as the above-described production method of a battery, a laminate structure consisting of polarizable electrode/Layer A/polarizable electrode is produced. Also in this case, the polarizable electrode, the laminate of the present invention or the laminate structure after removal of one outer layer may be previously processed into a desired size or shape and then used in the production of a laminate structure consisting of polarizable electrode/Layer A/polarizable electrode.

Each electrode of the thus-produced laminate consisting of electrode/Layer A/electrode is connected, if desired, to a current collecting body, and after placing it in a structure constituting a capacitor or when the current collecting body also serves as a structure constituting a capacitor as such, the structure is subjected to known processing, for example, sealing of an open edge part with an insulating sealant such as an epoxy resin or polyolefin resin, to thereby obtain a capacitor.

In the production method of a capacitor of the present invention, at any step before production of a laminate consisting of electrode/Layer A/electrode, the above-described current collecting body may be previously connected to the electrode.

According to the production method of a capacitor using the ion conductive laminate of the present invention, a high-quality, for example, whole solid electrical double layer capacitor using a whole solid type SPE or PGE having a homogeneous thickness can be produced. In particular, by using the ion conductive laminate of the present invention in the production of a capacitor, a thin whole solid type electrical double layer capacitor can be produced which has a very thin SPE or PGE layer having a homogeneous thickness in good contact with the electrode. Accordingly, the resulting capacitor has excellent electrical properties, namely, a rapid charge/discharge property, high coulombic efficiency and cyclability.

The shape of the electrical double layer capacitor may be, in addition to a sheet form as shown in FIG. 10, a coin form or a cylindrical form which is produced by rolling a sheet laminate of polarizable electrodes and a SPE or PGE into a cylinder, placing it in a cylindrical tube-type structure constituting the capacitor, and sealing the structure.

In producing a roll-type capacitor, similarly to the production method of a roll-type battery described above, a method where a film laminate consisting, for example, of a polarizable electrode/Layer A/polarizable electrode/Layer A is prepared, rolled and inserted into a structure constituting a capacitor may also be used. The above-described curable substance or a mixture thereof is further injected therein and polymerized.

The ion conductive laminate of the present invention can be produced, for example, as a laminate having an extremely large area or an extremely large length, for example, 120 mm in width and several hundreds of meters or more in length, by an extrusion molding and wound into a rolled laminate. The laminate of the present invention is characterized, as one of its important characteristic features, in that it can be provided as a laminate having a large-area and a homogenized ion conductive material film. This cannot be achieved by conventional ion conductive materials. The laminate may be cut into a desired size at any stage depending upon the intended application. Accordingly, electrochemical elements and apparatuses having a homogenized ion conductive material layer having an optional thickness and an extremely large area can be produced. Also, the laminate of the present invention can be cut into an extremely fine size and therefore, electrochemical elements and apparatuses having an extremely small, thin and homogenized ion conductive material film can be produced.

EXAMPLES

The present invention is described in greater detail by reference to the following Examples. However, these Examples are set forth for description only, and the present invention should not be construed as being limited thereto.

Example 1

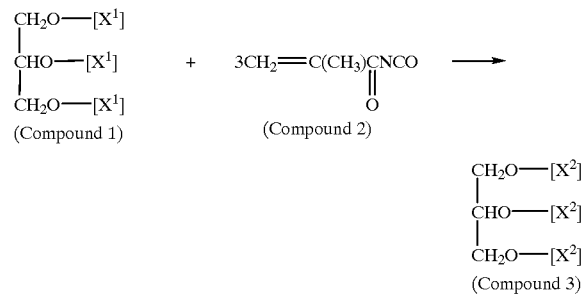

wherein [$X^1$] represents $(CH_2CH_2O)_{p[CH(CH_3)}CH_2O]_qH$ and [$X^2$] represents

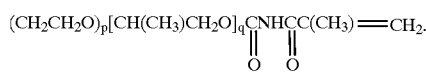

Synthesis of Compound 3

In 100 ml of purified THF, 57.7 g of Compound 1 (KOH value: 34.0 mg/g, p/q=4) and 3.89 g of Compound 2 were dissolved under a nitrogen atmosphere, and thereto 0.44 g of dibutyltin dilaurate was added. Thereafter, the mixture was reacted at 25° C. for about 15 hours to obtain a colorless viscous liquid. From the results of $^1$H-NMR, IR and elemental analysis thereof, it was verified that Compound 1 and Compound 2 were reacted at a molar ratio of 1:3, the isocyanate group of Compound 2 disappeared, a urethane bond was produced, and Compound 3 was produced.

Example 2

Under an argon atmosphere, 1.50 g of Compound 3, 1.5 g of diethyl carbonate (DEC), 1.5 g of ethylene carbonate (EC), 0.30 g of $LiBF_4$ and 0.02 g of Irgacure 500 (produced by Ciba Geigy AG) were well mixed to obtain a photopolymerizable monomer solution.

The resulting polymerizable monomer solution was coated on an alumina layer of a PET film (50 $\mu$m-thick) having vapor-deposited thereon a 500 Å-thick alumina layer, under a nitrogen atmosphere by means of a coater to a thickness of 30 $\mu$m and cured by irradiating under a mercury lamp for 10 minutes to obtain a transparent solid polymer electrolyte (SPE) layer. Furthermore, on the SPE layer, a polypropylene film (30 $\mu$m-thick) was superposed under a nitrogen atmosphere by means of nip rolls to obtain a film laminate consisting of PET/alumina/SPE/polypropylene.

The ion conductivity at 25° C. of the SPE layer of the laminate was measured by an impedance method and determined to be $2\times10^{-3}$ S/cm.

The water content of the SPE layer was 100 ppm (according to Karl Fischer's method). The laminate was stored in a thermostatic chamber at a temperature of 23° C. and a humidity of 60% RH for one hour. Then, the water content of the SPE layer was 120 ppm and had hardly increased from its value prior to storage. The ion conductivity did not change and was $2\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 1,500 ppm and the ion conductivity was reduced to $0.7\times10^{-3}$ S/cm.

The polypropylene and/or PET film as an upper or lower layer could be peeled off from the laminate and the SPE layer could be easily laminated on another substrate such as an electrode.

Example 3

A film laminate consisting of PET/alumina/SPE/polypropylene was obtained in the same manner as in Example 2, except for using 0.40 g of $NaCF_3SO_3$ in place of the $LiBF_4$ used in Example 2. The ion conductivity at 25° C. of the SPE layer of the laminate was measured by an impedance method and determined to be $5\times10^{-3}$ S/cm. The water content of the SPE layer was 90 ppm (according to Karl Fischer's method). The laminate was stored in a thermostatic chamber at a temperature of 23° C. and a humidity of 60% RH for one hour. Then, the water content of the SPE layer was 150 ppm and had hardly increased from its value prior to storage. The ion conductivity did not change and was $5\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 3,000 ppm and the ion conductivity was reduced to $2\times10^{-3}$ S/cm.

The polypropylene and/or PET film as an upper or lower layer could be peeled off from the laminate and the SPE layer could be easily laminated on other substrate such as an electrode.

Example 4

A film laminate consisting of aluminum/SPE/polypropylene was obtained in the same manner as in Example 2, except for using a 25 μm-thick aluminum foil in place of the alumina-evaporated PET film used in Example 2. The ion conductivity at 25° C. of the SPE layer of the laminate was measured by an impedance method and determined to be $2\times10^{-3}$ S/cm. The water content of the SPE layer was 100 ppm (according to Karl Fischer's method). The laminate was stored in a thermostatic chamber at a temperature of 23° C. and a humidity of 60% RH for one hour. Then, the water content of the SPE layer was 115 ppm and had hardly increased from its value prior to storage. The ion conductivity did not change and was $2\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 3,200 ppm and the ion conductivity was reduced to $0.8\times10^{-3}$ S/cm.

The polypropylene film and/or aluminum foil as an upper or lower layer could be peeled off from the laminate and the SPE layer could be easily laminated on another substrate such as an electrode.

Example 5

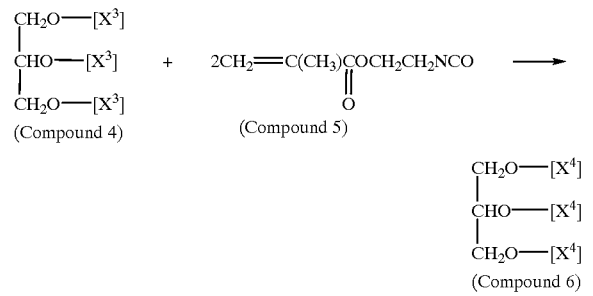

wherein $[X^3]$ represents a 2:1 mixture group of $(CH_2CH_2O)_p[CH(CH_3)CH_2O]_qH$ and $(CH_2CH_2O)_p[CH(CH_3)CH_2O]_qCH_3$, and $[X^4]$ represents a 2:1 mixture group of

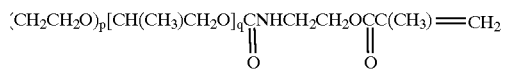

and $(CH_2CH_2O)_p[CH(CH_3)CH_2O]_qCH_3$.

Synthesis of Compound 6

In 100 ml of purified THF, 38.5 g of Compound 4 (KOH value: 22.7 mg/g, p/q=5) and 2.42 g of Compound 5 were dissolved under a nitrogen atmosphere, and thereto 0.29 g of dibutyltin dilaurate was added. Thereafter, the mixture was reacted at 25° C. for about 15 hours to obtain a colorless viscous liquid. From the results of $^1$H-NMR, IR and elemental analysis thereof, it was verified that Compound 4 and Compound 5 were reacted at a molar ratio of 1:2, the isocyanate group of Compound 5 disappeared, a urethane bond was produced, and Compound 6 was produced.

Example 6

Under an argon atmosphere, 1.50 g of Compound 6, 2.0 g of γ-butyrolactone (GBL), 2.0 g of ethylene carbonate (EC), 0.35 g of LiClO$_4$ and 0.02 g of Irgacure 500 (produced by Ciba Geigy AG) were well mixed to obtain a photopolymerizable monomer solution.

The resulting polymerizable monomer solution was coated on the aluminum layer of a PET film (50 μm-thick) having vapor-deposited thereon a 100 Å-thick aluminum layer, under a nitrogen atmosphere by means of a coater to a thickness of 30 μm and irradiated under a mercury lamp for 1 minute to form a SPE layer. Furthermore, on the SPE layer, a polypropylene film (30 μm-thick) was laminated and irradiated under a mercury lamp for 10 minutes to obtain a film laminate consisting of PET/aluminum/SPE/polypropylene. The ion conductivity at 25° C. of the SPE layer of the laminate was measured by an impedance method and determined to be $3.5\times10^{-3}$ S/cm. The water content of the SPE layer was 150 ppm (according to Karl Fischer's method). The laminate was stored in a thermostatic chamber at a temperature of 23° C. and a humidity of 60% RH for one hour. Then, the water content of the SPE layer was then 180 ppm and had hardly increased from its value prior to storage. The ion conductivity did not change and was $3.5\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 2,000 ppm and the ion conductivity was slightly reduced to $2.5\times10^{-3}$ S/cm.

The polypropylene and/or PET film as an upper or lower layer could be peeled off from the laminate and the SPE layer could be easily laminated on another substrate such as an electrode.

Example 7

A film laminate consisting of PET/aluminum/SPE/polypropylene was obtained in the same manner as in Example 6 except for using the same amount of tetraglyme (TG) in place of the GBL used in Example 6. The ion conductivity at 25° C. of the SPE layer of the laminate was measured by an impedance method and determined to be $1.5\times10^{-3}$ S/cm. The water content of the SPE layer was 90 ppm (according to Karl Fischer's method). The laminate was stored in a thermostatic chamber at a temperature of 23° C. and a humidity of 60% RH for one hour. Then, the water content of the SPE layer was 150 ppm and had hardly increased from its value prior to storage. The ion conductivity did not change and was $1.5\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 3,000 ppm and the ion conductivity did not change and was $1.5\times10^{-3}$ S/cm.

The polypropylene and/or PET film as an upper or lower layer could be peeled off from the laminate and the SPE layer could be easily laminated on another substrate such as an electrode.

Example 8

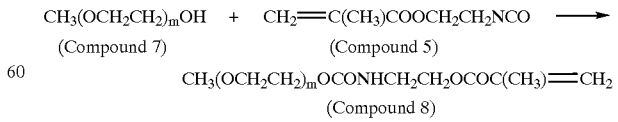

Synthesis of Compound 8

In 100 ml of purified THF, 55 g of Compound 7 (average molecular weight Mn=550) and 15 g of Compound 5 were dissolved under a nitrogen atmosphere, and thereto 0.66 g of dibutylin dilaurate was added. Thereafter, the mixture was reacted at 25° C. for about 15 hours to obtain a colorless viscous liquid. From the results of $^1$H-NMR, IR and elemental analysis thereof, it was verified that Compound 7 and Compound 5 were reacted at a molar ratio of 1:1, the isocyanate group of Compound 5 disappeared, a urethane bond was produced, and Compound 8 was produced.

Example 9

Under an argon atmosphere, to a mixture of 1.5 g of Compound 8 and 0.10 g of $LiClO_4$, 0.01 g of Dalocure 1173 (produced by Ciba Geigy AG) was added and well mixed to obtain a polymerizable monomer solution.

The resulting polymerizable monomer solution was coated on a high-density polyethylene film (30 μm-thick) subjected to corona discharge treatment, under a nitrogen atmosphere by means of a coater to a thickness of 30 μm and irradiated under a mercury lamp for 1 minute to form a SPE layer. Thereafter, on the SPE layer, a polypropylene film (30 μm-thick) was laminated and irradiated under a mercury lamp for 10 minutes to obtain a film laminate consisting of polyethylene/SPE/polypropylene. The ion conductivity at 25° C. of the SPE layer of the laminate was measured by an impedance method and determined to be $1\times10^{-4}$ S/cm. The water content of the SPE layer was 180 ppm (according to Karl Fischer's method). The laminate was stored in a thermostatic chamber at a temperature of 23° C. and a humidity of 60% RH for one hour. Then, the water content of the SPE layer was 180 ppm which was the same as its value prior to storage. Also, the ion conductivity did not change and was $1\times10^{-4}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 800 ppm but the ion conductivity did not change and was $1\times10^{-4}$ S/cm.

The polyethylene film and/or polypropylene film as an upper or lower layer could be peeled off from the laminate and the SPE layer could be easily laminated on another substrate such as an electrode.

Example 10

A film laminate consisting of PET/SPE/polypropylene was obtained in the same manner as in Example 9 except for using a 50 μm-thick PET film in place of the high-density polyethylene film subjected to corona discharge treatment as used in Example 9. The ion conductivity at 25° C. of the SPE layer of the laminate was measured by an impedance method and determined to be $1\times10^{-4}$ S/cm. The water content of the SPE layer was 180 ppm (according to Karl Fischer's method). The laminate was stored in a thermostatic chamber at a temperature of 23° C. and a humidity of 60% RH for one hour. Then, the water content of the SPE layer was 230 ppm and had hardly changed from its value prior to storage. Also, the ion conductivity did not change and was $1\times10^{-4}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 1,000 ppm but the ion conductivity did not change and was $1\times10^{-4}$ S/cm.

The polypropylene and/or PET film as an upper or lower layer could be peeled off from the laminate and the SPE layer could be easily laminated on another substrate such as an electrode.

Example 11

A film laminate consisting of PET/alumina/SPE/polypropylene was obtained in the same manner as in Example 2, except for using 0.50 of tetraethylammonium tetrafluoroborate (TEAB) in place of the $LiBF_4$ used in Example 2. The ion conductivity at 25° C. of the SPE layer of the laminate was measured by an impedance method and determined to be $3\times10^{-3}$ S/cm. The water content of the SPE layer was 300 ppm (according to Karl Fischer's method). The laminate was stored in a thermostatic chamber at a temperature of 23° C. and a humidity of 60% RH for one hour. Then, the water content of the SPE layer was 350 ppm and had hardly increased from its value prior to storage. The ion conductivity did not change and was $1\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 3,500 ppm and the ion conductivity was reduced to $1\times10^{-3}$ S/cm. The polypropylene and/or PET film as an upper or lower layer could be peeled off from the laminate and the SPE layer could be easily laminated on another substrate such as an electrode.

Example 12

A film laminate consisting of PET/alumina/SPE/polypropylene was obtained in the same manner as in Example 2, except for using 0.35 of $LiPF_6$ in place of the $LiBF_4$ used in Example 2. The ion conductivity at 25° C. of the SPE layer of the laminate was measured by an impedance method and determined to be $2.5\times10^{-3}$ S/cm. The water content of the SPE layer was 80 ppm (according to Karl Fischer's method). The laminate was stored in a thermostatic chamber at a temperature of 23° C. and a humidity of 60% RH for one hour. Then, the water content of the SPE layer was 80 ppm and did not increase from its value prior to storage. The ion conductivity did not change and was $2.5\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 3,500 ppm and the ion conductivity was reduced to $0.5\times10^{-3}$ S/cm.

The polypropylene and/or PET film as an upper or lower layer could be peeled off from the laminate and the SPE layer could be easily laminated on another substrate such as an electrode.

Example 13

Under an argon atmosphere, to a mixture of 1.50 g of Compound 3 and 0.2 g of N,N-dimethylacrylamide, 1.5 g of γ-butyrolactone (GBL), 1.5 g of ethylene carbonate (EC), 0.30 g of $LiBF_4$ and 0.02 g of Irgacure 500 (produced by Ciba Geigy AG) were well mixed to obtain a photopolymerizable monomer solution.

The resulting photopolymerizable monomer solution was impregnated into a 30 μm-thick polypropylene-made non-woven fabric (MU3005, produced by Japan Vilene Co.), provided on a polypropylene film (30 μm-thick) under a nitrogen atmosphere and cured by irradiating with a mercury lamp for 10 minutes to obtain a non-woven fabric compounded SPE layer. Furthermore, on the layer, a polypropylene film (30 μm-thick) was laminated under a nitrogen atmosphere by means of nip rolls to obtain a film laminate consisting of polypropylene/SPE/polypropylene. The ion conductivity at 25° C. of the SPE layer was measured by an impedance method and determined to be $1.0 \times 10^{-3}$ S/cm. The water content of the SPE layer was 100 ppm (according to Karl Fischer's method).

The laminate was stored in a thermostatic chamber at a temperature of 23° C. and a humidity of 60% RH for one hour. Then, the water content of the solid polymer electrolyte layer was 110 ppm and had hardly increased from its value prior to storage. The ion conductivity did not change and was $1 \times 10^{-3}$ S/cm.

The polypropylene film on one side was peeled off from the laminate and in the same manner as above, the laminate was stored in a thermostatic chamber at a temperature of 23° C. and a humidity of 60% RH for one hour. As a result, the water content of the SPE layer was increased to 1,500 ppm, and the ion conductivity was slightly reduced to $0.8 \times 10^{-3}$ S/cm.

The polypropylene film on one side or on both sides as an upper or lower layer could be peeled off from the laminate and the SPE layer could be easily laminated on another substrate such as an electrode.

Example 14

Under an argon atmosphere, to a mixture of 1.50 g of Compound 3 and 0.2 g of polyethylene oxide having an average molecular weight of 10,000 (produced by Aldrich KK), 1.5 g of γ-butyrolactone (GBL), 1.5 g of ethylene carbonate (EC), 0.30 g of $LiBF_4$ and 0.02 g of Irgacure 500 (produced by Ciba Geigy AG) were well mixed to obtain a photopolymerizable monomer solution.

The resulting photopolymerizable monomer solution was impregnated into a 150 μm-thick general purpose grade polyethylene net, provided on a PET film (50 μm-thick) under a nitrogen atmosphere and cured by irradiating with a mercury lamp for 10 minutes to obtain a non-woven fabric compounded SPE layer. Furthermore, on the SPE layer, a polypropylene film (30 μm-thick) was laminated by means of nip rolls to obtain a film laminate consisting of PET/SPE/polypropylene.

The ion conductivity at 25° C. of the SPE layer of the laminate was measured by an impedance method and determined to be $1.5 \times 10^{-3}$ S/cm. The water content of the SPE layer was 100 ppm (according to Karl Fischer's method). The laminate was stored in a thermostatic chamber at a temperature of 23° C. and a humidity of 60% RH for one hour. Then, the water content of the SPE layer was 120 ppm and had hardly increased from its value prior to storage. The ion conductivity did not change and was $1.5 \times 10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 2,000 ppm and the ion conductivity was slightly reduced to $1.0 \times 10^{-3}$ S/cm.

The polypropylene and/or PET film as an upper or lower layer could be peeled off from the laminate and the SPE layer could be easily laminated on another substrate such as an electrode.

Example 15

Under an argon atmosphere, 1.50 g of Compound 3, 1.5 g of γ-butyrolactone (GBL), 1.5 g of ethylene carbonate (EC), 0.30 g of $LiClO_4$ and 0.001 g of azobisisobutyronitrile (AIBN) were well mixed to obtain a thermopolymerizable monomer solution.

The thermopolymerizable monomer solution was coated on an alumina layer of a PET film (50 μm-thick) having vapor-deposited hereon a 500 Å-thick alumina layer, under a nitrogen atmosphere by means of a coater to a thickness of about 30 μm. This structure was heated at 60° C. for 5 minutes to partially polymerize and thereby increase the viscosity of the thermopolymerizable monomer solution layer. Thereon, a polypropylene film (30 μm-thick) was superposed and heated at 60° C. for one hour to completely cure the polymerizable monomer solution, to thereby obtain a film laminate consisting of PET/alumina/SPE/polypropylene.

The ion conductivity at 25° C. of the SPE layer was measured by an impedance method and determined to be $1.5 \times 10^{-3}$ S/cm. The water content of the SPE layer was 100 ppm (according to Karl Fischer's method). The laminate was stored in a thermostatic chamber at a temperature of 23° C. and a humidity of 60% RH for one hour. Then, the water content of the SPE layer was 120 ppm and had hardly increased from its value prior to storage. The ion conductivity did not change and was $1.5 \times 10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 2,100 ppm and the ion conductivity was slightly reduced to $1.0 \times 10^{-3}$ S/cm.

The polypropylene and/or PET film as an upper or lower layer could be peeled off from the laminate and the SPE layer could be easily laminated on another substrate such as an electrode.

Example 16

Under an argon atmosphere, 2.0 g of polyethylene oxide having an average molecular weight of 10,000 (produced by Aldrich KK) was dissolved in about 20 g of 1,2-dimethoxyethane (DME) and then 0.20 g of $LiClO_4$ was dissolved therein to obtain a SPE solution.

The resulting SPE solution was coated on an alumina layer of a PET film (50 μm-thick) having vapor-deposited thereon a 500 Å-thick alumina layer, by means of a coater to a thickness of about 100 μm, and dried for 2 hours under a nitrogen atmosphere. Furthermore, a polypropylene film (30 μm-thick) was laminated on the SPE layer under a nitrogen atmosphere by means of nip rolls to obtain a film laminate consisting of PET/alumina/SPE/polypropylene. The laminate was further vacuum dried at room temperature for one hour to remove the remaining DME solution.

The ion conductivity at 25° C. of the SPE layer of the laminate was measured by an impedance method and determined to be $1 \times 10^{-6}$ S/cm. The water content of the SPE layer was 500 ppm (according to Karl Fischer's method). The laminate was stored in a thermostatic chamber at a temperature of 23° C. and a humidity of 60% RH for one hour. Then, the water content of the SPE layer was 500 ppm and had not changed from its value prior to storage. The ion conductivity did not change and was $1 \times 10^{-6}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 1,000 ppm but the ion conductivity did not change.

The polypropylene and/or PET film as an upper or lower layer could be peeled off from the laminate and the SPE layer could be easily laminated on another substrate such as an electrode.

Example 17

Under an argon atmosphere, to a mixture of 1.5 g of methacryl-modified polyethylene glycol (Blenmer PME 400, produced by Nippon Oils & Fats Co., Ltd., average molecular weight: 400) and 0.10 g of $LiClO_4$, 0.01g of Dalocure 1173 (produced by Ciba Geigy AG) were added and well mixed under an argon atmosphere to obtain a photopolymerizable monomer solution.

The resulting photopolymerizable monomer solution was coated on a polyethylene film (30 μm-thick) subjected to corona discharge treatment, under a nitrogen atmosphere by means of a coater to a thickness of 30 μm and irradiated with a mercury lamp for 1 minute to form a SPE layer. Thereafter, on the SPE layer, a polypropylene film (30 μm-thick) was superposed and then irradiated with a mercury lamp for 10 minutes to obtain a film laminate consisting of polyethylene/SPE/polypropylene.

The ion conductivity at 25° C. of the SPE layer of the laminate was measured by an impedance method and determined to be $1 \times 10^{-5}$ S/cm. The water content of the SPE layer was 150 ppm (according to Karl Fischer's method). The laminate was stored in a thermostatic chamber at a temperature of 23° C. and a humidity of 60% RH for one hour. Then, the water content of the SPE layer was 160 ppm which was almost the same as its value prior to storage. The ion conductivity did not change and was $1 \times 10^{-5}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 2,000 ppm but the ion conductivity did not change and was $1 \times 10^{-5}$ S/cm.

The polypropylene and/or PET film as an upper or lower layer could be peeled off from the laminate and the SPE layer could be easily laminated on another substrate such as an electrode.

Example 18

Under an argon atmosphere, to a mixture of 0.75 g of urethane acrylate (UA-101H, produced by Kyoei Sha Yushi Kagaku KK, glycerin dimethacrylate hexamethylenediisocyanate urethane prepolymer) and 0.75 g of polyethylene oxide having an average molecular weight of 5,000 (produced by Aldrich KK), 1.5 g of γ-butyrolactone (GBL), 1.5 g of ethylene carbonate, 0.30 g of $LiBF_4$ and 0.02 g of Irgacure 500 (produced by Ciba Geigy AG) were well mixed under an argon atmosphere to obtain a photopolymerizable monomer solution.

The resulting photopolymerizable monomer solution was coated on a silicon dioxide layer of a PET film (50 μm-thick) having vapor-deposited thereon a 100 Å-thick silicon dioxide layer, under a nitrogen atmosphere by means of a coater to a thickness of 30 μm and irradiated with a mercury lamp for 5 minutes to form a SPE layer. Thereafter, on the SPE layer, a polypropylene film (30 μm-thick) was laminated and then irradiated with a mercury lamp for 20 minutes to obtain a film laminate consisting of PET/silicon dioxide/SPE/polypropylene.

The ion conductivity at 25° C. of the SPE layer was measured by an impedance method and determined to be $3 \times 10^{-5}$ S/cm. The water content of the SPE layer was 300 ppm (according to Karl Fischer's method). The laminate was stored in a thermostatic chamber at a temperature of 23° C. and a humidity of 60% RH for one hour. Then, the water content of the SPE layer was 330 ppm and had hardly increased from its value prior to storage. The ion conductivity did not change and was $3 \times 10^{-4}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 1,500 ppm and the ion conductivity was reduced to $1.0 \times 10^{-4}$ S/cm.

The polypropylene and/or PET film as an upper or lower layer could be peeled off from the laminate and the SPE layer could be easily laminated on another substrate such as an electrode.

Example 19

Under an argon atmosphere, to 1.5 g of polyethylene glycol dimethacrylate (Blenmer PDE-600, produced by Nippon Oils & Facts Co., Ltd.; average molecular weight: 600), 1.0 g of γ-butyrolactone (GBL), 1.0 g of ethylene carbonate (EC), 0.30 g of $LiBF_4$ and 0.02 g of Irgacure 651 (produced by Ciba Geigy AG) were well mixed to obtain a photopolymerizable monomer solution.

The resulting photopolymerizable monomer solution was coated on a silicon dioxide layer of a PET film (50 μm-thick) having vapor-deposited thereon a 100 Å-thick silicon dioxide layer, under a nitrogen atmosphere by means of a coater to a thickness of 30 μm and irradiated with a mercury lamp for 5 minutes to form a SPE layer. Thereafter, on the SPE layer, a polypropylene film (30 μm-thick) was laminated and then irradiated with a halogen lamp for 30 minutes to obtain a film laminate consisting of PET/silicon dioxide/SPE/polypropylene.

The ion conductivity at 25° C. of the SPE layer of the laminate was measured by an impedance method and determined to be $1 \times 10^{-4}$ S/cm. The water content of the SPE layer was 350 ppm (according to Karl Fischer's method). The laminate was stored in a thermostatic chamber at a temperature of 23° C. and a humidity of 60% RH for one hour. Then, the water content of the SPE layer was 360 ppm and had hardly increased from its value prior to storage. The ion conductivity did not change and was $1 \times 10^{-4}$ S/cm.

The polypropylene film was peeled off from the laminate and in the same manner as above, the laminate was stored in a thermostatic chamber at a temperature of 23° C. and a humidity of 60% RH for one hour. As a result, the water content of the SPE layer was increased to 2,500 ppm and the ion conductivity was reduced to $0.7 \times 10^{-4}$ S/cm.

The polypropylene and/or PET film as an upper or lower layer could be peeled off from the laminate and the SPE layer could be easily laminated on another substrate such as an electrode.

Example 20

Under an argon atmosphere, 3.0 g of an acrylonitrile (ACN)/methacrylate (MA) copolymer (produced by Toyobo KK, ACN/MA =20/1 by mol) was swollen with 8.0 g of ethylene carbonate (EC) and 10.0 g of propylene carbonate (PC) and then 2.3 g of $LiClO_4$ was dissolved therein to obtain a polymer gel electrolyte (PGE).

The resulting PGE was spread on a PET film (50 μm-thick) by means of a spatula and on the PGE layer, a polypropylene film (30 μm-thick) wag laminated under a nitrogen atmosphere and subjected to roll press molding to a thickness of the PGE layer of 100 μm, to thereby obtain a film laminate consisting of PET/PGE/polypropylene.

The ion conductivity at 25° C. of the PGE layer of the laminate was measured by an impedance method and determined to be $1\times10^{-3}$ S/cm. The water content of the PGE layer was 100 ppm (according to Karl Fischer's method). The laminate was stored in a thermostatic chamber at a temperature of 23° C. and a humidity of 60% RH for one hour. Then, the water content of the PGE layer was 150 ppm and had hardly increased from its value prior to storage. The ion conductivity did not change and was $1\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the PGE layer was increased to 1,000 ppm. The ion conductivity did not change.

The polypropylene and/or PET film as an upper or lower layer could be peeled off from the laminate and the PGE layer could be easily laminated on another substrate such as an electrode.

Example 21

Under an argon atmosphere, 3.0 g of an acrylonitrile (ACN)/methacrylate (MA) copolymer (produced by Toyobo KK, ACN/MA =20/1 by mol) was swollen with 8.0 g of ethylene carbonate (EC) and 10.0 g of propylene carbonate (PC) and then 2.3 g of $LiClO_4$ was dissolved therein to obtain a PGE. Subsequently, 5 g of spectral grade acetonitrile (AN, produced by Wako Junyaku) was added thereto to obtain a PGE solution.

The resulting PGE solution was coated on an alumina layer of a PET film (50 μm-thick) having vapor-deposited thereon a 500 Å-thick alumina, under a nitrogen atmosphere by means of a coater to a thickness of 200 μm, and dried for 2 hours under a nitrogen atmosphere. Furthermore, a polypropylene film (30 μm-thick) was laminated on the PGE layer under a nitrogen atmosphere by means of nip rolls to obtain a laminate, and the laminate was further vacuum dried at room temperature at 60° C. for one hour to remove the remaining AN to thereby obtain a film laminate consisting of PET/alumina/PGE/polypropylene including a PGE layer having a thickness of about 100 μm.

The ion conductivity at 25° C. of the PGE layer of the laminate was measured by an impedance method and determined to be $1.2\times10^{-3}$ S/cm. The water content of the PGE layer was 110 ppm (according to Karl Fischer's method). The laminate was stored in a thermostatic chamber at a temperature of 23° C. and a humidity of 60% RH for one hour. Then, the water content of the PGE layer was 150 ppm and had hardly increased from its value prior to storage. The ion conductivity did not change and was $1.2\times10^{-3}$ S/cm.

The polypropylene film was peeled off from the laminate and in the same manner as above, the laminate was stored in a thermostatic chamber at a temperature of 23° C. and a humidity of 60% RH for one hour. As a result, the water content of the PGE layer was increased to 1,400 ppm. The ion conductivity was $1.0\times10^{-3}$ S/cm and slightly reduced.

The polypropylene and/or PET film as an upper or lower layer could be peeled off from the laminate and the PGE layer could be easily laminated on another substrate such as an electrode.

Example 22

Under an argon atmosphere, 3.0 g of polyvinylidene fluoride (PVdF, Battery Binder Grade, produced by Kuraray KK) was swollen with 10.0 g of ethylene carbonate (EC) and 10.0 g of γ-butyrolactone (GBL) and then 3.0 g of $LiBF_4$ was dissolved therein to obtain a PGE.

The resulting PGE was spread on a polypropylene film (30 μm-thick) by means of a spatula and further on the PGE layer, a polypropylene film (30 μm-thick) was superposed under a nitrogen atmosphere and subjected to roll press molding to a PGE layer thickness of 100 μm to thereby obtain a film laminate consisting of polypropylene/PGE/polypropylene.

The ion conductivity at 25° C. of the PGE layer of the laminate was measured by an impedance method and determined to be $8\times10^{-4}$ S/cm. The water content of the PGE layer was 120 ppm (according to Karl Fischer's method). The laminate was stored in a thermostatic chamber at a temperature of 23° C. and a humidity of 60% RH for one hour. Then, the water content of the PGE layer was 140 ppm and had hardly increased from its value prior to storage. The ion conductivity was almost unchanged and was $6\times10^{-4}$ S/cm.

The polypropylene film was peeled off from the laminate and in the same manner as above, the laminate was stored in a thermostatic chamber at a temperature of 23° C. and a humidity of 60% RH for one hour. As a result, the water content of the PGE layer was increased to 3,000 ppm. The ion conductivity was reduced to $3\times10^{-4}$ S/cm.

The polypropylene film on one side or on both sides as an upper or lower layer could be peeled off from the laminate and the PGE layer could be easily laminated on another substrate such as an electrode.

Example 23

Production of Lithium Cobaltate/Aluminum Foil Laminate Electrode $Li_2CO_3$ (11 g) and 24 g of $Co_3O_4$ were well mixed, heated at 800° C. for 24 hours under an oxygen atmosphere and crushed to obtain a $LiCoO_2$ powder. The $LiCoO_2$ powder, acetylene black and polyvinylidene fluoride were mixed at a weight ratio of 8:1:1, and thereto excess N-methylpyrrolidone was added to obtain a gelled composition. The composition thus obtained was coated on an aluminum foil having a thickness of about 25 μm in a size of 10 cm×10 cm and then roll molded to a thickness of about 50 μm. The molding was vacuum dried under heating at about 100° C. for 24 hours to obtain a lithium cobaltate/aluminum foil laminate electrode.

Example 24

Under an argon atmosphere, 1.50 g of Compound 6, 2.0 g of γ-butyrolactone (GBL), 2.0 g of ethylene carbonate (EC), 0.35 g of $LiClO_4$ and 0.02 g of Irgacure 500 (produced by Ciba Geigy AG) were well mixed to obtain a photopolymerizable monomer solution.

The resulting photopolymerizable monomer solution was coated on a lithium cobaltate layer of a cut portion of the lithium cobaltate/aluminum foil laminate electrode produced in Example 23, under a nitrogen atmosphere by means of a coater to a thickness of 30 μm and irradiated with a mercury lamp for 1 minute to form a SPE layer. Thereafter, on the SPE layer, a polypropylene film (30 μm-thick) was laminated and then irradiated with a mercury lamp for 10 minutes to obtain a film laminate consisting of aluminum/lithium cobaltate/SPE/polypropylene.

The water content of the SPE layer of the laminate was 80 ppm (according to Karl Fischer's method). The laminate was stored in a thermostatic chamber at a temperature of 23° C. and a humidity of 60% RH for one hour. Then, the water content of the SPE layer was 100 ppm and had hardly increased from its value prior to storage.

The polypropylene film was peeled off from the laminate and in the same manner as above, the laminate was allowed to stand in a thermostatic chamber at a temperature of 23° C. and a humidity of 60% RH for one hour. As a result, the water content of the SPE layer increased to 5,000 ppm.

Example 25

A film laminate consisting of aluminum/lithium cobaltate/ SPE/alumina/PET was obtained in the same manner as in Example 24 except for using a PET film (50 µm-thick) having vapor-deposited thereon an alumina layer having a thickness of 500 Å in place of the polypropylene film used in Example 24.

The water content of the SPE layer of the laminate was 85 ppm (according to Karl Fischer's method). The laminate was stored in a thermostatic chamber at a temperature of 23° C. and a humidity of 60% RH for one hour. Then, the water content of the SPE layer was 100 ppm and had hardly increased from its value prior to storage.

The polypropylene film was peeled off from the laminate and in the same manner as above, the laminate was stored in a thermostatic chamber at a temperature of 23° C. and a humidity of 60% RH for one hour. As a result, the water content of the SPE layer increased to 4,300 ppm.

Example 26
Production of Graphite/Copper Foil Laminate Electrode

To a mixture of MCMB graphite (average particle size: 5 µm) produced by Osaka Gas K.K., a vapor phase process graphite fiber (average fiber size: 0.3 µm, average fiber length: 2.0 µm, heat treated product at 2,700° C.) produced by Showa Denko K.K., and polyvinylidene fluoride (PVdP) at a weight ratio of 8.6:0.4:1.0, and excess N-methylpyrrolidone was added to obtain a gelled composition. The composition thus obtained was coat-molded on copper foil of about 15 µm-thick into a size of 10 cm×10 cm and a thickness of about 50 µm. The molding was vacuum dried under heating at about 100° C. for 24 hours to obtain a graphite/copper foil laminate electrode.

Example 27

The photopolymerizable monomer solution prepared in Example 24 was coated on a graphite layer of a cut portion of the graphite/copper foil laminate electrode prepared in Example 26, under a nitrogen atmosphere by means of a coater to have a thickness of 30 µm and then irradiated with a mercury lamp for 1 minute to form a SPE layer. On the SPE layer, a polypropylene film (30 µm-thick) was laminated and further irradiated with a mercury lamp for 10 minutes to obtain a film laminate consisting of aluminum/ lithium cobaltate/SPE/polypropylene.

The water content of the SPE layer of the laminate was 80 ppm(according to Karl Fischer's method). The laminate was stored in a thermostatic chamber at a temperature of 23° C. and a humidity of 60% RH for one hour. Then, the water content of the SPE layer was 100 ppm and had hardly increased from its value prior to storage. The polypropylene film was peeled off from the laminate and in the same manner as above, the laminate was stored in a thermostatic chamber at a temperature of 23° C. and a humidity of 60% RH for one hour. As a result, the water content of the SPE layer increased to 4,800 ppm.

Example 28
Production of Li Secondary Battery

Under an argon atmosphere, 1.5 g of Compound 6, 2.0 g of γ-butyrolactone (GBL), 2.0 g of ethylene carbonate (EC), 0.35 g of $LiClO_4$ and 0.001 g of benzoyl peroxide were well mixed to obtain a thermopolymerizable monomer solution.

In a glove box under an argon atmosphere, a 25µm-thick lithium foil was cut into a size of 12 mm×12 mm and bonded under pressure to a copper foil (15 µm-thick) in a size of 12 mm×12 mm. The periphery of about 1 mm from four edges thereof was covered by a 5 µm-thick polyimide film as a spacer and the photopolymerizable monomer solution prepared in Example 24 was thinly (about 1 µm) coated on the Li foil. Then, the film laminate produced in Example 2 was cut into a size of 12 mm×12 mm, the polypropylene film layer was peeled off therefrom, the SPE layer was laminated on the lithium foil, and the light from a mercury lamp was Irradiated onto the alumina-evaporated PET side for 10 minutes to cure the polymerizable monomer solution and adhere the lithium foil to the SPE layer. As a result, a film laminate consisting of copper/lithium/SPE/alumina-evaporated PET was obtained.

Then, the lithium cobaltate/alumina foil laminate electrode produced in Example 23 was cut into a size of 12 mm×12 mm and impregnated with the above-described thermopolymerizable monomer solution, and the SPE side of the laminate obtained above from which the alumina-evaporated PET was peeled off was laminated on the lithium cobaltate side. The polymerizable monomer solution was cured by heating at 60° C. for one hour to adhere the SPE to the lithium cobaltate. As a result, a film laminate consisting of copper/lithium/SPE/lithium cobaltate/aluminum was prepared.

The edge part of the laminate was sealed with an epoxy resin to obtain a lithium/SPE/lithium cobaltate secondary battery.

Figure 11:
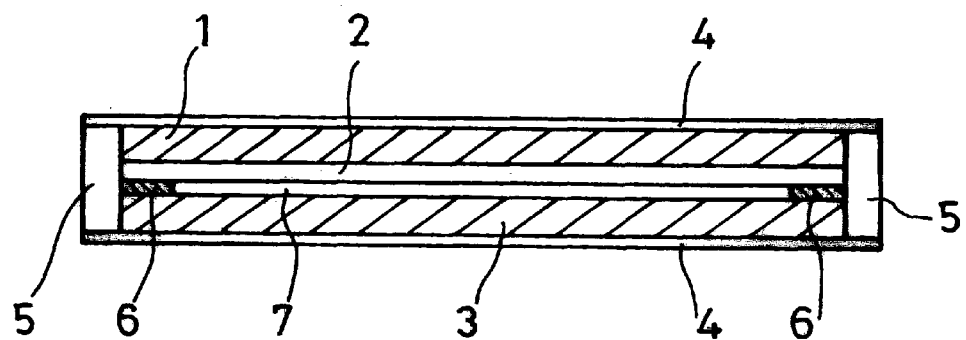
FIG. 11 is a schematic cross section of a battery prepared in the following Examples.

FIG. 11 shows a schematic cross section of the battery thus obtained.

The battery was subjected to repeated charging/ discharging at a working voltage of from 2.0 to 4.2 V and a current of 0.2 mA. As a result, the maximum discharge capacity was 1.8 mAh and the cycle life until the capacity was reduced to 50% was150 cycles.

Example 29
Production of Li Ion Secondary Battery

In a glove box under an argon atmosphere, the graphite/ copper foil laminate electrode produced in Example 26 was cut into a size of 12 mm×12 mm. After covering the periphery of about 1 mm from four edges on the graphite side by a 5 µm-thick polyimide film as a spacer, the laminate was impregnated with the photopolymerizable monomer solution prepared in Example 24. Then, the film laminate produced in Example 2 was cut into a size of 12 mm×12 mm, the polypropylene film layer was peeled therefrom, the SPE layer was laminated on the graphite layer, and the light from a mercury lamp was irradiated onto the alumina-evaporated PET side for 10 minutes to cure the polymerizable monomer solution and adhere the graphite to the SPE layer. As a result, a film laminate consisting of copper/ graphite/SPE/ alumina-evaporated PET was obtained.

Then, the lithium cobaltate/aluminum foil laminate electrode produced in Example 23 was cut into a size of 12 mm×12 mm and impregnated with the thermopolymerizable monomer solution prepared in Example 28, and the SPE side of the laminate obtained above from which the alumina-evaporated PET was peeled off was laminated on the lithium cobaltate side. The polymerizable monomer solution was cured by heating at 60° C. for one hour to adhere the SPE to the lithium cobaltatel. As a result, a film laminate consisting of copper/graphite/SPE/lithium cobaltate/aluminum was prepared.

The edge part of the laminate was sealed with an epoxy resin to obtain a graphite/SPE/lithium cobaltate secondary battery similar to that shown in FIG. 11.

The battery was subjected to repeated charging/discharging at a working voltage of from 2.0 to 4.2 V and a current of 0.2 mA. As a result, the maximum discharge capacity was 1.7 mAh and the cycle life until the capacity was reduced to 50% was 410 cyles.

Example 30
Production of Li Ion Secondary Battery

In a glove box under an argon atmosphere, the graphite/copper foil laminate electrode produced in Example 26 was cut into a size of 12 mm×12 mm. After covering the periphery of about 1 mm from four edges on the graphite side by a polyimide film (5 μm-thick) as a spacer, the laminate was impregnated with the thermopolymerizable monomer solution prepared in Example 28. Then, the film laminate consisting of aluminum foil/lithium cobaltate/SPE/polypropylene produced in Example 24 was cut into a size of 12 mm×12 mm, the polypropylene film layer was peeled therefrom, the SPE layer was laminated on the graphite, and the polymerizable monomer solution was cured by heating at 60° C. for one hour to adhere the SPE to the graphite layer. As a result, a film laminate consisting of copper/graphite/SPE/lithium cobaltate/aluminum was obtained.

The edge part of the laminate was sealed with an epoxy resin to obtain a graphite/SPE/lithium cobaltate secondary battery similar to that shown in FIG. 11.

The battery was subjected to repeated charging/discharging at a working voltage of from 2.0 to 4.2 V and a current of 0.2 mA. As a result, the maximum discharge capacity was 1.6 mAh and the cycle life until the capacity was reduced to 50% was 430 cycles.

Example 31
Production of Li Ion Secondary Battery

In a glove box under an argon atmosphere, the film laminate consisting of copper foil/graphite/SPE/polypropylene produced in Example 27 was cut into a size of 12 mm×12 mm, the polypropylene film layer was peeled therefrom, and the thermopolymerizable monomer solution prepared in Example 28 was thinly (about 1 μm) coated on the SPE layer surface. Then, a film laminate consisting of aluminum foil/lithium cobaltate/SPE/polypropylene prepared in Example 24 was cut into a size of 12 mm×12 mm, the polypropylene film layer was peeled therefrom, the SPE layer was laminated on the above solid polymer electrolyte coated with the thermopolymerizable monomer, and the polymerizable monomer solution was cured by heating at 60° C. for one hour to adhere the SPE layers with each other. As a result, a film laminate consisting of copper/graphite/SPE/lithium cobaltate/aluminum was prepared.

Figure 12:
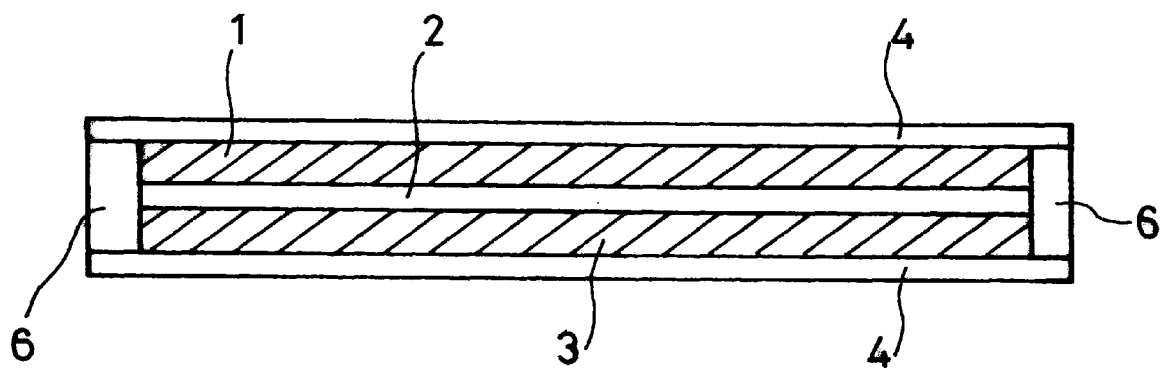
FIG. 12 is a schematic cross section of a battery prepared in the following Examples.

The edge part of the laminate was sealed with an epoxy resin to obtain a graphite/SPE/lithium cobaltate secondary battery. FIG. 12 shows a schematic cross section of the battery thus obtained.

The battery was subjected to repeated charging/discharging at a working voltage of from 2.0 to 4.2 V and a current of 0.2 mA. As a result, the maximum discharge capacity was 1.6 mAh and the cycle life until the capacity was reduced to 50% was 380 cycles.

Example 32
Production of Activated Carbon/SUS Laminate Electrode

To a 9.0:1.0 (by weight) mixture of coconut husk activated carbon and polyvinylidene fluoride (PVdF), excess N-methyl-pyrrolidone was added to obtain a gelled composition. The composition thus obtained was coated on a stainless steel (SUS) foil in a size of 10 cm×10 cm to a thickness of about 150 μm. The coating was vacuum dried at about 100° C. for 10 hours to obtain an activated carbon/SUS laminate electrode.

Example 33

Under an argon atmosphere, 150 g of Compound 8, 4.0 g of propylene carbonate (PC), 0.35 g of $LiBF_4$ and 0.02 g of Irgacure 500 (produced by Ciba Geigy AG) were well mixed to obtain a photopolymerizable monomer solution.

The resulting photopolymerizable monomer solution was, under a nitrogen atmosphere, absorbed into the activated carbon of the activated carbon/SUS laminate electrode produced in Example 32 and further coated thereon by means of a coater to a thickness of 30 μm. Then, the light from a mercury lamp was irradiated onto the laminate for 1 minute to form a SPE layer. Thereafter, on the SPE layer, a polypropylene film (10 μm-thick) was superposed and then irradiated with a mercury lamp for 10 minutes to obtain a film laminate consisting of SUS foil/activated carbon/SPE/polypropylene.

The water content of the SPE layer of the laminate was 180 ppm (according to Karl Fischer's method). The laminate was stored in a thermostatic chamber at a temperature of 23° C. and a humidity of 60% RH for one hour. Then, the water content of the SPE layer was 200 ppm and had hardly increased from its value prior to storage.

The polypropylene film was peeled off from the laminate and in the same manner as above, the laminate was stored in a thermostatic chamber at a temperature of 23° C. and a humidity of 60% RH for one hour. As a result, the water content of the SPE layer increased to 5,000 ppm.

Example 34

Under an argon atmosphere, 1.50 g of Compound 3, 3.0 g of propylene carbonate (PC), 0.30 g of $LiBF_4$ and 0.02 g of Irgacure 500 (produced by Ciba Geigy AG) were well mixed to obtain a photopolymerizable monomer solution.

The resulting photopolymerizable monomer solution was coated on an alumina layer of a PET film (50 μm-thick) having vapor-deposited thereon a 500 Å-thick alumina layer, under a nitrogen atmosphere by means of a coater to a thickness of 30 μm and cured by irradiating with a mercury lamp for 10 minutes to obtain a transparent SPE layer. Furthermore, on the SPE layer, a polypropylene film (30 μm-thick) was laminated under a nitrogen atmosphere by means of nip rolls to obtain a film laminate consisting of PET/alumina/SPE/polypropylene.

The ion conductivity at 25° C. of the SPE layer was measured by an impedance method and determined to be $2 \times 10^{-3}$ S/cm.

The water content of the SPE layer was 180 ppm (according to Karl Fischer's method). The laminate was stored in a thermostatic chamber at a temperature of 23° C. and a humidity of 60% RH for one hour. Then, the water content of the SPE layer was 200 ppm and had hardly increased from its value prior to storage. The ion conductivity did not change and was $2 \times 10^{-3}$ S/cm.

The polypropylene film and/or PET/alumina layer as an upper or lower layer could be peeled off from the laminate and the SPE layer could be easily laminated on another substrate such as an electrode.

Example 35
Production of Electrical Double Layer Capacitor

Under an argon atmosphere, 1.50 g of Compound 8, 4.0 g of propylene carbonate (PC), 0.35 g of $LiBF_4$ and 0.001 g of AIBN were well mixed to obtain a thermopolymerizable monomer solution.

In a glove box under an argon atmosphere, the activated carbon/SUS laminate electrode produced in the same manner as in Example 32 was cut into a size of 12 mm×12 mm and impregnated with the photopolymerizable monomer solution prepared in Example 33. Then, the film laminate prepared in Example 34 was cut into a size of 12 mm×12 mm, the polypropylene film layer was peeled therefrom, the SPE layer was laminated on the activated carbon, and the polymerizable monomer solution was cured by irradiating with a mercury lamp for 10 minutes from the alumina-evaporated PET side to adhere the activated carbon to the SPE layer. As a result, a film laminate consisting of SUS/activated carbon/SPE/alumina-evaporated PET was obtained.

The activated carbon/SUS laminate electrode produced in the same manner as in Example 32 was cut into a size of 12 mm×12 mm and impregnated with the above thermopolymerizable monomer solution, and the activated carbon side was laminated on the SPE side of the SUS/activated carbon/SPE/alumina-evaporated PET laminate from which the alumina-evaporated PET layer was peeled off. Then, the polymerizable monomer solution was cured by heating at 60° C. for one hour to produce a film laminate consisting of SUS/activated carbon/SPE/activated carbon/SUS.

The edge part of the laminate was sealed with an epoxy resin to obtain an electrical double layer capacitor.

Figure 13:
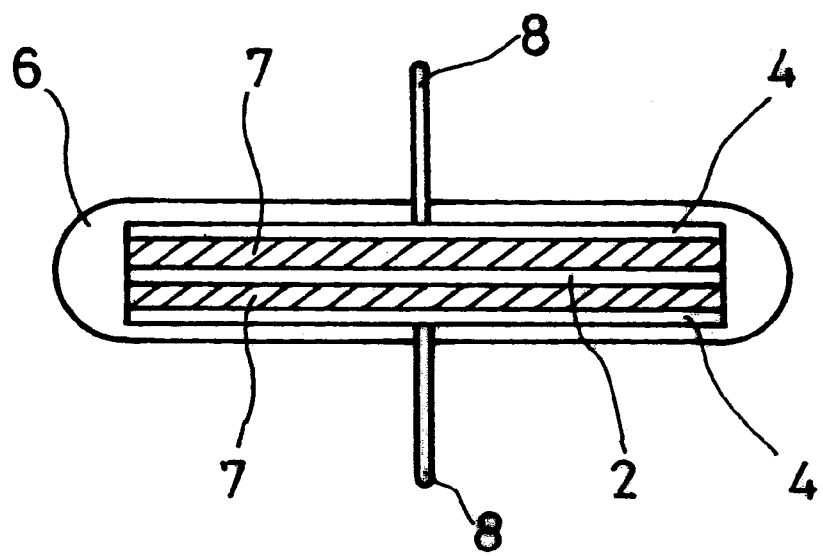
FIG. 13 is a schematic cross section of a solid electrical double layer capacitor prepared in the following Examples.

FIG. 13 shows a schematic cross section of the electrical double layer capacitor thus obtained.

The capacitor was charged/discharged at a working voltage of from 0 to 2.0 V and a current of 0.1 mA. As a result, the maximum capacity was 160 mF. Furthermore, even after repeating the charging/discharging 50 times under the above-described conditions, the capacity was hardly changed.

Example 36
Production of Solid Electrical Double Layer Capacitor

In a glove box under an argon atmosphere, the film laminate consisting of SUS foil/activated carbon/SPE/polypropylene produced in Example 33 was cut into two sheets in a size of 12 mm×12 mm. The polypropylene film layer of one laminate was peeled off and on a surface of the SPE layer, the thermopolymerizable monomer solution prepared in Example 35 was thinly (about 1 $\mu$m) coated. From the other film laminate consisting of SUS foil/activated carbon/SPE/polypropylene, the polypropylene film layer was peeled off and the SPE layer was laminated on the SPE coated with the thermopolymerizable monomer. Then, the polymerizable monomer solution was cured by heating at 60° C. for one hour to adhere the SPE layers to each other. As a result, a film laminate consisting of SUS/activated carbon/SPE/activated carbon/SUS was prepared.

The edge part of the laminate was sealed with an epoxy resin to obtain an electrical double layer capacitor.

FIG. 13 shows a schematic cross section of the electrical double layer capacitor thus obtained.

The capacitor was charged/discharged at a working voltage of from 0 to 2.0 V and a current of 0.1 mA. As a result, the maximum capacity was 170 mF. Furthermore, even after repeating the charging/discharging 50 times under the above-described conditions, the capacity was hardly changed.

Example 37
Preparation of Tungsten Trioxide ($WO_3$) Electrochromic Layer

An ITO (indium tin oxide) glass produced by Matsuzaki Shinku KK was cut into a size of 12 mm×12 mm, the edge was covered, and on the resulting electrode having an ITO exposure area of 10 mm×10 mm, $WO_3$ was vacuum evaporated using a tantalum as a boat member by a resistance heating method at from $10^{-5}$ to $10^{-6}$ Torr. The film thus obtained had a thickness of about 1,000 Å and a density of about 5 $g/cm^3$.

Example 38
Preparation of Electrolytically Polymerized Polyaniline Film

On an electrode of an ITO glass produced by Matsuzaki Shinku KK and cut into a size of 12 mm×12 mm, potential scanning was repeatedly performed in a 1M aqueous hydrochloric acid solution containing 0.5M aniline as an electrolytic solution with an ITO glass of 20 mm×20 mm as a counter electrode in the range of from −0.2 to 0.8 V vs. SCE at a scanning rate of 0.2 V/sec, to form a green and doped, electrically polymerized polyaniline thin film of about 5,000 Å on the ITO glass. Then, the polyaniline thin film was undoped with aqueous ammonia, thoroughly washed with distilled water, and dipped in an aqueous hydrazine solution to obtain a colorless undoped film. The film was vacuum dried at 100° C. for about 3 hours.

Example 39
Production of Electrochromic Display (ECD)

In a glove box under an argon atmosphere, the polyaniline thin film/ITO electrode produced in Example 38 was impregnated with the photopolymerizable monomer solution prepared in Example 24. Then the film laminate prepared in Example 2 was cut out into a size of 12 mm×12 mm, the polypropylene film layer was peeled off, the SPE layer was laminated onto the polyaniline thin film, and the light from a mercury lamp was irradiated onto the laminate for 10 minutes from the alumina-evaporated PET side to cure the polymerizable monomer solution and adhere the polyaniline to the SPE layer. As a result, a film laminate consisting of ITO/polyaniline/SPE/alumina-evaporated PET was obtained.

Then, the $WO_3$/ITO electrode produced in Example 37 was impregnated with the thermopolymerizable monomer solution prepared in Example 28 and the SPE side of the laminate from which the alumina-evaporated PET was peeled off was laminated to the $WO_3$ side. Thereafter, the polymerizable monomer was cured by heating at 60° C. for one hour to adhere the SPE to $WO_3$. A film laminate consisting of ITO/polyaniline/SPE/$WO_3$/ITO was thus obtained.

The edge part of the laminate was sealed with an epoxy resin to obtain an ECD consisting of polyaniline/SPE/$WO_3$.

Figure 14:
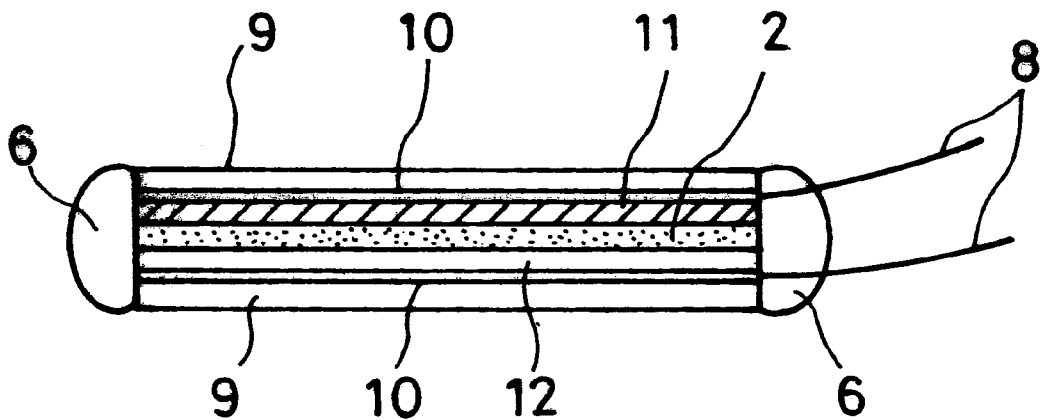
FIG. 14 is a schematic cross section of an ECD prepared in the following Examples.

FIG. 14 shows a schematic cross section of the ECD thus obtained.

The ECD was subjected to repeated coloration/decolorization driving at a working voltage of from −2.0 to 2.0 V and an injection quantity of electricity of 6 $mC/cm^2$. Then, a deep blue/light blue electrochromism was observed. The speed of the response was about 300 msec. Furthermore, even after repeating the driving 100 times under the above-described conditions, the color tone and the speed of response were not changed.

Example 40

Under an argon atmosphere, 1.50 g of Compound 6, 2.0 g of γ-butyrolactone (GBL), 2.0 g of ethylene carbonate (EC), 0.2 g of NaBF$_4$, 0.2 g of NaI and 0.02 g of Irgacure 500 (produced by Ciba Geigy AG) were well mixed to obtain a photopolymerizable monomer solution.

The resulting photopolymerizable monomer solution was coated on an alumina layer of a PET film (50 µm-thick) having vapor-deposited thereon a 500 Å-thick alumina layer, under a nitrogen atmosphere by means of a coater to a thickness of 30 µm and cured by irradiating with a mercury lamp for 10 minutes to obtain a transparent SPE layer. Furthermore, on the SPE layer, a polypropylene film (30 µm-thick) was laminated under a nitrogen atmosphere by means of nip rolls to obtain a film laminate consisting of PET/alumina/SPE/polypropylene.

The ion conductivity at 25° C. of the SPE layer was measured by an impedance method and found to be 5×10$^{-3}$ S/cm. The water content of the SPE layer was 500 ppm (according to Karl Fischer's method). The laminate was stored in a thermostatic chamber at a temperature of 23° C. and a humidity of 60% RH for one hour. Then, the water content of the SPE layer was 500 ppm and had hardly increased from its value prior to storage. The ion conductivity did not change and was 5×10$^{-3}$ S/cm.

The polypropylene and/or PET film as an upper or lower layer could be peeled off from the laminate and the SPE layer could be easily laminated on another substrate such as an electrode.

Example 41

Production of Cd (Se, Te) Photoelectrode

According to the method reported in *Journal of Electrochemical Society*, Vol. 132, page 1077 (1985), a Cd (Se, Te) photoelectrode having a thickness of about 1 µm was produced by electrodepositing from an aqueous sulfuric solution of CdSO$_4$, SeO$_2$ or TeO$_2$ on a titanium electrode having a dimension of 12 mm ×12 mm.

Example 42

Production and Evaluation of Wet-Type Solar Cell (Photoelectrochemical Solar Cell)

The periphery of about 1 mm from four edges of the Cd (Se, Te)/Ti photoelectrode produced above was covered by a 5 µm-thick polyimide film, and the photopolymerizable monomer solution prepared in Example 40 was coated on the Cd (Se, Te) thin film. Then, the film laminate produced in Example 40 was cut into a size of 12 mm×12 mm and the polypropylene film layer was peeled off. The SPE layer was laminated on the Cd (Se, Te) thin film and the light from a mercury lamp was irradiated onto the laminate for 10 minutes from the alumina-evaporated PET side to cure the polymerizable monomer solution and adhere the Cd (Se, Te) thin film to the SPE layer. As a result, a film laminate consisting of Ti/Cd (Se, Te)/SPE/alumina-evaporated PET was obtained.

Then, the photopolymerizable monomer solution prepared in Example 40 was coated on an ITO electrode (12 mm×12 mm) and the SPE side of the laminate obtained above from which the alumina-evaporated PET was peeled off was laminated to the coated surface of the ITO electrode. The light from a mercury lamp was irradiated onto the laminate for 10 minutes from the ITO side to cure the photopolymerizable monomer solution and adhere the ITO to the SPE layer. As a result, a film laminate consisting of Ti/Cd (Se, Te)/SPE/ITO was obtained.

The edge part of the laminate was sealed with an epoxy resin to obtain a Cd (Se, Te)/SPE/ITO wet-type solar cell (photoelectrochemical solar cell).

Figure 15:
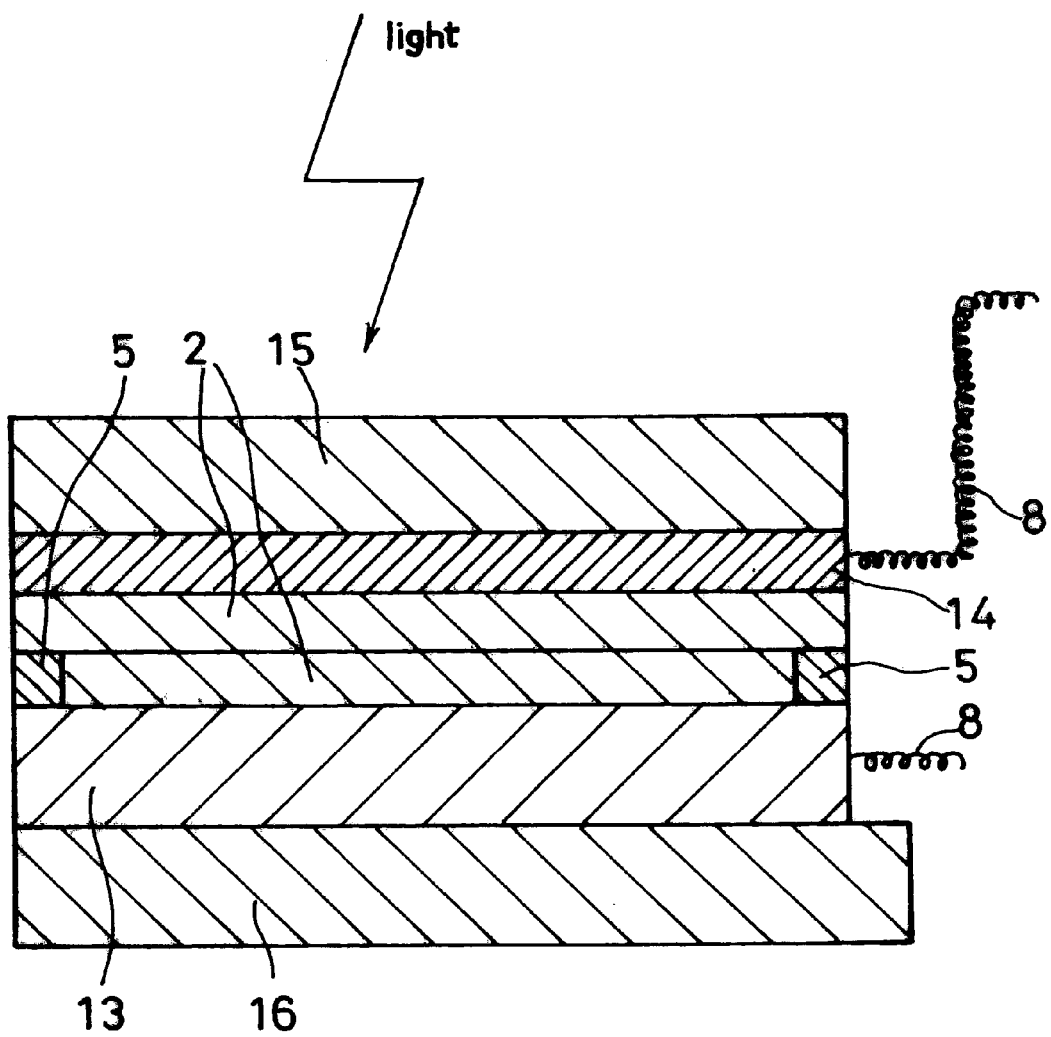
FIG. 15 is a schematic cross section of a solid wet-type solar cell (photoelectrochemical solar cell) prepared in th following Examples.

FIG. 15 shows a schematic cross section of the wet-type solar cell (photoelectrochemical solar cell) thus obtained.

When a tungsten-halogen lamp of 500 W used as a light source was irradiated onto the solar cell for one hour, the open circuit voltage was 0.4 V and in a closed circuit, the current was 0.1 mA/cm$^2$. This was observed for 30 minutes or more, which indicates that the cell was working as a photoelectric cell.

Example 43

On a PET film, ITO was evaporated to a thickness of 1,000 Å and the ITO was soldered with an SUS steel foil as a terminal to obtain a film laminate (12 mm×12 mm; thickness: 30 µm) consisting of ITO layer/PET layer. On the ITO layer of the laminate, the polymerizable monomer solution prepared in Example 9 was coated under a nitrogen atmosphere by means of a coater to a thickness of 30 µm and the light from a mercury lamp was irradiated onto the laminate for 1 minute to form a SPE layer. On the SPE layer, a polypropylene film (30 µm-thick) was laminated and the light from a mercury lamp was further irradiated thereon for 10 minutes to obtain a film laminate consisting of PET/ITO (with SUS terminal)/SPE/polypropylene. The ion conductivity at 25° C. of the SPE layer of the laminate was measured by an impedance method and found to be 1×10$^{-4}$ S/cm. The water content of the SPE layer was 230 ppm (according to Karl Fischer's method). The laminate was stored in a thermostatic chamber at a temperature of 23° C. and a humidity of 60% RH for one hour. Then, the water content of the SPE layer was 230 ppm which was the same as its value prior to storage. The ion conductivity was unchanged and was 1×10$^{-4}$ S/cm.

The polypropylene film layer was peeled off from the laminate and in the same manner as above, the laminate was stored in a thermostatic chamber at a temperature of 23° C. and a humidity of 60% RH for one hour. As a result, the water content of the SPE layer was increased to 800 ppm. The ion conductivity did not change and was 1×10$^{-4}$ S/cm.

The polyethylene film and/or polypropylene film as an upper or lower layer could be peeled off from the laminate and the SPE layer could be easily laminated on another substrate such as an electrode.

The polypropylene film layer was peeled off from the laminate and on the SPE layer of the laminate from which the polypropylene layer was peeled off, the photoelectrode prepared in the same manner as in Example 41 was laminated in the same manner as in Example 42. As a result, a solar cell similar to that of Example 42 was obtained.

Example 44

A silver paste was spray coated only on the edge surfaces opposing to each other of a film laminate consisting of polyethylene/SPE/polypropylene produced in the same manner as in Example 9. Furthermore, a SUS steel-made lead wire was soldered on the silver paste. The resistivity of the SPE portion between two silver paste-coated surfaces was 3×10$^{-4}$ Ω·cm. The laminate could be used as an electrically conductive material of which the upside and down side each was covered with an insulating backing (polyethylene or polypropylene).

The ion conductive laminate of the present invention has an ion conductive material layer having excellent ion conductivity at high temperatures, at room temperature and at low temperatures, a small water content and a homogeneous thickness. Accordingly, the inventive laminate is advantageously used in the production of various electrochemical elements and electrochemical apparatuses such as a secondary battery, an electrical double layer capacitor, an electrochromic display element or apparatus, a photoelectric cell and a solar cell. In particular, when the solid polymer electrolyte (SPE) or polymer gel electrolyte (PGE) is used in electrochemical elements or in electrochemical apparatuses, the capability to process the electrolyte into a desired shape such as a film, the homogeneity of the electrolyte in a laminating step, and the shape stability of the electrolyte such as film thickness and moisture absorption, all of which are problems related to handling the electrolyte, are remarkably improved. Furthermore, the laminate of the present invention is advantageous in the production of various electrochemical elements and apparatuses. Namely, the ion conductive material such as a SPE and PGE having a constant quality can be stored in a state which allows for stable use at any time. Furthermore, the electrolyte quality is consistently excellent and the handling is very easy.

According to the production method of an electrochemical element or electrochemical apparatus using the ion conductive laminate of the present invention, an element or apparatus can be obtained which can be used in layer form such as a film having a homogeneous thickness using a SPE or PGE having a very high quality and a small water content. The production is stable, simple and easy, and can be achieved at high yield, as compared with known methods such as coating.

Furthermore, the ion conductive laminate of the present invention can be used as an electrically conductive material for preventing electrification or for the production of such a material.

The ion conductive laminate of the present invention can be formed into a layer material having any size and shape, and in particular, into a homogeneous and high-quality layer material (e.g., film, sheet, plate) having a very large area and/or length and/or any thickness from ultrathin to bulky. This cannot be achieved with other methods, and this excellent property is not seen in conventional ion conductive materials. Thus, by using the laminate of the present invention, various large-size electrochemical elements and apparatuses described above, which could not be achieved heretofore, can be produced.

While the invention has been described in detail and with reference to specific embodiments thereof, it will be apparent to one skilled in the art that various changes and modifications can be made therein without departing from the spirit and scope thereof.

We claim:

1. A laminate comprising Layer B, Layer A and Layer C disposed in this order, wherein Layer A comprises an ion conductive material having a specific resistivity of $10^6$ Ω·cm or less, Layer B and Layer C comprise a material having an ion conductivity lower than that of Layer A, and at least one of Layer B and Layer C comprises a thermoplastic resin or a composition containing a thermoplastic resin and a non electron-conductive material, wherein at least one of said Layer B and Layer C further comprises a thin layer of a metal selected from the group consisting of aluminum, copper, gold, platinum, silver and stainless steel, a metal oxide selected from the group consisting of alumina and silica or a carbon material selected from the group consisting of graphite, diamond and impermeable carbon materials on the surface facing said Layer A.

2. The laminate according to claim 1, wherein at least one of Layer B and Layer C has a contact angle of 80° or less with polyethylene glycol having an average molecular weight of about 400.

3. The laminate according to claim 1, wherein at least one of Layer B and Layer C has a contact angle of 60° or less with polyethylene glycol having an average molecular weight of about 400.

4. The laminate according to claim 1, wherein Layer B and Layer C are liquid impermeable layers.

5. The laminate according to claim 1, wherein Layer B and Layer C are water impermeable layers.

6. The laminate according to claim 1, wherein at least one of Layer B and Layer C comprises a material having a dielectric constant of 8 or less.

7. The laminate according to claim 1, wherein at least one of Layer B and Layer C has an ion conductivity that is one tenth the ion conductivity of Layer A or less.

8. The laminate according to claim 1, wherein at least one of Layer B and Layer C comprises an engineering plastic, a thermosetting resin or a composition containing one of an engineering plastic or a thermosetting resin.

9. The laminate according to claim 1, wherein the ion conductive material of Layer A has a specific resistivity of $10^5$ Ω·cm or less.

10. The laminate according to claim 1, wherein Layer A has a thickness of from 0.1 to 1,000 μm.

11. The laminate according to claim 1, wherein Layer A has a water content of 200 ppm or less.

12. The laminate according to claim 1, wherein Layer A has a peel strength such that Layer B or Layer C can be peeled off without substantially deforming the shape of Layer A.

13. The laminate according to claim 1, wherein at least one of Layer B and Layer C is a light-transmissible layer.

14. The laminate according to claim 1, wherein neither of Layer B and Layer C are light-transmissible layers.

15. The laminate according to claim 1, wherein both of Layer B and Layer C are gas impermeable layers.

16. The laminate according to claim 1, wherein Layer B or Layer C comprises an electron conductive material, and the electron conductive material-containing layer is connected to an electron conductive electric conductor.

17. The laminate according to claim 1, further comprising electron conductive electric conductors connected to two different sites of Layer A.

18. The laminate according to claim 1, wherein Layer A comprises a material containing a cross-linked polymer as a constituent component.

19. The laminate according to claim 1, wherein Layer A comprises a material containing a cross-linked polymer having at least one alkyleneoxy-containing chain in at least one selected from the group consisting of the main chain and the side chain as a constituent component.

20. The laminate according to claim 1, wherein Layer A comprises a material containing a cross-linked polymer having at least one alkyleneoxy-containing chain and at least one —NH—C(=O)—O— bond in at least one selected from the group consisting of the main chain and the side chain thereof as a constituent component.

21. The laminate according to claim 1, wherein the ion conductive material of Layer A contains at least one of an electrolyte salt and a solvent.

22. The laminate according to claim 21, wherein the electrolyte salt is at least one selected from the group consisting of an alkali metal salt, a quaternary ammonium salt and a quaternary phosphonium salt.

23. The laminate according to claim 21, wherein the solvent is at least one selected from the group consisting of a carbonate derivative, a lactone derivative and an ether derivative, each having a dielectric constant of 1 or more.

24. The laminate according to claim 1, wherein the thin layer is connected to an electron conductive electric conductor.

25. The laminate according to claim 1, wherein Layer A comprises a material containing, as a constituent component, at least one selected from the group consisting of a polymer of a (meth)acryloyl derivative having a structure substituted by at least one unit represented by formula (1) and a copolymer containing said derivative as a copolymer component:

$$CH_2=C(R^1CO(O(CH_2)_x(CH(CH_3))_y)_zNHCOO-R^2- \quad (1)$$

wherein $R^1$ represents hydrogen or an alkyl group, $R^2$ represents a divalent organic group containing an oxyalkylene group, said organic group may have any of linear, branched and cyclic structures and may contain one or more elements other than carbon, hydrogen and oxygen, x and y each represents 0 or an integer of from 1 to 5, z represents 0 or a numerical value of from 1 to 10, provided that when both of x and y are zero, z is zero; the moiety ($CH_2$) and the moiety ($CH(CH_3)$) may be randomly configured, provided that when two or more units represented by formula (1) are present in the same molecule, $R^1$ and $R^2$ of one unit may be different from $R^1$ and $R^2$ of the other units, and the values x, y and z of one unit may be different from the values x, y and z of the other units.

* * * * *